US012091391B2

(12) United States Patent
Mehl et al.

(10) Patent No.: US 12,091,391 B2
(45) Date of Patent: Sep. 17, 2024

(54) REAGENTS AND METHODS FOR BIOORTHOGONAL LABELING OF BIOMOLECULES IN LIVING CELLS

(71) Applicant: Oregon State University, Corvallis, OR (US)

(72) Inventors: Ryan A. Mehl, Corvallis, OR (US); Robert Blizzard, Corvallis, OR (US)

(73) Assignee: Oregon State University, Corvallis, OR (US)

( * ) Notice: Subject to any disclaimer, the term of this patent is extended or adjusted under 35 U.S.C. 154(b) by 119 days.

(21) Appl. No.: 15/570,725

(22) PCT Filed: May 2, 2016

(86) PCT No.: PCT/US2016/030469
§ 371 (c)(1),
(2) Date: Oct. 30, 2017

(87) PCT Pub. No.: WO2016/176689
PCT Pub. Date: Nov. 3, 2016

(65) Prior Publication Data
US 2019/0077776 A1   Mar. 14, 2019

Related U.S. Application Data

(60) Provisional application No. 62/155,333, filed on Apr. 30, 2015.

(51) Int. Cl.
| | |
|---|---|
| *C07D 257/08* | (2006.01) |
| *C07D 257/10* | (2006.01) |
| *C07K 14/435* | (2006.01) |
| *C09B 57/00* | (2006.01) |
| *C12N 9/00* | (2006.01) |
| *C12Q 1/25* | (2006.01) |

(52) U.S. Cl.
CPC ......... *C07D 257/08* (2013.01); *C07D 257/10* (2013.01); *C07K 14/43504* (2013.01); *C09B 57/00* (2013.01); *C12N 9/93* (2013.01); *C12Q 1/25* (2013.01); *C12Y 601/01* (2013.01); *C12Q 2521/501* (2013.01)

(58) Field of Classification Search
CPC ................ A61K 2300/00; A61K 38/00; A61K 39/39558; A61K 2039/505; A61K 47/6889; A61K 47/65; A61K 47/64; A61K 47/6811; A61K 2039/627
See application file for complete search history.

(56) References Cited

U.S. PATENT DOCUMENTS

| | | |
|---|---|---|
| 6,448,281 B1 | 9/2002 | Beaulieu et al. |
| 2008/0233611 A1* | 9/2008 | Schultz ............... C12P 21/00 435/68.1 |

FOREIGN PATENT DOCUMENTS

| | | | | |
|---|---|---|---|---|
| WO | 2013/171485 A1 | 11/2013 | | |
| WO | 2014/065860 A1 | 5/2014 | | |
| WO | WO2014081301 A1 * | 5/2014 | ............. | A61K 47/48 |
| WO | WO2015054658 A1 * | 4/2015 | ........... | C07D 401/12 |

OTHER PUBLICATIONS

Seitchik et al. Genetically encoded tetrazine amino acid directs rapid site-specific in vivo bioorthogonal ligation with trans-cyclooctenes. J Am Chem Soc. Feb. 15, 2012; 134(6): 2898-2901. (Year: 2012).*
Wang et al. Expanding the Genetic Code for Biological Studies. Chem Biol. Mar. 27, 2009; 16(3): 323-336. (Year: 2009).*
Neumann et al. Encoding multiple unnatural amino acids via evolution of a quadruplet-decoding ribosome. Nature. 2010; 464: 441-444. (Year: 2010).*
De Graaf et al. Nonnatural Amino Acids for Site-Specific Protein Conjugation. Bioconjugate Chem. 2009; 20(7): 1281-1295. (Year: 2009).*
Seitchik et al. Genetically Encoded Tetrazine Amino Acid Directs Rapid Site-Specific in Vivo Bioorthogonal Ligation with trans-Cyclooctenes. J. Am. Chem. Soc. 2012, 134, 2898-2901 and Supplemental Information. (Year: 2012).*
International Search Report and Written Opinion mailed Aug. 11, 2016, issued in corresponding International Application No. PCT/US2016/30469, filed May 2, 2016, 10 pages.
International Preliminary Report on Patentability mailed Oct. 31, 2017, issued in corresponding International Application No. PCT/US2016/030469, filed May 2, 2016, 7 pages.
Partial Supplementary European Search Report mailed Sep. 24, 2018, issued in corresponding European Application No. 16787313.2, filed May 2, 2016, 11 pages.
Extended European Search Report dated Jan. 22, 2019, issued in corresponding European Application No. 16787313.2, filed May 2, 2016, 11 pages.
Communication Pursuant to Article 94(3) EPC mailed Dec. 6, 2019, issued in corresponding European Application No. 16787313.2, filed May 2, 2016, 6 pages.
Extended European Search Report mailed Feb. 23, 2022, issued in corresponding European Patent Application No. 21188043.0, filed May 2, 2016, 12 pages.
Office Action mailed May 5, 2022, issued in corresponding European Patent Application No. 21188043.0, filed May 2, 2016, 10 pages.

(Continued)

*Primary Examiner* — Aradhana Sasan
*Assistant Examiner* — Jia-Hai Lee
(74) *Attorney, Agent, or Firm* — Christensen O'Connor Johnson Kindness PLLC

(57) ABSTRACT

Tetrazine non-canonical amino acids, methods for genetic encoding proteins and polypeptides using the tetrazine amino acids, proteins and polypeptides comprising the tetrazine amino acids, and compositions comprising the proteins and polypeptides having at least one post-translational modification thereof comprising in vivo reaction with the incorporated tetrazine amino acid and a second molecule.

7 Claims, 25 Drawing Sheets

Specification includes a Sequence Listing.

(56) References Cited

OTHER PUBLICATIONS

Office Action mailed Feb. 8, 2024, issued in corresponding European Patent Application No. 21188043.0, filed May 2, 2016, 4 pages.

* cited by examiner

Tet-v1.0

TAMRA-sTCO

Time course of expression for negative control ized this, a simpler approach to detecting new fluorine sites in silicoaluminate frameworks is to use the free energy of dissolution of a fluorine ion in water.

REAGENTS AND METHODS FOR BIOORTHOGONAL LABELING OF BIOMOLECULES IN LIVING CELLS

CROSS-REFERENCE TO RELATED APPLICATION

This application claims the benefit of U.S. Provisional Application No. 62/155,333, filed Apr. 30, 2015, which is incorporated herein by reference in its entirety.

STATEMENT OF GOVERNMENT LICENSE RIGHTS

This invention was made with Government support under Contract Nos. CHE-1112409 and MCB 1518265 awarded by the National Science Foundation and P30 ES00210 awarded by the National Institute of Environmental Health Sciences. The Government has certain rights in the invention.

STATEMENT REGARDING SEQUENCE LISTING

The sequence listing associated with this application is provided in text format in lieu of a paper copy and is hereby incorporated by reference into the specification. The name of the text file containing the sequence listing is 55746_Sequence_Final_2016-04-26.txt. The text file is 1.56 KB; was created on Apr. 26, 2016; and is being submitted via EFS-Web with the filing of the specification.

FIELD OF THE INVENTION

The invention relates to tetrazine-containing amino acids, genetic encoding of the amino acid, and in cellulo bioorthogonal ligation of the encoded protein.

BACKGROUND OF THE INVENTION

The development of bioorthogonal reactions and strategies to apply them in the study of biopolymers has transformed the ability to study and engineer biomolecules. The early successes of this technology inspired nearly two decades of research toward building faster and more selective reactions. The broadly defined bioorthogonal reaction is a selective reaction between functional groups in the presence of biological entities. Great progress has been made at increasing the rate and selectivity of bioorthogonal reactions, but the vast majority of reactions still cannot be used inside living cells because (i) high molecular concentrations in cellular environments increase off target side-reactions, (ii) the reactive functional groups introduced compromise the cellular reducing environment and/or catalytic processes, and (iii) the cell interior is challenging to access efficiently with the necessary functionalized molecules. A few chemoselective reactions have cleared the more stringent in cellulo hurdle, but their sluggish reaction rates prevent utility. The ideal bioorthogonal reaction that functions in cellulo with quantitative yields at low concentrations and with exquisite chemoselectivity is said to represent the holy grail of chemical synthesis.

The goal of the ideal bioorthogonal reaction should be to label molecules in cellulo faster than the rate constants of cellular processes, but without side reactions or degradation of reagents. To compete effectively with cellular processes ideal bioorthogonal reactions need fast kinetics ($>10^4$ $M^{-1}s^{-1}$) to react completely on biological time scales of seconds to minutes and to function at biological concentrations (μM to nM) of both biomolecule and label, high selectivity to ensure only the target biomolecules are modified, functional groups stable enough to enable the labeling of quantitative portions of biomolecules in vivo, and small structural components as to not adversely affect the structure and function of the biomolecule under investigation.

As defined, ideal bioorthogonal reactions would enable access to new scientific inquiry because they could turn on or trap typical biological events in vivo at rates comparable to enzymatic reactions (typically $10^3$-$10^6$ $M^{-1}s^{-1}$). In addition, many applications such as delivery of visual probes in organisms for nuclear medicine, single molecule spectroscopy, and fluorescent imaging demand extremely fast reaction rates because low concentrations of labeling reagents are required. The ideal bioorthogonal reaction will allow short reaction times even at sub-stoichiometric concentrations of labeling reagents. The use of stoichiometric concentrations of labeling reagent reduces background signal and side reactions from excessive unreacted label.

An exciting class of bioorthogonal ligations, inverse-electron demand Diels-Alder (IED-DA), posts rate constants up to $10^6$ $M^{-1}s^{-1}$ between tetrazines and strained trans cyclooctenes. Current functional groups that provide these exceptional rates lack the stability and selectivity to meet the requirements of the ideal bioorthogonal reaction. More stable transcyclooctene (TCO) containing amino acids have been site-specifically incorporated into proteins using genetic code expansion and react in vivo with dipyrimidal-tetrazines showing labeling rates of 5200 $M^{-1}s^{-1}$. Unfortunately, when the reaction rate is increased by adding strain to TCO or electron withdrawing groups to the tetrazine these functional groups lose significant in vivo selectivity. The half-life of (cyclopropane-fused transcylooctene) sTCO in vivo is 0.67 days and therefore is not compatible with genetic code expansion as an amino acid. If instead, a tetrazine amino acid is encoded into the protein then the short half-life of sTCO is acceptable since the sTCO-attached labelling reagent will be consumed prior to significant decomposition.

A tetrazine amino acid (Tet-v1.0) has been site-specifically encoded into proteins showing that this functionality is compatible with genetic code expansion (see FIG. 1A). The in cellulo reaction rate of this tetrazine amino acid with sTCO was faster than most bioorthogonal ligations at 880 $M^{-1}s^{-1}$, but was not fast enough to probe biological reactions as an ideal bioorthogonal reaction. A maximum synthetic yield of 3% and low levels of hydrolysis at the amine linkage are additional weaknesses of this tetrazine amino acid that would limit its utility.

Despite the advances noted above with regard to the development of amino acid labeling reagents, a need exists for amino acid labeling reagents to achieve or approach ideal bioorthogonal ligation reactions. The present invention seeks to fulfill this need and provides further related advantages.

SUMMARY OF THE INVENTION

The present invention provides compositions and methods for producing translational components that genetically encoded tetrazine amino acids in cells that meet the attributes needed for ideal bioorthogonal ligations.

The present invention provides tetrazine non-canonical amino acids, methods for incorporating the tetrazine non-canonical amino acids into proteins and polypeptides, post-translationally modified proteins and polypeptides in which the tetrazine non-canonical amino acids have been incorporated, kits for incorporating the tetrazine non-canonical amino acids into proteins and polypeptides, and methods for selecting tRNA synthetases for incorporating the tetrazine non-canonical amino acids into proteins and polypeptides.

In one aspect, the invention provides tetrazine non-canonical amino acids (also referred to herein as "tetrazine-containing amino acid," "tetrazine compound" or "compound."). The tetrazine non-canonical amino acids are tetrazine-containing amino acids useful in the methods of the invention for incorporating tetrazine-containing residues into proteins or polypeptides (e.g., proteins or polypeptides of interest).

In one embodiment, the tetrazine non-canonical amino acid has the formula:

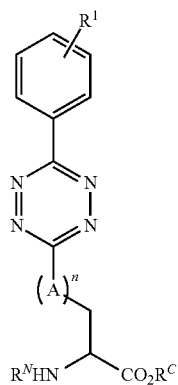

or a stereoisomer or salt thereof, wherein
$R^1$ is selected from hydrogen, substituted and unsubstituted C1-C6 alkyl, C1-C3 haloalkyl, halo, hydroxy, C1-C3 alkoxy, cyano, and nitro;
A is selected from substituted or unsubstituted phenylene or C1-C5 alkylene;
n is 0 or 1;
$R^C$ is hydrogen, a counter ion, or a carboxyl protecting group; and
$R^N$ is hydrogen or an amine protecting group.

In certain of these embodiments, the compound has the formula:

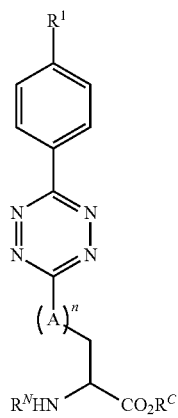

or a stereoisomer or salt thereof.

In the above embodiments when A is phenylene, in certain embodiments, phenylene is 1,4-phenylene and in other embodiments, phenylene is 1,3-phenylene.

In other of these embodiments, the compound has the formula:

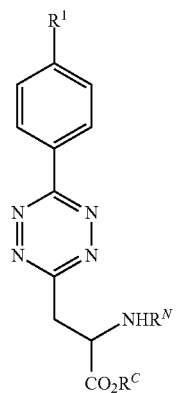

or a stereoisomer or salt thereof.

In further of these embodiments, the compound has the formula:

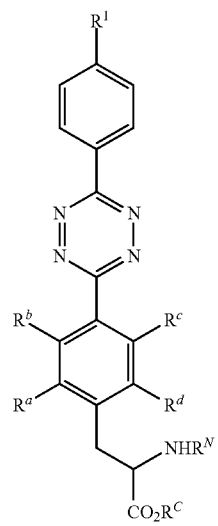

or a stereoisomer or salt thereof, wherein $R^a$, $R^b$, $R^c$, and $R^d$ are independently selected from hydrogen, C1-C3 alkyl, C1-C3 haloalkyl, C1-C3 alkoxy, and halo.

In another of these embodiments, the compound has the formula:

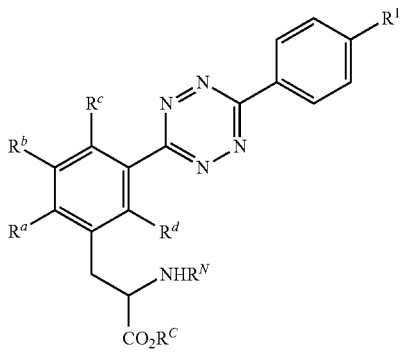

or a stereoisomer or salt thereof, wherein $R^a$, $R^b$, $R^c$, and $R^d$ are independently selected from hydrogen, C1-C3 alkyl, C1-C3 haloalkyl, C1-C3 alkoxy, and halo.

In certain embodiments, for the compounds above, $R^1$ is selected from methyl, ethyl, n-propyl, i-propyl, n-butyl, s-butyl, t-butyl, n-pentyl, and n-hexyl. In other embodiments, for the compounds above, $R^1$ is selected from trifluoromethyl, 2-fluoroethyl, and methoxy.

In certain embodiments, the compound has the formula:

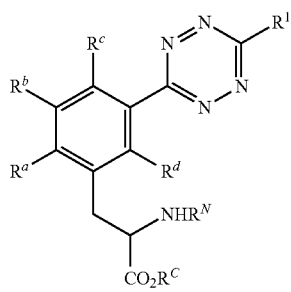

or a stereoisomer or salt thereof, wherein
R is selected from substituted or unsubstituted C1-C6 alkyl group and substituted or unsubstituted phenyl group;
$R^a$, $R^b$, $R^c$, and $R^d$ are independently selected from hydrogen, C1-C3 alkyl, C1-C3 haloalkyl, C1-C3 alkoxy, and halo;
$R^C$ is hydrogen, a counter ion, or a carboxyl protecting group; and
$R^N$ is hydrogen or an amine protecting group.

For the compounds above, in certain embodiments, $R^a$, $R^b$, $R^c$, and $R^d$ are hydrogen, in other embodiments, $R^a$, $R^b$, and $R^d$ are hydrogen, and in further embodiments, $R^a$ and $R^d$ are hydrogen.

Representative tetrazine non-canonical amino acids of the invention include 4-(6-methyl-s-tetrazin-3-yl)phenylalanine (Tet-v2.0-methyl), 4-(6-ethyl-s-tetrazin-3-yl)phenylalanine (Tet-v2.0-ethyl), 4-(6-isopropyl-s-tetrazin-3-yl)phenylalanine (Tet-v2.0-isopropyl), 4-(6-butyl-s-tetrazin-3-yl)phenylalanine (Tet-v2.0-n-butyl), 3-(6-methyl-s-tetrazin-3-yl)phenylalanine (Tet-v3.0-methyl), 3-(6-ethyl-s-tetrazin-3-yl) phenylalanine (Tet-v3.0-ethyl), 3-(6-isopropyl-s-tetrazin-3-yl)phenylalanine (Tet-v3.0-isopropyl), 3-(6-t-butyl-s-tetrazin-3-yl)phenylalanine (Tet-v3.0-t-butyl), and 3-(6-n-butyl-s-tetrazin-3-yl)phenylalanine (Tet-v3.0-n-butyl).

In certain embodiments, the compounds of the invention are amino acids and maybe exist in neutral (e.g., $-NH_2$ and $-CO_2H$) or ionic form (e.g., $-NH_3^+$ and $-CO_2^-$) depending on the pH of the environment. It will be appreciated that the compounds of the invention include a chiral carbon center and that the compounds of the invention can take the form of a single stereoisomer (e.g., L or D isomer) or a mixture of stereoisomers (e.g., a racemic mixture or other mixture). It will be appreciated that the individual stereoisomers and mixtures of isomers are useful in methods of the invention for incorporating tetrazine-containing residues into proteins and polypeptides.

In another aspect, the invention provides methods for making proteins or polypeptides that include tetrazine-containing residues. In one embodiment, the method includes incorporating a tetrazine-containing compound of the invention into the protein or polypeptide. The tetrazine-containing compound can be incorporated into a protein or polypeptide by conventional synthetic techniques (e.g., peptide synthesis, such as solid phase peptide synthesis). Alternatively, the tetrazine-containing compound can be incorporated into a protein or polypeptide by genetic encoding, as described herein in detail. In one embodiment, the invention provides a method for genetically encoding a protein or polypeptide of interest that includes incorporating a tetrazine-containing compound into the protein or polypeptide by genetic encoding.

In a further aspect, the invention provides a protein or polypeptide that includes at least one tetrazine amino acid residue is provided. The tetrazine amino acid residue is derived from a tetrazine-containing compound of the invention. In one embodiment, the invention provides a protein or polypeptide, comprising at least one tetrazine amino acid residue, wherein the tetrazine amino acid residue is incorporated into the protein or polypeptide by genetic encoding of the protein or polypeptide using a tetrazine-containing compound.

In another aspect, the invention comprises a post-translationally modified composition protein or polypeptide (e.g. composition) comprising a protein or polypeptide that comprises at least one tetrazine amino acid residue and at least one post-translational modification, wherein the at least one post-translational modification comprises attachment of a molecule comprising a second reactive group by a [4+2] cycloaddition to the at least one tetrazine amino acid residue comprising a first reactive group.

In certain embodiments, the invention provides a composition comprising a protein or polypeptide, wherein the protein or polypeptide comprises at least one tetrazine amino acid residue comprising a first reactive group and at least one post-translational modification, wherein the tetrazine amino acid residue is derived from a tetrazine-containing compound, wherein the at least one post-translational modification comprises attachment of a molecule comprising a second reactive group by a [4+2] cycloaddition reaction to the at least one tetrazine amino acid residue comprising the first reactive group.

In other embodiments, the invention provides a composition comprising a protein or polypeptide, wherein the protein or polypeptide comprises at least one tetrazine amino acid residue comprising a first reactive group and at least one post-translational modification, wherein the tetrazine amino acid residue is derived from genetic encoding of the protein or polypeptide with a tetrazine-containing compound, wherein the at least one post-translational modification comprises attachment of a molecule comprising a second reactive group by a [4+2] cycloaddition reaction to the at least one tetrazine amino acid residue comprising the first reactive group.

In certain of the embodiments, the first reactive group is the tetrazine group of the tetrazine amino acid residue and the second reactive group is a suitably reactive group reactive (alkyne or alkene, such as a strained alkyne or strained alkene).

In another aspect of the invention, a kit for in cellulo production of a tetrazine-labeled protein or a tetrazine-labeled polypeptide is provided. In certain embodiments, the kit includes:

(a) a tRNA;
(b) an aminoacyl-tRNA synthetase; and
(c) a tetrazine-containing compound,
   wherein the tRNA and aminoacyl-tRNA synthetase are an orthogonal tRNA/orthogonal aminoacyl-tRNA pair effective for incorporating the compound into a protein to provide a tetrazine-labeled protein.

The kit can include additional components to facilitate in cellulo protein production using the tRNA, the aminoacyl-tRNA synthetase, and the tetrazine-containing compound.

In a further aspect, the invention provides a method for selecting an aminoacyl-tRNA synthetase for genetic encoding a protein or polypeptide with a tetrazine-containing amino acid. In embodiments, the method includes:

(a) an efficiency incorporation selection step selecting one or more aminoacyl-tRNA synthetases capable of incorporating a tetrazine-containing amino acid into a protein or polypeptide from a collection of aminoacyl-tRNA synthetases to provide one or more aminoacyl-tRNA synthetases capable of incorporating a tetrazine-containing amino acid; and (b) a fidelity selection step selecting a second set of one or more aminoacyl-tRNA synthetases from the set of aminoacyl-tRNA synthetases are capable of incorporate tetrazine-containing amino acids, wherein the second set of aminoacyl-tRNA synthesases have fidelity to not incorporate canonical amino acids into the protein or polypeptide to provide one or more aminoacyl-tRNA synthetases effective for genetic encoding the protein or polypeptide with a tetrazine-containing amino acid and selective against incorporating canonical amino acids.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

FIG. 1A illustrates the structure of Tet-v1.0. FIG. 1B illustrates the reaction of Tet-v2.0 with sTCO to form the stable conjugate Tet-sTCO. FIG. 1C is an image of the SDS-PAGE analysis of site-specific incorporation of Tet-v2.0 in response to the amber codon: Lane 2 shows expression levels of GFP-wt from pBad-GFP-His$_6$; and Lanes 3 and 4 show the Tet-v2.0 dependent production of GFP-Tet-v2.0. FIG. 1D is a graphic illustration that shows that excitation at 488 nm produces low fluorescence for GFP-Tet, while the reaction forming GFP-Tet-TCO produces full fluorescence for GFP. FIG. 1E is an ESI-Q MS analysis of GFP-Tet-v2.0 showing a single major peak at 27953.3±1 Da. In cellulo reaction of GFP-Tet-v2.0 with sTCO shows a single major peak at 28077.1±1 Da consistent with the expected mass increase from specific and quantitative reaction with sTCO. Each sample did show +22±1 Da and −131±1 Da peaks consistent with the mass of a sodium adduct and the removal of N-terminal methionine. No other peaks were observed that would correlate with background incorporation of natural amino acids.

FIG. 2A shows the kinetics of GFP-Tet-v2.0 with sTCO in vitro resulted in a rate constant of k=87,000±1440 $M^{-1}s^{-1}$ in a PBS buffer at pH 7 at 21° C. FIG. 2B shows the kinetics of GFP-Tet-v2.0 with sTCO in cellulo resulted in rate constant of k=72,500±1660 $M^{-1}s^{-1}$. For both experiments unimolecular rate constants were calculated by fitting the rate of product formation to a single exponential at different concentrations of sTCO, and the bimolecular rate constant was determined using the observed unimolecular rate constants ($k_{obs}$=k[TCO]).

FIG. 3A shows sub-stoichiometric labeling of GFP-Tetv2.0 with sTCO: trace showing fluorescent change from sTCO (excess sTCO) added in; trace shows fluorescent change from the first three additions of ⅓ eq. of sTCO and the fourth addition of excess sTCO (limiting sTCO). FIG. 3B compares concentrations of sTCO in media determined for samples removed after sTCO additions 1-3. Concentrations of sTCO were determined for identical additions of sTCO to buffer alone. FIG. 3C illustrates the structure of TAMRA-sTCO. FIG. 3D shows sub-stoichiometric labeling of E. coli lysate containing expressed GFP-Tet-v2.0 with TAMRA-sTCO. After incubating lysate with TAMRA-sTCO for 1 hour it was run on a 15% SDS-PAGE gel and imaged fluorometrically. Displayed regions correspond to GFP migration and the dye front. Relative band intensities are displayed.

FIG. 22B is the time course for the negative control (no Tet-v3.0-n-butyl). This confirms Tet-v3.0 amino acid incorporation in eukaryotic cells.

FIG. 23A shows a mass shift for only tetrazine amino acid contain protein confirming reactivity of GFP-Tet-3.0-butyl in eukaryotic cells. FIG. 23B shows fluorescence of these GFP-Tet-3.0-butyl containing cells prior to lyses.

DETAILED DESCRIPTION OF THE INVENTION

Figure 1A:
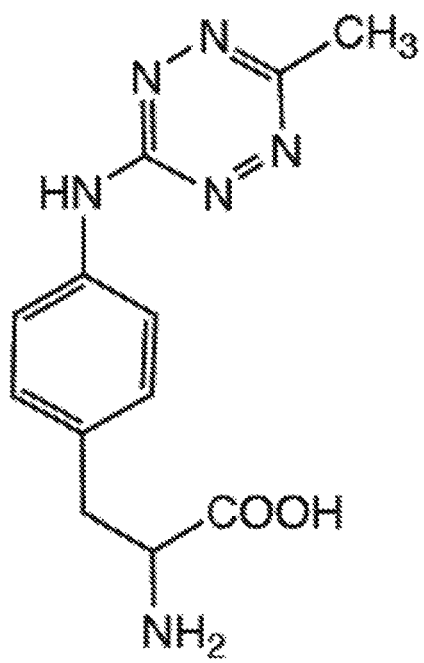
FIGS. 1A-1E illustrate genetic incorporation of a representative tetrazine amino acid of the invention (Tet-v2.0) into proteins and labeling with sTCO.

The present invention provides compositions and methods for producing translational components that genetically encoded tetrazine amino acids in cells that meet the attributes needed for ideal bioorthogonal ligations. The components include orthogonal tRNAs, orthogonal aminoacyl-tRNA synthetases, orthogonal pairs of tRNAs/synthetases and tetrazine amino acids. Proteins containing tetrazine amino acids and methods of producing proteins with tetrazine amino acids in cells are also provided. In order to generate an ideal bioorthogonal reaction with the properties described the tetrazine amino acid reactivity is key to control. The tetrazine amino acid needs to be non-reactive to all biological conditions, in live cells, and in media, but highly reactive with its TCO partner. Orthogonal tRNAs/synthetases then need to be engineered to accept the tetrazine amino acid that contains these reactive properties. This results in tetrazine amino acid tRNA/synthetase pairs that functions in cells to produce proteins with site-specifically incorporated tetrazine amino acids. The tetrazine amino acid containing proteins can then be used in cellulo, in vivo, or in vitro for ideal bioorthogonal ligations. The present invention provides composition and methods for producing tetrazine amino acid tRNA/synthetase pairs that are orthogonal in prokaryotic cells and eukaryotic cells.

The invention provides cells with translation components, e.g., pairs of orthogonal aminoacyl-tRNA synthetases (O-RSs) and orthogonal tRNAs (O-tRNAs) and individual components thereof, that are used in protein biosynthetic machinery to incorporate a tetrazine amino acid in a growing polypeptide chain, in a cell.

Compositions of the invention include a cell comprising an orthogonal aminoacyl-tRNA synthetase (O-RS), where the O-RS preferentially aminoacylates an orthogonal tRNA (O-tRNA) with at least one tetrazine amino acid (i.e., a tetrazine non-canonical amino acid as described herein) in the cell.

The cell also optionally includes the tetrazine amino acid(s). The cell optionally includes an orthogonal tRNA (O-tRNA), where the O-tRNA recognizes a selector codon and is preferentially aminoacylated with the tetrazine amino acid by the O-RS. In one aspect, the O-tRNA mediates the incorporation of the tetrazine amino acid into a protein with, for example, at least 45%, at least 50%, at least 60%, at least 75%, at least 80%, at least 90%, at least 95%, or 99% efficiency.

In another embodiment, the cell comprises a nucleic acid that comprises a polynucleotide that encodes a polypeptide of interest, where the polynucleotide comprises a selector codon that is recognized by the O-tRNA. In one aspect, the yield of the polypeptide of interest comprising the tetrazine amino acid is, e.g., at least 2.5%, at least 5%, at least 10%, at least 25%, at least 30%, at least 40%, 50% or more, of that obtained for the naturally occurring polypeptide of interest from a cell in which the polynucleotide lacks the selector codon. In another aspect, the cell produces the polypeptide of interest in the absence of the tetrazine amino acid, with a yield that is, e.g., less than 35%, less than 30%, less than 20%, less than 15%, less than 10%, less than 5%, less than 2.5%, of the yield of the polypeptide in the presence of the tetrazine amino acid.

The invention also provides a cell comprising an orthogonal aminoacyl-tRNA synthetase (O-RS), an orthogonal tRNA (O-tRNA), the tetrazine amino acid, and a nucleic acid that comprises a polynucleotide that encodes a polypeptide of interest. The polynucleotide comprises a selector codon that is recognized by the O-tRNA. In addition, the O-RS preferentially aminoacylates the orthogonal tRNA (O-tRNA) with the tetrazine amino acid in the cell, and the cell produces the polypeptide of interest in the absence of the tetrazine amino acid, with a yield that is, e.g., less than 30%, less than 20%, less than 15%, less than 10%, less than 5%, less than 2.5% of the yield of the polypeptide in the presence of the tetrazine amino acid.

Compositions that include a cell comprising an orthogonal tRNA (O-tRNA) are also a feature of the invention. Typically, the O-tRNA mediates incorporation of the tetrazine amino acid into a protein that is encoded by a polynucleotide that comprises a selection codon that is recognized by the O-tRNA in vivo. In one embodiment, the O-tRNA mediates the incorporation of the tetrazine amino acid into the protein with at least 45%, at least 50%, at least 60%, at least 75%, at least 80%, at least 90%, at least 95%, or even 99% efficiency.

In one aspect, the invention comprises a composition comprising a protein, wherein the protein comprises at least one tetrazine amino acid and at least one post-translational modification, wherein the at least one post-translational modification comprises attachment of a molecule comprising a second reactive group by a [4+2]cycloaddition to the at least one tetrazine amino acid comprising a first reactive group.

Thus, proteins (or polypeptides of interest) with at least one tetrazine amino acid are also a feature of the invention. In certain embodiments of the invention, a protein with at least one tetrazine amino acid includes at least one post-translational modification. In one embodiment, the at least one post-translational modification comprises attachment of a molecule (e.g., a dye, a polymer [e.g., a derivative of polyethylene glycol], a photocrosslinker, a cytotoxic compound, an affinity label, a derivative of biotin, a resin, a second protein or polypeptide, a metal chelator, a cofactor, a fatty acid, a carbohydrate, a polynucleotide (e.g., DNA, RNA) comprising a second reactive group by a [4+2] cycloaddition to the at least one tetrazine amino acid comprising a first reactive group. For example, the first reactive group is tetrazine moiety (e.g., a tetrazine moiety of a tetrazine non-canonical amino acid as described herein) and the second reactive group is an alkenyl moiety (e.g., a trans-cycloalkenyl moiety, such as sTCO). In certain embodiments, a protein of the invention includes at least one tetrazine amino acid (e.g., a tetrazine non-canonical amino acid as described herein) comprising at least one post-translational modification. In certain embodiments, the post-translational modification is made in vivo in a cell.

Examples of a protein (or polypeptide of interest) include, but are not limited to, a cytokine, a growth factor, a growth factor receptor, an interferon, an interleukin, an inflammatory molecule, an oncogene product, a peptide hormone, a signal transduction molecule, a steroid hormone receptor, erythropoietin (EPO), insulin, human growth hormone, an alpha-1 antitrypsin, an angiostatin, an antihemolytic factor, an antibody, an apolipoprotein, an apoprotein, an atrial natriuretic factor, an atrial natriuretic polypeptide, an atrial peptide, a C—X—C chemokine, T39765, NAP-2, ENA-78, a Gro-a, a Gro-b, a Gro-c, an IP-10, a GCP-2, an NAP-4, an SDF-1, a PF4, a MIG, a calcitonin, a c-kit ligand, a cytokine, a CC chemokine, a monocyte chemoattractant protein-1, a monocyte chemoattractant protein-2, a monocyte chemoattractant protein-3, a monocyte inflammatory protein-1 alpha, a monocyte inflammatory protein-1 beta, RANTES, 1309, R83915, R91733, HCC1, T58847, D31065, T64262, a CD40, a CD40 ligand, a C-kit Ligand, a collagen, a colony stimulating factor (CSF), a complement factor 5a, a complement inhibitor, a complement receptor 1, a cytokine, DHFR, an epithelial neutrophil activating peptide-78, a GRO alpha/MGSA, a GRO beta, a GRO gamma, a MIP-1 alpha, a MIP-1 delta, a MCP-1, an epidermal growth factor (EGF), an epithelial neutrophil activating peptide, an erythropoietin (EPO), an exfoliating toxin, a Factor IX, a Factor VII, a Factor VIII, a Factor X, a fibroblast growth factor (FGF), a fibrinogen, a fibronectin, a G-CSF, a GM-CSF, a glucocerebrosidase, a gonadotropin, a growth factor, a growth factor receptor, a hedgehog protein, a hemoglobin, a hepatocyte growth factor (HGF), a hirudin, a human serum albumin, an ICAM-1, an ICAM-1 receptor, an LFA-1, an LFA-1 receptor, an insulin, an insulin-like growth factor (IGF), an IGF-I, an IGF-II, an interferon, an IFN-alpha, an IFN-beta, an IFN-gamma, an interleukin, an IL-1, an IL-2, an IL-3, an IL-4, an IL-5, an IL-6, an IL-7, an IL-8, an IL-9, an IL-10, an IL-11, an IL-12, a keratinocyte growth factor (KGF), a lactoferrin, a leukemia inhibitory factor, a luciferase, a neurturin, a neutrophil inhibitory factor (NIF), an oncostatin M, an osteogenic protein, an oncogene product, a parathyroid hormone, a PD-ECSF, a PDGF, a peptide hormone, a human growth hormone, a pleiotropin, a protein A, a protein G, a pyrogenic exotoxins A, B, or C, a relaxin, a renin, an SCF, a soluble complement receptor I, a soluble I-CAM 1, a soluble interleukin receptors, a soluble TNF receptor, a somatomedin, a somatostatin, a somatotropin, a streptokinase, a superantigen, a staphylococcal enterotoxin, an SEA, an SEB, an SEC1, an SEC2, an SEC3, an SED, an SEE, a steroid hormone receptor, a superoxide dismutase (SOD), a toxic shock syndrome toxin, a thymosin alpha 1, a tissue plasminogen activator, a tumor growth factor (TGF), a TGF-alpha, a TGF-beta, a tumor necrosis factor, a tumor necrosis factor alpha, a tumor necrosis factor beta, a tumor necrosis factor receptor (TNFR), a VLA-4 protein, a VCAM-1 protein, a vascular endothelial growth factor (VEGEF), a urokinase, a Mos, a Ras, a Raf, a Met; a p53, a Tat, a Fos, a Myc, a Jun, a Myb, a Rel, an estrogen receptor, a progesterone receptor, a testosterone receptor, an aldosterone receptor, an LDL receptor, a SCF/c-Kit, a CD40L/CD40, a VLA-4/VCAM-1, an ICAM-1/LFA-1, a hyalurin/CD44, a corticosterone, a protein present in Genebank or other available databases, and/or a portion thereof. In one embodiment, the polypeptide of interest includes a transcriptional modulator protein (e.g., a transcriptional activator protein (such as GAL4), or a transcriptional repressor protein) or a portion thereof.

The invention also provides methods for producing, in a cell, at least one protein comprising at least one tetrazine amino acid (as well as proteins produced by such methods). The methods include growing, in an appropriate medium, a cell that comprises a nucleic acid that comprises at least one selector codon and encodes the protein. The cell also comprises an orthogonal tRNA (O-tRNA) that functions in the cell and recognizes the selector codon and an orthogonal aminoacyl tRNA synthetase (O-RS) that preferentially aminoacylates the O-tRNA with the tetrazine amino acid, and the medium comprises a tetrazine amino acid. In one embodiment, the O-RS aminoacylates the O-tRNA with the tetrazine amino acid (e.g., at least 45%, at least 50%, at least 60%, at least 75%, at least 80%, at least 90%, at least 95%, or even 99%).

In one embodiment, the method further includes incorporating into the protein the tetrazine amino acid, where the tetrazine amino acid comprises a first reactive group; and contacting the protein with a molecule (e.g., a dye, a polymer, [derivative of polyethylene glycol], a photocrosslinker, a cytotoxic compound, an affinity label, a derivative of biotin, a resin, a second protein or polypeptide, a metal chelator, a cofactor, a fatty acid, a carbohydrate, a polynucleotide [e.g., DNA, RNA]) that comprises a second reactive group. The first reactive group reacts with the second reactive group to attach the molecule to the tetrazine amino acid through a [4+2] cycloaddition. In one embodiment, the first reactive group is tetrazine moiety (e.g., the tetrazine moiety of a tetrazine non-canonical amino acid as described herein) and the second reactive group is an alkenyl moiety (e.g., a trans-cycloalkenyl moiety, such as sTCO).

In certain embodiments, the encoded protein comprises a therapeutic protein, a diagnostic protein, an industrial enzyme, or portion thereof. In one embodiment, the protein that is produced by the method is further modified through the tetrazine amino acid. For example, the tetrazine amino acid is modified through a [4+2] cycloaddition. In another embodiment, the protein produced by the method is modified by at least one post-translational modification (e.g., N-glycosylation, O-glycosylation, acetylation, acylation, lipid-modification, palmitoylation, palmitate addition, phosphorylation, glycolipid-linkage modification) in vivo.

In certain embodiments, the compositions and the methods of the invention include cells. The translation components of the invention can be derived from a variety of organisms (e.g., non-eukaryotic organisms, such as a prokaryotic organism, or an archaebacterium, or a eukaryotic organism).

Kits are also a feature of the invention. For example, a kit for producing a protein that comprises at least one tetrazine amino acid in a cell is provided, where the kit includes a container containing a polynucleotide sequence encoding an O-tRNA or an O-tRNA, and a polynucleotide sequence encoding an O-RS or an O-RS. In one embodiment, the kit further includes at least one tetrazine amino acid (i.e., a tetrazine non-canonical amino acid as described herein). In another embodiment, the kit further comprises instructional materials for producing the tetrazine-containing protein.

As used herein, the term "orthogonal" refers to a molecule (e.g., an orthogonal tRNA (O-tRNA) and/or an orthogonal aminoacyl tRNA synthetase (O-RS)) that functions with endogenous components of a cell with reduced efficiency as compared to a corresponding molecule that is endogenous to the cell or translation system, or that fails to function with endogenous components of the cell. In the context of tRNAs and aminoacyl-tRNA synthetases, orthogonal refers to an inability or reduced efficiency, e.g., less than 20% efficient, less than 10% efficient, less than 5% efficient, or less than 1% efficient, of an orthogonal tRNA to function with an endogenous tRNA synthetase compared to an endogenous tRNA to function with the endogenous tRNA synthetase, or of an orthogonal aminoacyl-tRNA synthetase to function with an endogenous tRNA compared to an endogenous tRNA synthetase to function with the endogenous tRNA. The orthogonal molecule lacks a functional endogenous complementary molecule in the cell. For example, an orthogonal tRNA in a cell is aminoacylated by any endogenous RS of the cell with reduced or even zero efficiency, when compared to aminoacylation of an endogenous tRNA by the endogenous RS. In another example, an orthogonal RS aminoacylates any endogenous tRNA in a cell of interest with reduced or even zero efficiency, as compared to aminoacylation of the endogenous tRNA by an endogenous RS. A second orthogonal molecule can be introduced into the cell that functions with the first orthogonal molecule. For example, an orthogonal tRNA/RS pair includes introduced complementary components that function together in the cell with an efficiency (e.g., 50% efficiency, 60% efficiency, 70% efficiency, 75% efficiency, 80% efficiency, 90% efficiency, 95% efficiency, or 99% or more efficiency) to that of a corresponding tRNA/RS endogenous pair.

One advantage of the tetrazine non-canonical amino acids described herein is that they present additional chemical moieties that can be used to add additional molecules. These modifications can be made in vivo in a eukaryotic cell, or in vitro. Thus, in certain embodiments, the post-translational modification is through the tetrazine non-canonical amino acid. For example, the post-translational modification can be through a [4+2]cycloaddition reaction. Most reactions currently used for the selective modification of proteins involve covalent bond formation between nucleophilic and electrophilic reaction partners (e.g. the reaction of alpha-haloketones with histidine or cysteine side chains). Selectivity in these cases is determined by the number and accessibility of the nucleophilic residues in the protein. In proteins of the invention, other more selective reactions can be used in vitro and in vivo. This allows the selective labeling of virtually any protein with a host of reagents including fluorophores, crosslinking agents, polymers, saccharide derivatives and cytotoxic molecules.

Thus, this invention provides another highly efficient method for the selective modification of proteins, which involves the genetic incorporation of tetrazine amino acids into proteins in response to a selector codon. These tetrazine amino acid side chains can then be modified by a [4+2]

cycloaddition reaction with strained alkenyl derivatives. Because this method involves a cycloaddition rather than a nucleophilic substitution, proteins can be modified with extremely high selectivity. This reaction can be carried out at room temperature in dilute aqueous conditions with excellent regio selectivity.

Tetrazine Non-Canonical Amino Acids

In one aspect, the invention provides tetrazine non-canonical amino acids useful in the methods of the invention for genetically encoding a polypeptide of interest.

In one embodiment, the invention provides a tetrazine amino acid having formula (I):

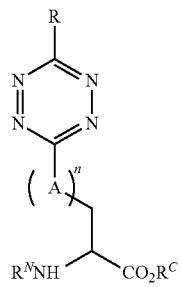

(I)

or a stereoisomer or salt thereof,
wherein
R is selected from substituted or unsubstituted C1-C6 alkyl group and substituted or unsubstituted phenyl group;
A is a substituted or unsubstituted phenylene group or a C1-C5 alkylene group;
n is 0 or 1;
$R^C$ is hydrogen, a counter ion, or a carboxyl protecting group; and
$R^N$ is hydrogen or an amine protecting group.

In certain embodiments, R is an unsubstituted C1-C6 alkyl group (e.g., methyl, ethyl, n-propyl, i-propyl, n-butyl, s-butyl, t-butyl, n-pentyl, n-hexyl) or a substituted C1-C6 alkyl group. Suitable substituents include fluoro (e.g., R is trifluoromethyl or 2-fluoroethyl) and C1-C3 alkoxy (e.g., methoxy), and primary (—$NH_2$), secondary (—$NHR^x$), and tertiary amine (—$NR^xR^y$) (where $R^x$ and $R^y$ are independently C1-C6 alkyl).

In other embodiments, R is an unsubstituted phenyl group or a substituted phenyl group. Suitable substituents include C1-C6 alkyl (e.g., methyl), C1-C3 haloalkyl (trifluoromethyl), halo (e.g., fluoro, chloro), hydroxy, C1-C3 alkoxy (e.g., methoxy), cyano, nitro, and primary (—$NH_2$), secondary (—$NHR^x$), and tertiary amine (—$NR^xR^y$) (where $R^x$ and $R^y$ are independently C1-C6 alkyl).

In certain embodiments, A is a phenylene group (e.g., 1,3- or 1,4-phenylene). In other embodiments, A is an alkylene group (e.g., —$(CH_2)_m$—, where m is 1-5).

Carboxyl protecting groups, amine protecting groups, and counter ions include those known in the art.

As noted above, in one embodiment, the invention provides a tetrazine amino acid of formula (I) with n=0 and the invention provides a tetrazine amino acid having formula (II):

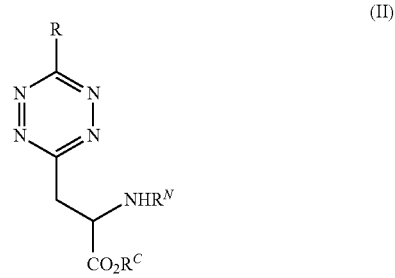

(II)

or a stereoisomer or salt thereof.

Tetrazine amino acids of formula (II) can be prepared by tetrazine-forming reactions (e.g., by reacting a first suitably substituted nitrile and a second suitably substituted nitrile with $Zn(OTf)_2$ and hydrazine, followed by treatment with sodium nitrite and hydrochloric acid, and then HCl in dioxane). Yields for the preparation of compounds ($R^N$ and $R^C$ are H) with R as methyl was 5%.

In another embodiment, the invention provides a tetrazine amino acid of formula (I) with A as 1,4-phenylene (n=1) and the invention provides a tetrazine amino acid having formula (III):

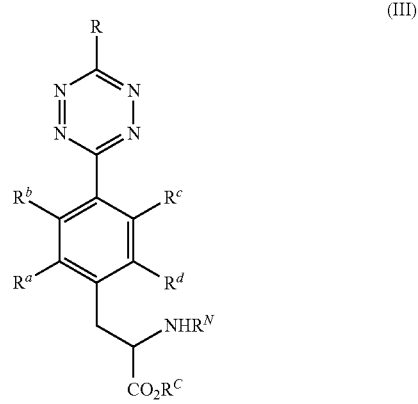

(III)

or a stereoisomer or salt therefore.

In formula (III), $R^a$, $R^b$, $R^c$, and $R^d$ are independently selected from hydrogen, C1-C3 alkyl (e.g., methyl), C1-C3 haloalkyl (e.g., trifluoromethyl), C1-C3 alkoxy (e.g., methoxy), and halo (e.g., fluoro, chloro). In one embodiment, $R^a$, $R^b$, $R^c$, and $R^d$ are hydrogen. In another embodiment, $R^a$, $R^b$, and $R^d$ are hydrogen. In a further embodiment, $R^a$ and $R^d$ are hydrogen.

In a further embodiment, the invention provides a tetrazine amino acid of formula (I) with A as 1,3-phenylene (n=1) and the invention provides a tetrazine amino acid having formula (IV):

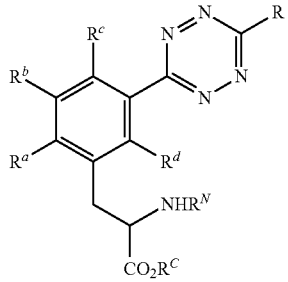

(IV)

or a stereoisomer or salt thereof.

In formula (IV), $R^a$, $R^b$, $R^c$, and $R^d$ are independently selected from hydrogen, C1-C3 alkyl (e.g., methyl), C1-C3 haloalkyl (e.g., trifluoromethyl), C1-C3 alkoxy (e.g., methoxy), and halo (e.g., fluoro, chloro). In one embodiment, $R^a$, $R^b$, $R^c$, and $R^d$ are hydrogen. In another embodiment, $R^a$, $R^b$, and $R^d$ are hydrogen. In a further embodiment, $R^a$ and $R^d$ are hydrogen.

Tetrazine amino acids of formulae (III) and (IV) can be prepared by tetrazine-forming reactions (e.g., by reacting a suitably substituted benzonitrile and a suitably substituted nitrile with $Ni(OTf)_2$ and hydrazine, followed by treatment with sodium nitrite and hydrochloric acid, and then HCl in dioxane). Yields for the preparation of compounds ($R^a$, $R^b$, $R^c$, and $R^d$ are hydrogen; $R^N$ and $R^C$ are H) with R as methyl, ethyl, fluoroethyl, isopropyl, and n-butyl were 60%, 70%, 5%, 58%, and 55%, respectively.

Figure 1B:
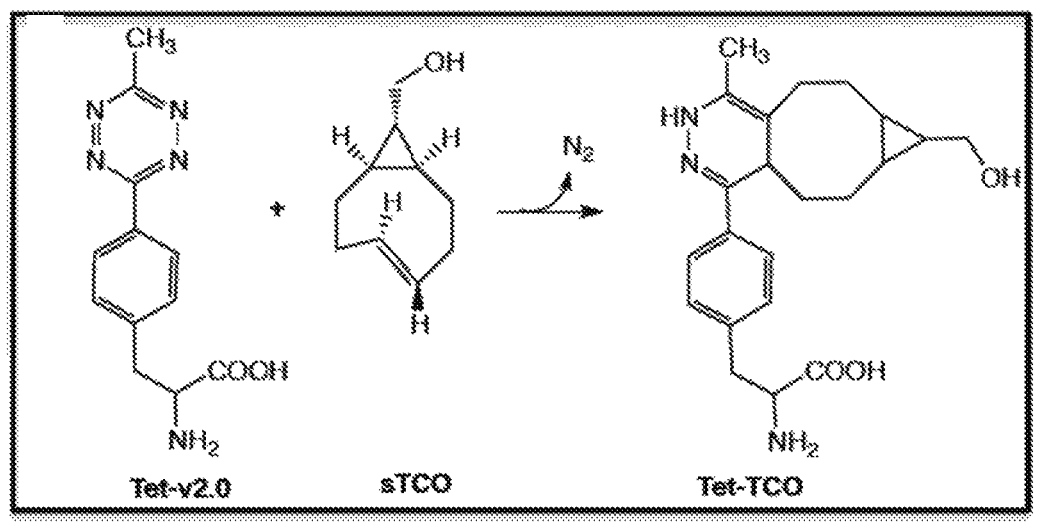

The preparation of a representative tetrazine amino acid useful in the methods of the invention, the tetrazine amino acid of formula (III) where R is methyl and $R^a$, $R^b$, $R^c$, and $R^d$ are hydrogen (i.e., Tet-v2.0 also referred to herein as Tet2.0) is described in Example 1 and illustrated in FIG. 1B.

In another aspect, the invention provides tetrazine non-canonical amino acids having formula (V):

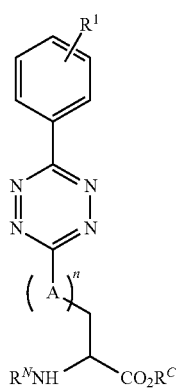

(V)

or a stereoisomer or salt thereof,
wherein
$R^1$ is selected from hydrogen, substituted and unsubstituted C1-C6 alkyl,
C1-C3 haloalkyl, halo, hydroxy, C1-C3 alkoxy, cyano, and nitro;

A is a substituted or unsubstituted phenylene group or a C1-C5 alkylene group;

n is 0 or 1;

$R^C$ is hydrogen, a counter ion, or a carboxyl protecting group; and $R^N$ is hydrogen or an amine protecting group.

In certain embodiments, $R^1$ is an unsubstituted C1-C6 alkyl group (e.g., methyl, ethyl, n-propyl, i-propyl, n-butyl, s-butyl, t-butyl, n-pentyl, n-hexyl) or a substituted C1-C6 alkyl group. Suitable substituents include fluoro (e.g., $R^1$ is trifluoromethyl or 2-fluoroethyl) and C1-C3 alkoxy (e.g., methoxy), and primary (—$NH_2$), secondary (—$NHR^x$), and tertiary amine (—$NR^xR^y$) (where $R^x$ and $R^y$ are independently C1-C6 alkyl).

In other embodiments, $R^1$ is selected from C1-C3 haloalkyl (e.g., trifluoromethyl), halo (e.g., fluoro, chloro), hydroxy, C1-C3 alkoxy (e.g., methoxy), cyano, nitro, and primary (—$NH_2$), secondary (—$NHR^x$), and tertiary amine (—$NR^xR^y$) (where $R^x$ and $R^y$ are independently C1-C6 alkyl).

In certain embodiments, A is a phenylene group (e.g., 1,3- or 1,4-phenylene). In other embodiments, A is an alkylene group (e.g., —$(CH_2)_m$—, where m is 1-5).

Carboxyl protecting groups, amine protecting groups, and counter ions include those known in the art. Suitable carboxyl protecting groups and amine protecting groups are described in Protective Groups in Organic Synthesis, T. W. Greene, John Wiley & Sons, 1981, expressly incorporated herein by reference in its entirety.

Suitable carboxyl protecting groups include ester, amide, and hydrazine groups. Representative ester groups include substituted methyl esters (e.g., methoxymethyl, methylthiomethyl, tetrahydropyranyl, tetrahydrofuranyl, methoxyethoxymethyl, benzyloxymethyl, phenacyl, p-bromophenacyl, α-methylphenacyl, p-methoxyphenacyl, diacylmethyl, N-phthalimidomethyl, and ethyl), 2-substituted ethyl esters (e.g., 2,2,2-trichloroethyl, 2-haloethyl, ω-chloroalkyl, 2-(trimethylsilyl)ethyl, 2-methylthioethyl, 2-(p-nitrophenylsulfenyl)ethyl, 2-(p-toluenesulfonyl)ethyl, 1-methyl-1-phenylethyl, t-butyl, cyclopentyl, cyclohexyl, allyl, cinnamyl, phenyl, p-methylthiophenyl, and benzyl), substituted benzyl esters (e.g., triphenylmethyl, diphenylmethyl, bis(o-nitrophenyl)methyl, 9-anthrylmethyl, 2-(9,10-dioxo)anthrylmethyl, 5-dibenzosuberyl, 2,4,6-trimethylbenzyl, p-bromobenzyl, o-nitrobenzyl, p-nitrobenzyl, p-methoxybenzyl, piperonyl, and 4-picolyl), silyl esters (e.g., trimethylsilyl, triethylsilyl, t-butyldimethylsilyl, i-propyldimethylsilyl, and phenyldimethylsilyl), activated esters (e.g., S-t-butyl, S-phenyl, S-2-pyridyl, N-hydroxypiperidinyl, N-hydroxysuccinimidoyl, N-hydroxyphthalimidoyl, and N-hydroxybenzotriazolyl), stannyl esters (e.g., triethylstannyl, tri-n-butylstannyl), and other esters (e.g., O-acyl oximes, 2,4-dinitrophenylsulfenyl, 2-alkyl-1,3-oxazolidines, 4-alkyl-5-oxo-1,3-oxazolidines, and 5-alkyl-4-oxo-1,3-dioxolanes). Representative amides include N,N-dimethyl, pyrrolidinyl, piperidinyl, o-nitrophenyl, 7-nitroindolyl, and 8-nitrotetrahydroquinolyl. Representative hydrazines include N-phenylhydrazide and N,N'-diisopropylhydrazide.

Suitable amino protecting groups include carbamate and amide groups. Representative carbamate groups include alkyl and aryl carbamate groups (e.g., methyl and substituted methyl, substituted ethyl, substituted propyl and isopropyl, t-butyl, cyclobutyl, cyclopentyl, cyclohexyl, 1-adamantyl, vinyl, allyl, cinnamyl, phenyl, and benzyl). Representative amide groups include N-formyl, N-acetyl, substituted N-propionyl, cyclic imides, N-alkyl amide (e.g., N-allyl, N-phenacyl), amino acetals, N-benzyl amides, imine derivatives, enamine derivatives, N-heteroatom derivatives, N-metal derivatives (e.g., N-borane, N-copper, N-zinc), N—N derivatives (e.g., N-nitro, N-nitroso), N—P derivatives (e.g., phosphinyl, phosphoryl) N—Si derivatives (e.g., N-trimethylsilyl), and N—S derivatives (e.g., N-sulfenyl, N-sulfonyl).

In certain embodiments, the invention provides a tetrazine amino acid of formula (V) having formula (VI):

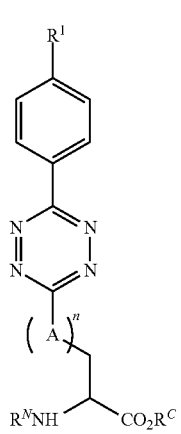

(VI)

or a stereoisomer or salt thereof.

As noted above, in one embodiment, the invention provides a tetrazine amino acid of formula (V) with n=0 and the invention provides a tetrazine amino acid having formula (VII):

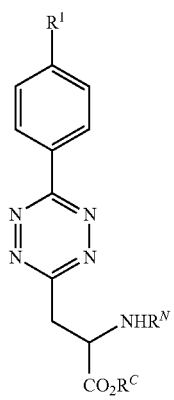

(VII)

or a stereoisomer or salt thereof.

In another embodiment, the invention provides a tetrazine amino acid of formula (V) with A as 1,4-phenylene (n=1) and the invention provides a tetrazine amino acid having formula (VIII):

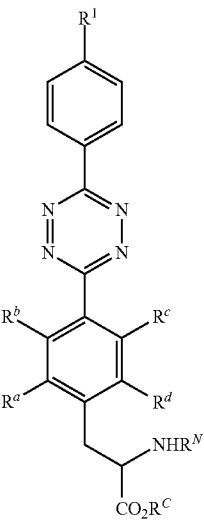

(VIII)

or a stereoisomer or salt thereof.

In formula (VIII), $R^a$, $R^b$, $R^c$, and $R^d$ are independently selected from hydrogen, C1-C3 alkyl (e.g., methyl), C1-C3 haloalkyl (e.g., trifluoromethyl), C1-C3 alkoxy (e.g., methoxy), and halo (e.g., fluoro, chloro). In one embodiment, $R^a$, $R^b$, $R^c$, and $R^d$ are hydrogen. In another embodiment, $R^a$, $R^b$, and $R^d$ are hydrogen. In a further embodiment, $R^a$ and $R^d$ are hydrogen.

In a further embodiment, the invention provides a tetrazine amino acid of formula (V) with A as 1,3-phenylene (n=1) and the invention provides a tetrazine amino acid having formula (IX):

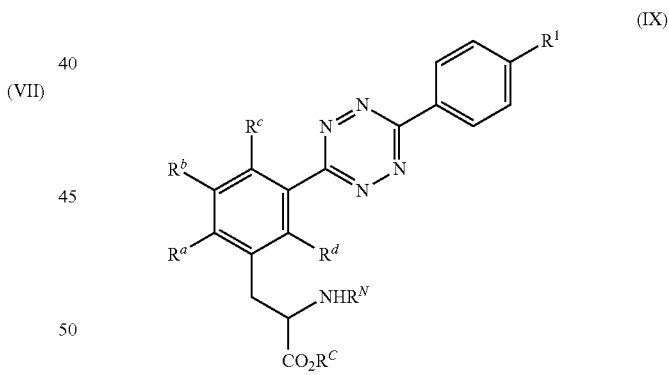

(IX)

or a stereoisomer or salt thereof.

In formula (IX), $R^a$, $R^b$, $R^c$, and $R^d$ are independently selected from hydrogen, C1-C3 alkyl (e.g., methyl), C1-C3 haloalkyl (e.g., trifluoromethyl), C1-C3 alkoxy (e.g., methoxy), and halo (e.g., fluoro, chloro). In one embodiment, $R^a$, $R^b$, $R^c$, and $R^d$ are hydrogen. In another embodiment, $R^a$, $R^b$, and $R^d$ are hydrogen. In a further embodiment, $R^a$ and $R^d$ are hydrogen.

In certain embodiments, the compounds of the invention are amino acids and maybe exist in neutral (e.g., —$NH_2$ and —$CO_2H$) or ionic form (e.g., —$NH_3^+$ and —$CO_2^-$) depending on the pH of the environment. It will be appreciated that the compounds of the invention include a chiral carbon center and that the compounds of the invention can take the form of a single stereoisomer (e.g., L or D isomer) or a mixture of stereoisomers (e.g., a racemic mixture or other mixture). It will be appreciated that the individual stereoisomers and mixtures of isomers are useful in methods of the invention for incorporating tetrazine-containing residues into proteins and polypeptides.

The tetrazine non-canonical amino acids of formulae (V)-(IX) are useful in the methods of the invention for genetically encoding a polypeptide of interest.

The following is a description of a representative tetrazine amino acid labeling reagent of the invention, its genetic encoding to provide a modified protein, and bioorthogonal ligation using the protein containing the tetrazine-containing amino acid.

To overcome the shortcomings of the tetrazine amino acids known in the art, and to push the limits of in vivo bioorthogonal reaction rates, tetrazine amino acids (referred to herein as "Tet-v2.0" and "Tet-v3.0" or "Tet2.0" and "Tet3.0") were generated using robust synthetic routes. Tet-v2.0 and Tet-v3.0 were genetically incorporated into proteins and the reactivity of Tet-v2.0-GFP and Tet-v3.0-GFP was characterized to demonstrate utility as an ideal bioorthogonal ligation.

Removing the stabilizing effects of the electron donating amine linkage increased the tetrazine reaction rate and prevented hydrolysis. Using a nickel triflate catalyst for generating tetrazines from nitriles, 4-(6-methyl-s-tetrazin-3-yl)phenylalanine (Tet-v2.0) and 3-(6-methyl-s-tetrazin-3-yl) phenylalanine (Tet-v3.0) were produced in two steps with a 57% yield from commercially available starting materials (see FIG. 4 and FIG. 11).

In order to genetically incorporate Tet-v2.0 into proteins and test its in vivo activity with sTCO (see FIG. 1B), an orthogonal *Methanococcus jannaschii* (Mj) tyrosyl tRNA synthetase (RS)/tRNA$_{CUA}$ pair capable of incorporating Tet-v2.0 in *E. coli* was evolved (see Example 2). RS plasmids from surviving clones were transformed into cells with a plasmid containing a GFP gene interrupted with an amber codon. Ninety-six (96) colonies were assessed for Tet-v2.0-dependent expression of GFP. The top seven performing clones showed significant GFP-Tet-v2.0 expression in the presence of Tet-v2.0 and no detectable GFP fluorescence over background in the absence of Tet-v2.0 (see FIG. 5). Sequencing revealed that all seven RS sequences were unique (see Table 2).

In order to genetically incorporate Tet-v3.0 into proteins (see FIG. 11), an orthogonal *Methanosarcina Barkeri* (Mb) pyrrolysyl tRNA synthetase (RS)/tRNA$_{CUA}$ pair capable of incorporating Tet-v3.0 in *E. coli* was evolved (see Example 2). RS plasmids from surviving clones were transformed into cells with a plasmid containing a GFP gene interrupted with an amber codon. Ninety-six (96) colonies were assessed for Tet-v3.0-dependent expression of GFP. The top seven performing clones showed significant GFP-Tet-v3.0 expression in the presence of Tet-v3.0 and limited detectable GFP fluorescence over background in the absence of Tet-v3.0 (see FIG. 5). Sequencing revealed that all seven RS sequences were unique (see Table 3).

Figure 1C:
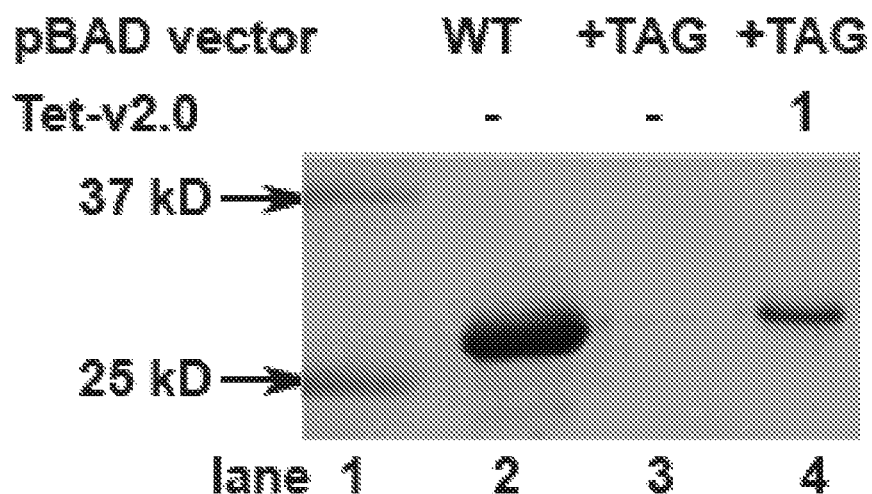

To facilitate robust expression of site-specifically encoded Tet-v2.0 containing proteins, the top performing Tet-RS was cloned into a pDule vector that contains one copy of Mj tRNA$_{CUA}$ to create pDule-Tet2.0. Expression of a GFP gene interrupted by an amber codon at site 150 in the presence of pDule-Tet2.0 was efficient and dependent on the presence of Tet-v2.0 (see FIG. 1C). Using 1 mM Tet-v2.0, 13.0 mg of GFP-Tet-v2.0 was purified per liter of media, while GFP-wt yielded 161 mg/L under similar conditions (no GFP is produced in the absence of Tet-v2.0). To demonstrate that Tet-v2.0 can be stably incorporated into recombinant proteins using pDule-Tet2.0, the masses of GFP-Tet-v2.0 to GFP-wt were compared using ESI-Q mass analysis. The native GFP-wt has the expected mass of 27827±1 Da and GFP-Tet-v2.0 exhibits the expected mass increase to 27955±1 Da verifying that Tet-v2.0 is incorporated at a single site (See FIG. 1E). Overall, the results of protein expression, MS analysis, and SDS PAGE demonstrated the cellular stability and efficient, high fidelity incorporation of Tet-v2.0 into proteins using a pDule system.

Figure 1D:
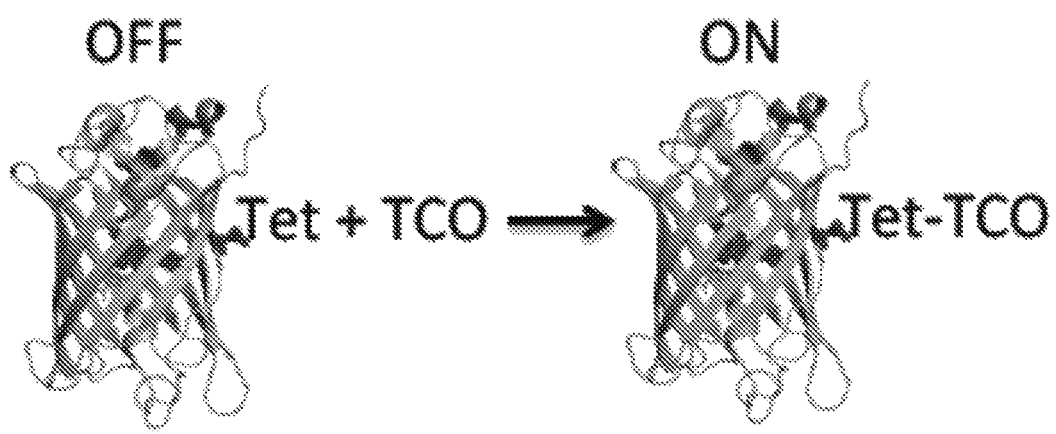
Figure 1E:
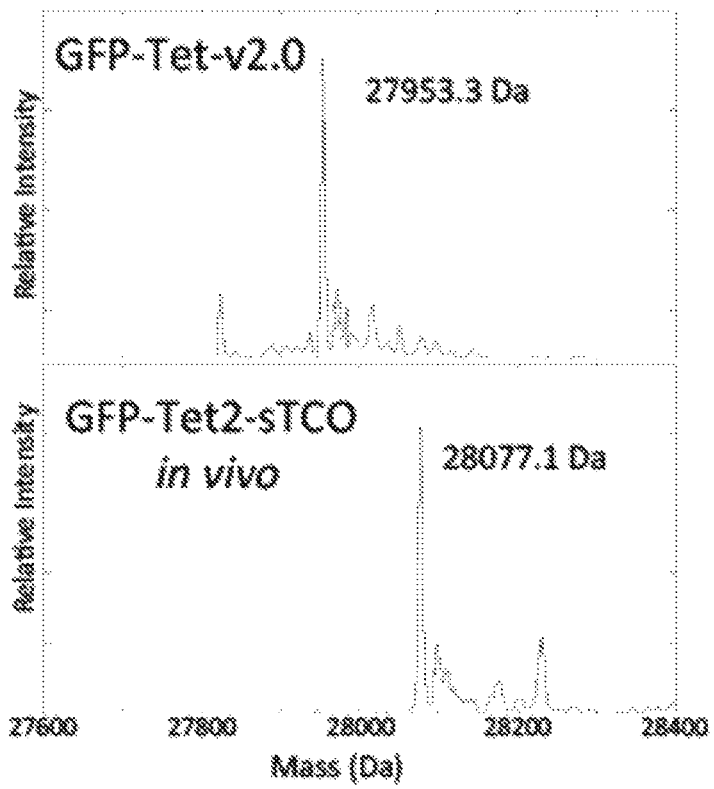

Previously tetrazine amino acids were shown quench GFP fluorescence when encoded close to its chromophore, and fluorescence returns when reacted with TCO-labels (see FIG. 1D). This increase in fluorescence of GFP-Tet-v2.0 upon reaction enables quantification of labeling reactions and reaction rates in vitro and in vivo. Incubating GFP-Tet-v2.0 (1.25 µM) with 13 µM sTCO in PBS buffer shows a complete return of fluorescence in less than 10 seconds indicating GFP-Tet-v2.0-TCO was formed. ESI-Q of the desalted reaction mixture confirmed the quantitative conversion of GFP-Tet-v2.0 (expected 27954.5 Da; observed 27955.7±1 Da) into GFP-Tet-sTCO (expected 28078.7 Da; observed 28078.3±1 Da). This demonstrates the reaction between GFP-Tet-v2.0 and sTCO is quantitative in vitro.

To determine if this bioorthogonal ligation is also quantitative in cellulo, *E. coli* cells containing expressed GFP-Tet-v2.0 were incubated with 3.3 µM sTCO in PBS buffer at room temperature. Complete fluorescence returned in less than 10 seconds, indicating that GFP-Tet-sTCO had been formed. After incubation at room temperature for 24 hrs the cells were lysed, GFP-Tet-v2.0-His$_6$ was affinity purified and analyzed by ESI-Q MS. The resulting molecular mass matched GFP-Tet-sTCO (see FIG. 1E). This verifies that the in cellulo reaction is facile, quantitative, and the conjugated product is stable.

Figure 2A:
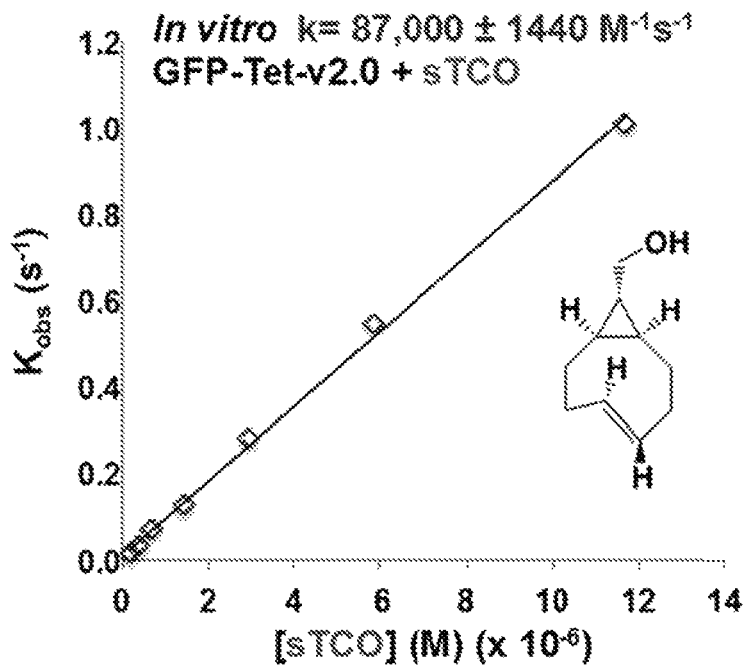
FIGS. 2A and 2B compare in vitro and in cellulo rate constant determinations for reaction of GFP-Tet-v2.0 with sTCO.

An ideal bioorthogonal reaction requires an in cellulo rate of >$10^4$ $M^{-1}s^{-1}$ to complete in seconds to minutes at biological concentrations (µM to nM) of both biomolecule and label. To determine if reactions of Tet-v2.0 on a protein are fast enough to meet these rates, the reaction of GFP-Tet-v2.0 with sTCO was measured. The kinetics of the reaction were performed under pseudo-first-order conditions as verified by a single exponential fit for return of product fluorescence. The in vitro second order rate constant for GFP-Tet-v2.0 with sTCO is 87,000±1440 $M^{-1}s^{-1}$ (FIG. 2A). Surprisingly the site-specific Tet-v2.0-protein reaction with sTCO is two orders of magnitude faster than Tet-v1.0 (also referred to herein as "Tet," see FIG. 1A).

Figure 2B:
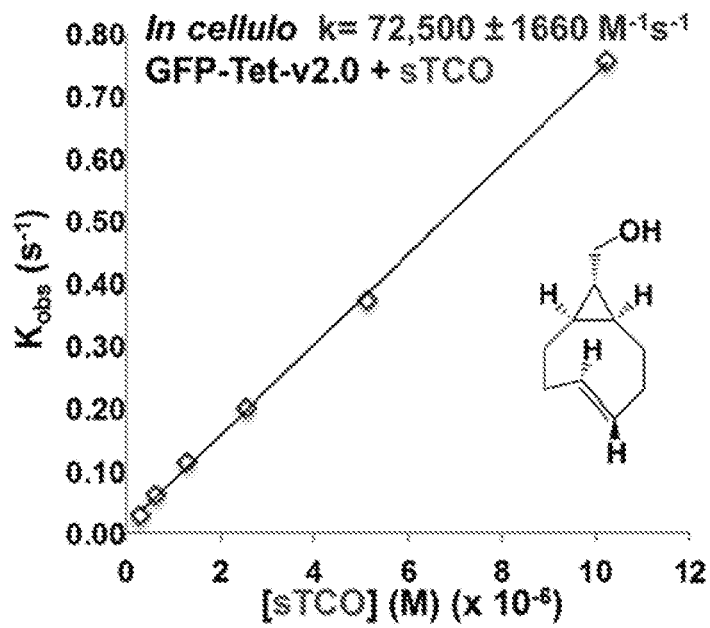

To date, no bioorthogonal rate constants greater than $10^3$ $M^{-1}s^{-1}$ have been measured in cellulo. To determine the rate constant for this reaction inside live cells, *E. coli* expressing GFP-Tet-v2.0 was washed, resuspended in PBS buffer, and reacted with sTCO. The in cellulo bimolecular rate constant for this reaction is 72,500±1660 $M^{-1}s^{-1}$ and is fast enough to meet the needs of the ideal bioorthogonal ligation (see FIG. 2B). This in cellulo reaction rate will allow 95% labeling in less than a minute at 1 µM Tet-v2.0-protein and sTCO label. The short reaction time is enabled by a $t_{1/2}$ of 12-14 seconds. Ideal bioorthogonal reaction rates eliminate the need for time consuming washing steps prior to cell analysis and allow for immediate monitoring of cellular events since the labeling reaction is rapidly completed at stoichiometric concentrations of label.

Figure 3A:
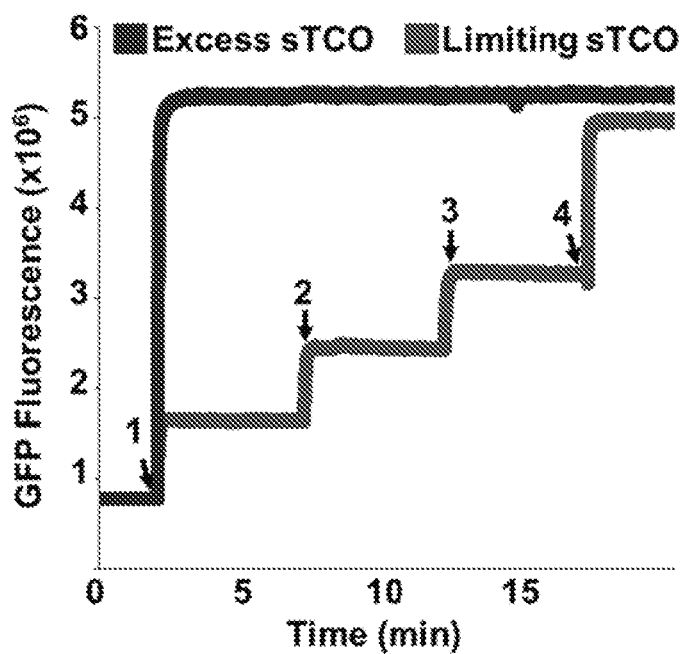
FIGS. 3A-3D illustrate sub-stoichiometric characterization of GFP-Tet-v2.0 reaction with sTCO.
Figure 3B:
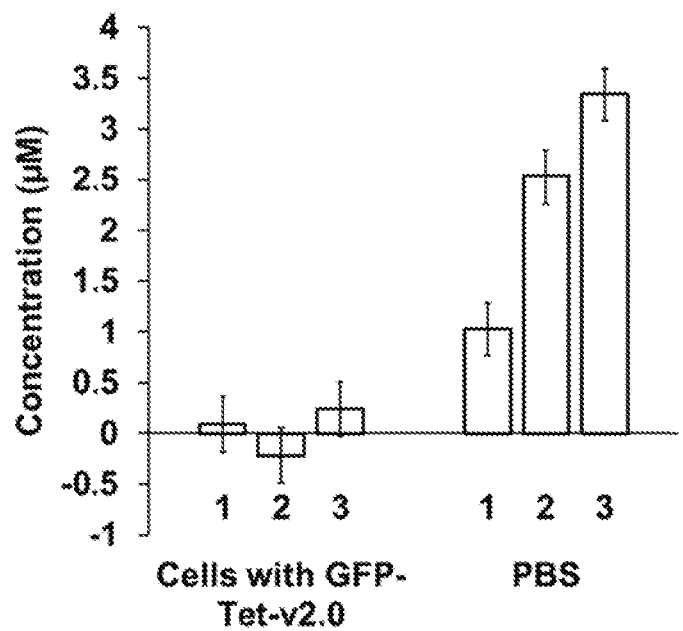

To verify that the Tet-v2.0-protein/sTCO reaction rate is sufficient to effectively use sub-stoichiometric concentrations of label in live cells, the amount of sTCO added to *E.* coli cells containing GFP-Tet-v2.0 was reduced (See FIG. 3A). For comparison, traditional labeling conditions using an excess of sTCO show complete labeling in about 1 minute. Four additions of sTCO to cells containing GFP-Tet-v2.0 are also shown. The first three sTCO additions are $\frac{1}{5}^{th}$ the molar amount of GFP-Tet-v2.0 and the fourth addition is an excess of sTCO. The sub-stoichiometric labeling reproducibly showed complete labeling within 1 minute. When reacting sTCO with Tet-v2.0-protein sub-stoichiometrically in vivo, all sTCO-label should bind to Tet-v2.0-protein in vivo leaving none in extracellular solution. To verify this, samples of the solution for sTCO were assayed after fluorescence plateau from each sTCO addition (points 1-4 in FIG. 3A). Following sub-stoichiometric additions of sTCO, (points 1-3) negligible concentrations of sTCO were detected (see FIG. 3B). This contrasts with the stepwise increase in concentration when identical amounts of sTCO were added to PBS buffer in the absence of Tet-v2.0-protein. This feature of Tet-v2.0 would eliminate the need for a washout step when labeling protein in vivo if sTCO is conjugated to a fluorescent dye.

Figure 3C:
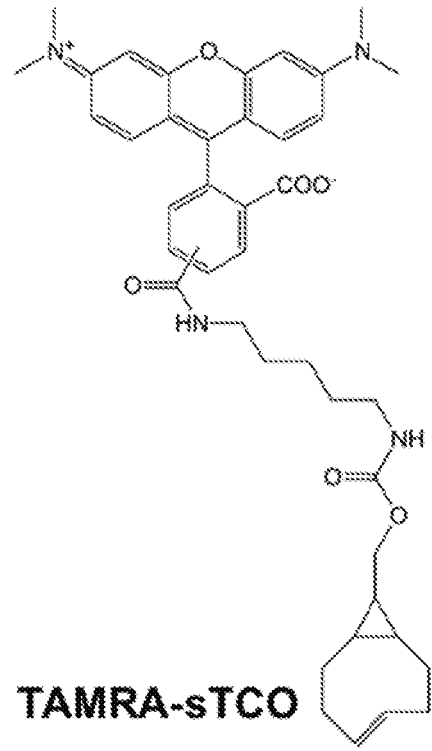
Figure 3D:
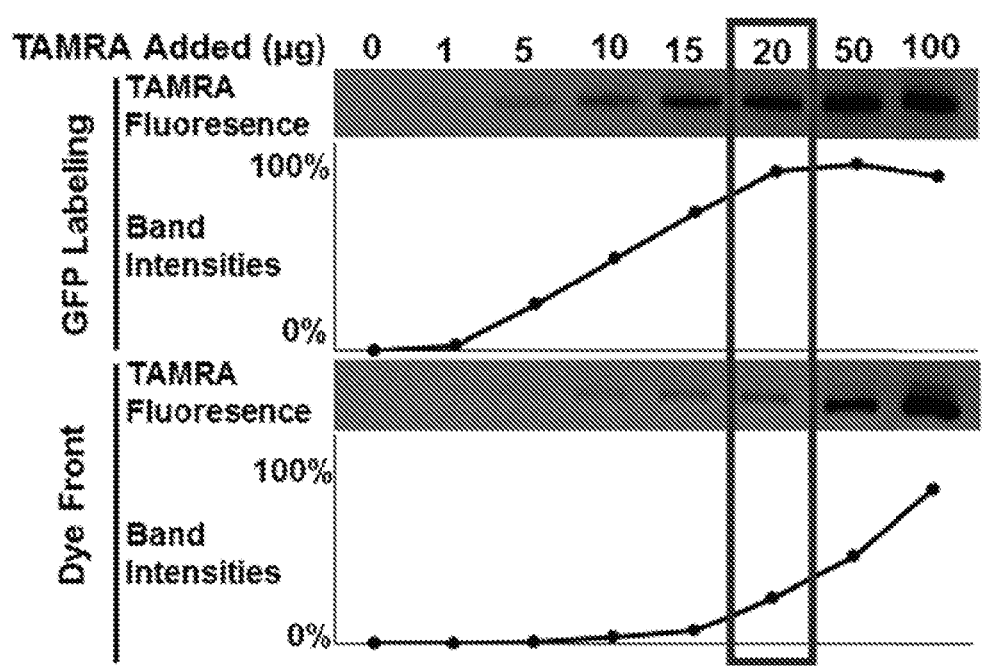

To demonstrate that the washout step of a conjugated dye is nonessential when reaction rates of this magnitude are employed, a tetramethyl-rhodamine (TAMRA)-linked sTCO label was synthesized. TAMRA-sTCO was incubated with purified GFP-Tet-v2.0 in vitro and analysis by SDS-PAGE demonstrates a reaction between GFP-Tet-v2.0 and TAMRA-sTCO. Fluorescence imaging of the gel shows a band present only when TAMRA-sTCO and GFP-Tet-v2.0 were present. Labeling of protein in living cells with low concentrations of dyes is often slow and incomplete because dye diffusion into cells at these concentrations and timescales is limiting. Conjugated TAMRA dyes have previously been shown to enter mammalian cells, but slower bioorthogonal reaction rates required higher concentrations of TAMRA-labels and longer reaction times. Improved fluorescent dyes are needed to overcome the rate limiting steps of cellular uptake with fast bioorthogonal ligations. To circumvent this problem for this sub-stoichiometric demonstration, TAMRA-sTCO was reacted with E. coli lysate containing GFP-Tet-v2.0 at quantities of TAMRA-sTCO ranging from 5-500% of the total GFP-Tet-v2.0 concentration. The lysate was analyzed by SDS-PAGE and the resulting two rhodamine fluorescence bands; an approximately 27 kDa band corresponding to GFP-Tet-v2.0 conjugated to TAMRA-sTCO and a dye front migrating band corresponding to unreacted TAMRA-sTCO (FIG. 3C). As expected, the fluorescent TAMRA-GFP band increases in intensity as the amount of added TAMRA-sTCO increases incrementally until the intensity plateaus at about 100% of GFP-Tet-v2.0 (20 µg TAMRA-sTCO). While TAMRA-sTCO was added to the full lysate, it does not accumulate at the gel's dye front until GFP-Tet-v2.0 is completely labeled. After this point TAMRA fluorescence at the dye front increases rapidly with the amount of TAMRA-sTCO added as would be expected of a reaction with excess label. The low background signal detected at the dye front in sub-stoichiometric reactions likely results from incomplete purification of TAMRA-sTCO from isomerized cyclopropane-fused cis-cyclooctene-linked-TAMRA and unreacted TAMRA starting materials. Together these data indicate that efficient sub-stoichiometric reactions of protein-Tet-v2.0 with TAMRA-sTCO are possible in the presence of cellular components.

In summary, the invention provides an in cellulo bioorthogonal reaction based on genetically encoding of a tetrazine amino acid that meets the demands of an ideal bioorthogonal ligation. GFP-Tet-v2.0 does not cross-react with any cellular components or degrades in the cellular environment as demonstrated with mass spectrometry. Tet-v2.0 is small enough that it does not perturb the structure of GFP when positioned at site 150. The on-protein bimolecular rate constant of $87,000 \pm 1440$ $M^{-1}s^{-1}$ gives this robust reaction the speed it needs to compete with cellular processes.

The same attributes that make this reaction ideal, open the door to a variety of applications. The bimolecular rate constant is a significant improvement over previous in vivo biorthogonal ligations. This rate affords complete labeling of Tet-v2.0-protein in minutes even with low concentration of the sTCO label or concentrations below that of the protein being labeled. A sub-stoichiometric in vivo biorthogonal ligation has applications towards drug-antibody conjugates where it could minimize the clearance time of drugs or radioactive labels targeted to specific cells. Additionally, the high rate combined with in cellulo reactivity enables one to probe various pathways on a biologically relevant time scale. The invention provides the first demonstration of a bioorthogonal ligation with sufficient selectivity and a high enough reaction rate to sub-stoichiometrically label proteins in live cells, thereby eliminating the need to wash out excess label prior to imaging. At this point, the ability of the fluorescent probe to enter the cytosol is the limiting factor to in cellulo sub-stoichiometric labeling. Combining the flexibility of genetic code expansion with the diversity of labels in live cells allows for numerous creative applications that modulate cellular function.

The present invention provides a significantly improved tetrazine-containing amino acid that has been genetically encoded with an evolved amino acyl tRNA synthetase/tRNA$_{(CUA)}$ pair. The protein containing the tetrazine-containing amino acid reacts selectively with cyclopropane-fused trans cyclooctene (sTCO) in cellulo with a bimolecular rate constant of $72,500 \pm 1660$ $M^{-1}s^{-1}$, but does not react with other cellular components. This bioorthogonal ligation of the protein reacts in cellulo with sub-stoichiometric amounts of sTCO-label rapidly enough to remove the labeling reagent from media in minutes, thereby eliminating the need to washout label. This ideal bioorthogonal reaction will enable the monitoring of a larger window of cellular processes in real time.

The following examples are provided for the purpose of illustrating, not limiting the invention.

EXAMPLES

Example 1

The Preparation of a Representative Tetrazine Amino Acid

Figure 4:
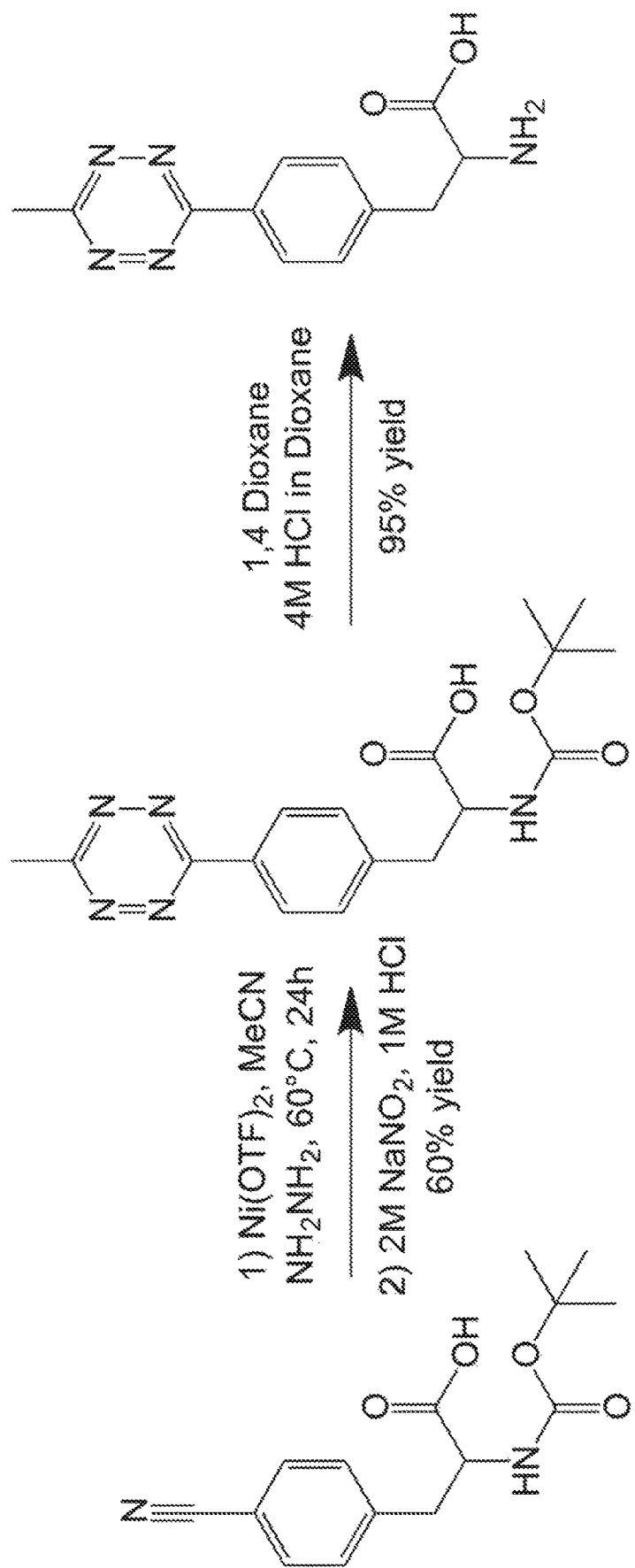
FIG. 4 is a schematic illustration of the synthesis of a representative tetrazine amino acid of the invention, 4-(6-methyl-s-tetrazin-3-yl)phenylalanine (Tet-v2.0).

In this example, the preparation of a representative tetrazine amino acid of the invention, 4-(6-methyl-s-tetrazin-3-yl)phenylalanine (Tet-v2.0), is described. The preparation is illustrated in FIG. 4. In a similar method 4-(6-ethyl-s-tetrazin-3-yl)phenylalanine (Tet-v2.1), 4-(6-isoproyl-s-tetrazin-3-yl)phenylalanine (Tet-v2.2), 4-(6-butyl-s-tetrazin-3-yl)phenylalanine (Tet-v2.3) were prepared shown in FIG. 12A.

N-(tert-Butoxycarbonyl)-4-(6-methyl-1,2,4,5-tetrazin-3-yl)-L-phenylalanine (2)

A dry, 75 mL heavy walled reaction tube was equipped with a stir bar and was charged with 1 (500 mg, 1.72 mmol), Ni(OTf)$_2$ (307.3 mg, 0.86 mmol), and acetonitrile (1.8 mL, 34.4 mmol). The flask was purged with argon for 20 minutes. Anhydrous hydrazine was added to the mixture (2.7 mL, 86 mmol), the tube was sealed, and the reaction mixture was heated to 60° C. for 24 hr. The reaction was allowed to cool to room temperature and slowly opened to air. Sodium nitrite (2 M, 8 mL) was added to the flask and the contents were cooled to 0° C. 1 N HCl was added slowly until gas evolution ceased and the pH of the mixture was acidic (about 3). The mixture was then diluted with EtOAc and the layers separated. The aqueous layer was extracted with EtOAc (2×). The combined the organic layers were washed with brine, dried with Na$_2$SO$_4$, and concentrated under reduced pressure. Silica gel flash column chromatography (50% ethyl acetate in hexanes with 1% acetic acid) yielded 370 mg of 2 (1.03 mmol, 60%) in the form of a red oil. R$_f$=0.33 in 50% ethyl acetate in hexanes with 1% acetic acid; $^1$H NMR (400 MHz, CDCl$_3$) δ 8.53 (d, 2H), 7.39 (d, 2H), 5.0 (d, 1H), 4.66 (m, 1H), 3.37-3.15 (dd, 2H), 3.09 (s, 3H), 1.39 (s, 9H).

4-(6-methyl-1,2,4,5-tetrazin-3-yl)-L-phenylalanine hydrochloride salt (Tet-v2.0)

A dry 100 mL flask 2 (480 mg, 1.34 mmol) was charged with and then purged with argon for 10 minutes. This oil was dissolved in 4 mL of 1,4-dioxane then 4 M HCl in 1,4 dioxane (6 mL) was added over 20 seconds. The reaction was allowed to stir for 12 hrs at room temperature. The reaction was concentrated under reduced pressure, then dissolved in EtOAc, and concentrated down to a red powder. The red solid was washed with pentanes and collected via filtration to afford 377 mg of Tet-v2.0 (1.18 mmol, 95%) of a red solid. $^1$H NMR (400 MHz, CD$_3$OD) δ 8.48 (d, 2H), 7.48 (d, 2H), 4.29 (t, 1H), 3.41-3.20 (m, 2H), 2.97 (s, 3H).

Example 2

The Preparation of a Representative Tetrazine Amino Acid

Figure 11:
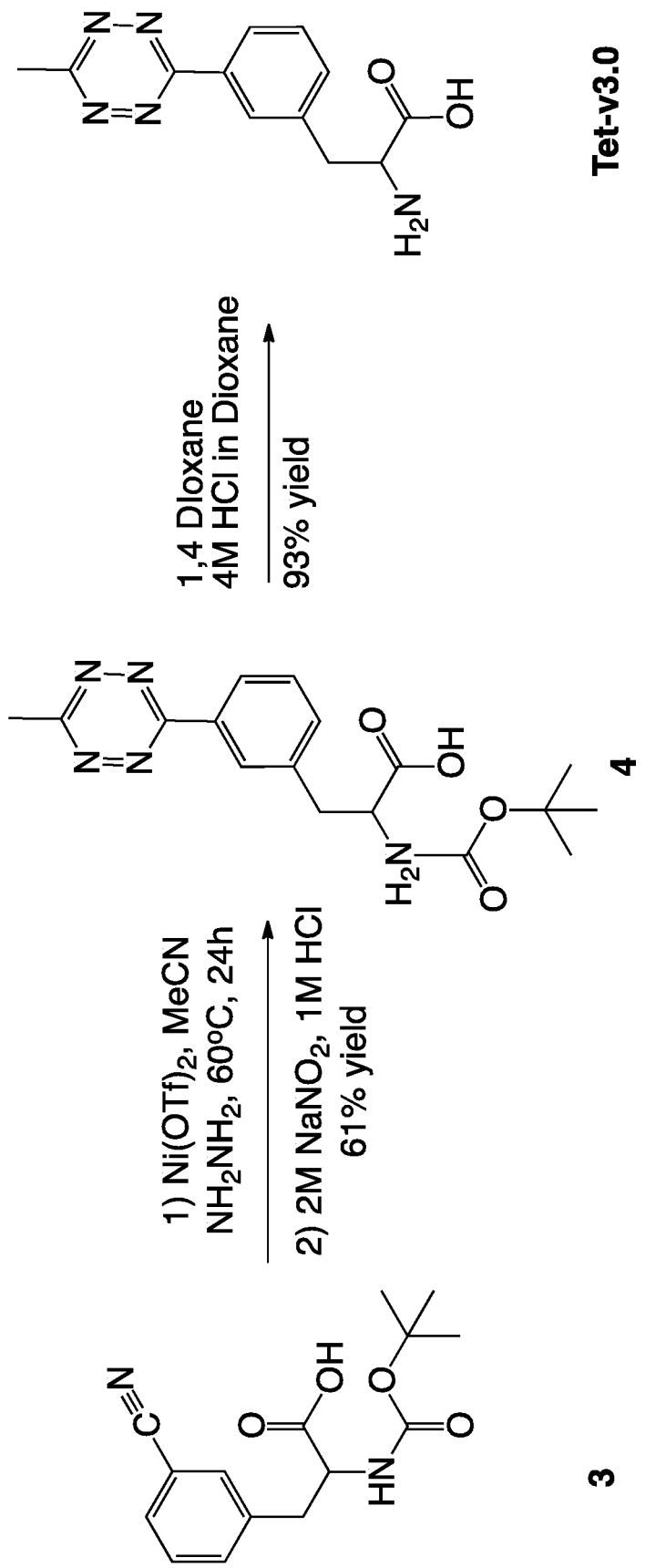
FIG. 11 is a schematic illustration of the synthesis of a representative tetrazine amino acid of the invention, 3-(6-methyl-s-tetrazin-3-yl)phenylalanine (Tet-v3.0).

In this example, the preparation of a representative tetrazine amino acid of the invention, 3-(6-methyl-s-tetrazin-3-yl)phenylalanine (Tet-v3.0), is described. The preparation is illustrated in FIG. 11.

N-(tert-Butoxycarbonyl)-3-(6-methyl-1,2,4,5-tetrazin-3-yl)-L-phenylalanine (4)

A dry, 75 mL heavy walled reaction tube was equipped with a stir bar and was charged with 3 (150 mg, 0.52 mmol), Ni(OTf)$_2$ (91.3 mg, 0.26 mmol), and acetonitrile (0.27 mL, 5.2 mmol). The flask was purged with argon for 20 minutes. Anhydrous hydrazine was added to the mixture (0.82 mL, 26 mmol), the tube was sealed, and the reaction mixture was heated to 60° C. for 24 hr. The reaction was allowed to cool to room temperature and slowly opened to air. Sodium nitrite (2 M, 5.2 mL) was added to the flask. The reaction mixture was diluted with 50 mL water. Subsequently, the organic byproducts were exacted with EtOAc (3×), combined, and washed with water (2×) to regain any lost product. The aqueous layers were combined and the contents were cooled to 0° C. 1 N HCl was added slowly until gas evolution ceased and the pH of the mixture was acidic (about 3). The mixture was then diluted with EtOAc and the layers separated. The aqueous layer was extracted with EtOAc (2×). The combined organic layers were washed with brine, dried with Na$_2$SO$_4$, and concentrated under reduced pressure. Silica gel flash column chromatography (50% ethyl acetate in hexanes with 1% acetic acid) yielded 113 mg of 4 (0.325 mmol, 61%) in the form of a red oil. R$_f$=0.33 in 50% ethyl acetate in hexanes with 1% acetic acid. $^1$H NMR (400 MHz, CDCl$_3$) δ 8.44 (t, 2H), 7.51 (m, 2H), 5.19 (d, 1H), 4.73 (d, 1H), 3.38-3.24 (dd, 2H), 3.11 (s, 3H), 1.42 (s, 9H).

4-(6-methyl-1,2,4,5-tetrazin-3-yl)-L-phenylalanine hydrochloride salt (Tet-v3.0)

A dry 100 mL flask containing 4 (110 mg, 0.317 mmol) was charged with and then purged with argon for 10 minutes. This oil was dissolved in 2 mL of 1,4 dioxane then 4 M HCl in 1,4 dioxane (3 mL) was added over 20 seconds. The reaction was allowed to stir for 12 hours at room temperature. The reaction was concentrated under reduced pressure, then dissolved in EtOAc, and concentrated down to a red powder. The red solid was washed with pentanes and collected via filtration to afford 89.2 mg of Tet-v3.0 (0.310 mmol, 93%). $^1$H NMR (400 MHz, D$_2$O) δ 8.38 (t, 2H), 7.69 (m, 2H), 4.23 (t, 1H), 3.50-3.32 (m, 2H), 3.10 (s, 3H).

Example 3

Selection of Aminoacyl-tRNA Synthetases Specific for a Representative Tetrazine Amino Acid and Bioorthogonal Labeling: Tet-v2.0-Methyl In this example the selection of aminoacyl-tRNA synthetases specific for a representative tetrazine amino acid, 4-(6-methyl-s-tetrazin-3-yl)phenylalanine (Tet-v2.0-methyl or Tet2.0-methyl), and bioorthogonal labeling is described.

TABLE 1

Components for autoinducing and non-inducing mediums for final volume of 500 mL.

| Component | A) Autoinduction medium | B) Non-inducing medium | C) Autoinducing plates |
|---|---|---|---|
| 5% aspartate, pH 7.5 | 25 mL | 25 mL | 25 mL |
| 10% glycerol | 25 mL | — | 25 mL |
| 25 × 18 amino acid mix | 20 mL | 20 mL | 20 mL |
| 50 × M | 10 mL | 10 mL | 10 mL |
| leucine (4 mg/mL), pH 7.5 | 5 mL | 5 mL | 5 mL |
| 20% arabinose | 1.25 mL | — | 1.25 mL |
| 1M MgSO$_4$ | 1 mL | 1 mL | 1 mL |
| 40% glucose | 625 μL | 6.25 mL | 125 μL |
| Trace metals | 100 μL | 100 μL | 100 μL |

Selection of Aminoacyl-tRNA Synthetases Specific for Tet2.0

The library of aminoacyl-tRNA synthetases was encoded on a kanamycin (Kn) resistant plasmid (pBK, 3000 bp) under control of the constitutive *Escherichia coli* GlnRS promoter and terminator. The aminoacyl synthetase library (3D-Lib) was randomized as follows: Leu65, His70, Gln155, and Ile159 were randomized to all 20 natural amino acids; Tyr32 was randomized to 15 natural amino acids (less Trp, Phe, Tyr, Cys, and Ile); Asp158 was restricted to Gly, Ser, or Val; Leu162 was restricted to Lys, Ser, Leu, His, and Glu; and Phe108 and Gln109 were restricted to the pairs Trp-Met, Ala-Asp, Ser-Lys, Arg-Glu, Arg-Pro, Ser-His, or Phe-Gln. The library plasmid, pBK-3D-Lib, was moved between cells containing a positive selection plasmid (pCG) and cells containing a negative selection plasmid (pNEG).

The positive selection plasmid, pCG (10000 bp), encodes a mutant *Methanococcus jannaschii* (Mj) tyrosyl-tRNA$_{CUA}$, an amber codon-disrupted chloramphenicol acetyltransferase, an amber codon-disrupted T7 RNA polymerase, a T7 promoter controlled green fluorescent protein gene, and the tetracycline (Tet) resistance marker. The negative selection plasmid, pNEG (7000 bp), encodes the mutant tyrosyl-tRNA$_{CUA}$, an amber codon-disrupted barnase gene under control of an arabinose promoter and rrnC terminator, and the ampicillin (Amp) resistance marker. pCG electrocompetent cells and pNEG electrocompetent cells were made from DH10B cells carrying the respective plasmids and stored in 100 µL aliquots at −80° C. for future rounds of selection.

The synthetase library in pBK-3D-Lib was transformed by electroporation into DH10B cells containing the positive selection plasmid, pCG. The resulting pCG/pBK-3D-Lib-containing cells were amplified in 1 L of 2×YT with 50 µg/mL Kn and 25 µg/mL Tet with shaking at 37° C. The cells were grown to saturation, then pelleted at 5525 ref, resuspended in 30 mL of 2×YT and 7.5 mL of 80% glycerol, and stored at −80° C. in 1 mL aliquots for use in the first round of selections.

For the positive selection, 2 mL of pCG/pBK-3D-Lib cells were thawed on ice before addition to 1.2 L of room temperature 2×YT media containing 50 µg/mL Kn and g/mL Tet. After incubation (11 h, 250 rpm, 37° C.), a 200 µL aliquot of these cells was plated on eleven 15 cm GMML-agar plates containing 50 µg/mL Kn, 25 µg/mL Tet, and 60 µg/mL chloramphenicol (Cm). The positive selection agar medium also contained 1 mM Tet amino acid. After spreading, the surface of the plates was allowed to dry completely before incubation (37° C., 15 h). To harvest the surviving library members from the plates, 10 mL of 2×YT (50 µg/mL Kn, 25 µg/mL Tet) was added to each plate. Colonies were scraped from the plate using a glass spreader. The resulting solution was incubated with shaking (60 min, 37° C.) to wash cells free of agar. The cells were then pelleted, and plasmid DNA was extracted. For the first positive selection a Qiagen midiprep kit was used to purify the plasmid DNA. For all other plasmid purification steps a Qiagen miniprep kit was used to purify the plasmid DNA. The smaller pBK-3D-Lib plasmid was separated from the larger pCG plasmid by agarose gel electrophoresis and extracted from the gel using the Qiagen gel extraction kit.

The purified pBK-3D-Lib was then transformed into pNEG-containing DH10B cells. A 100 µL sample of pNEG electrocompetent cells was transformed with 50 ng of purified pBK-3D-Lib DNA. Cells were rescued in 1 mL of SOC for 1 h (37° C., 250 rpm) and the entire 1 mL of rescue solution was plated on three 15 cm LB plates containing 100 µg/mL Amp, 50 µg/mL Kn, and 0.2% L-arabinose. Cells were collected from plates and pBK-3D-Lib plasmid DNA was isolated in the same manner as described above for positive selections.

In order to evaluate the success of the positive and negative selection based on variation in synthetase efficacy (as opposed to traditional survival/death results) the synthetases resulting from the selection rounds were tested with the pALS plasmid. This plasmid contains the sfGFP reporter with a TAG codon at residue 150 as well as tyrosyl-tRNA$_{CUA}$. When a pBK plasmid with a functional synthetase is transformed with the pALS plasmid and the cells are grown in the presence of the appropriate amino acid on autoinduction agar, sfGFP is expressed and the colonies are visibly green.

One microliter of each library resulting from the second positive and the second negative rounds of selection was transformed with 60 µL of pALS-containing DH10B cells. The cells were rescued for 1 hr in 1 mL of SOC (37° C., 250 rpm). A 250 µL and 50 µL of cells from each library were plated on autoinducing minimal media with µg/mL Kn, 50 µg/mL Tet, and 1 mM Tet2.0. Plates were grown at 37° C. for 24 hours and then grown on the bench top, at room temperature, for an additional 24 hours. Autoinducing agar plates were prepared by combining the reagents in Table 1C with an autoclaved solution of 40 g of agarose in 400 mL water. Sterile water was added to a final volume of 500 mL. Antibiotics were added to a final concentration of 25 µg/mL Tet and 50 µg/mL Kan.

A total of 96 visually green colonies were selected from the two 1 mM Tet-v2.0 plates and used to inoculate a 96-well plate containing 0.5 mL per well non-inducing minimal media (Table 1B, with sterile water added to a final volume of 500 mL) with 25 µg/mL Kn, 25 µg/mL Tet. After 24 hours of growth (37° C., 250 rpm), 5 µL of these non-inducing samples were used to inoculate 96-well plates with 0.5 mL autoinduction media (Table 1C, with sterile water added to a final volume of 500 mL) containing µg/mL Kn, 25 µg/mL Tet with and without 1 mM Tet-v2.0.

Fluorescence measurements of the cultures were collected 36 hours after inoculation using a BIOTEK® Synergy 2 Microplate Reader. The emission from 528 nm (20 nm bandwidth) was summed with excitation at 485 nm (20 nm bandwidth). Samples were prepared by diluting suspended cells directly from culture 2-fold with phosphate buffer saline (PBS). Seven expressions showed high efficiency with Tet-v2.0 and good fidelity without ncAA.

Fluorescence Analysis of Highest-Fluorescing Clones

Figure 5:
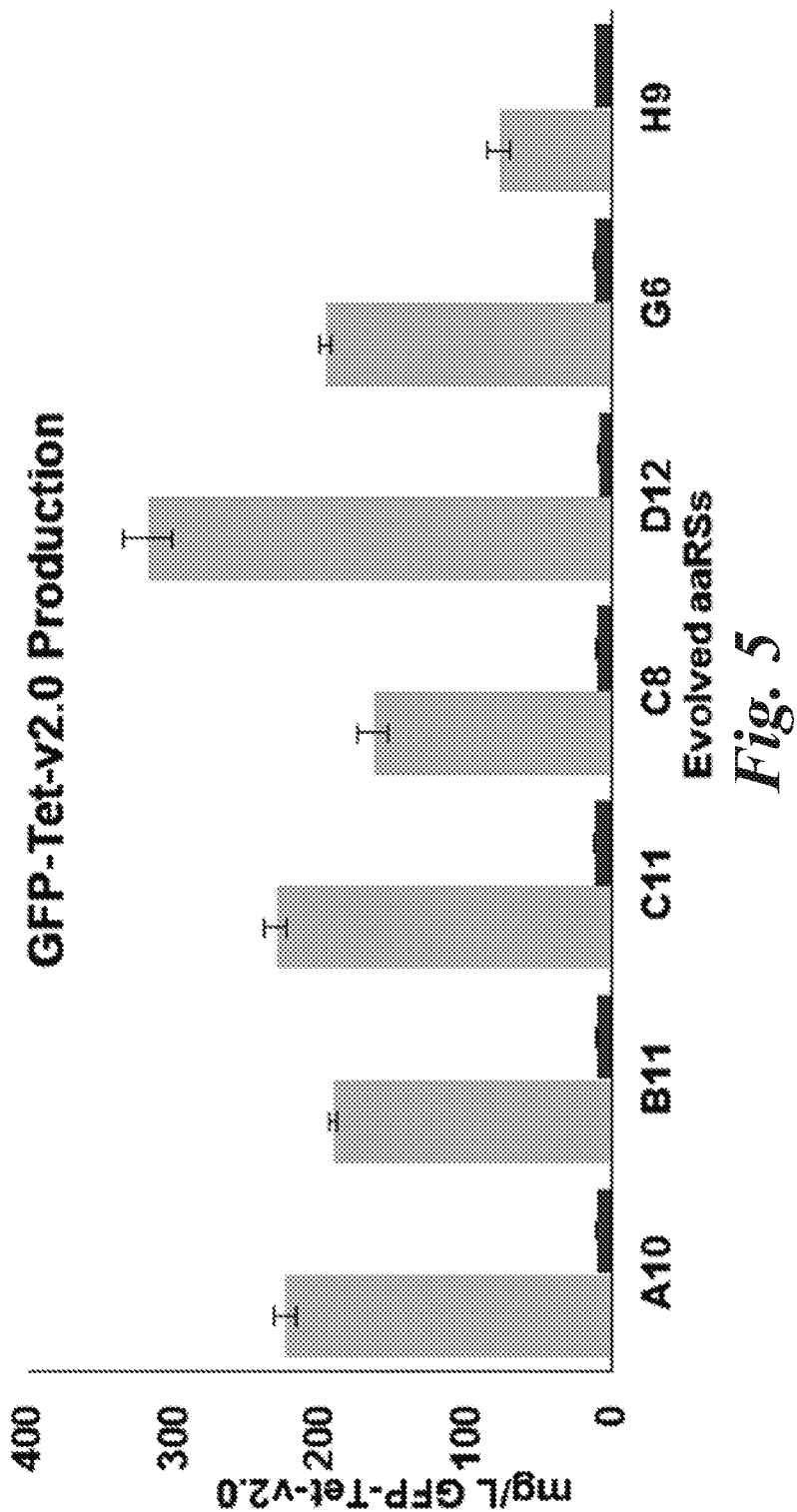
FIG. 5 compares fluorescence measurements of seven synthetases with GFP ncAA-reporter to determine relative efficiency and fidelity of selected synthetases for Tet-v2.0.
Figure 6:
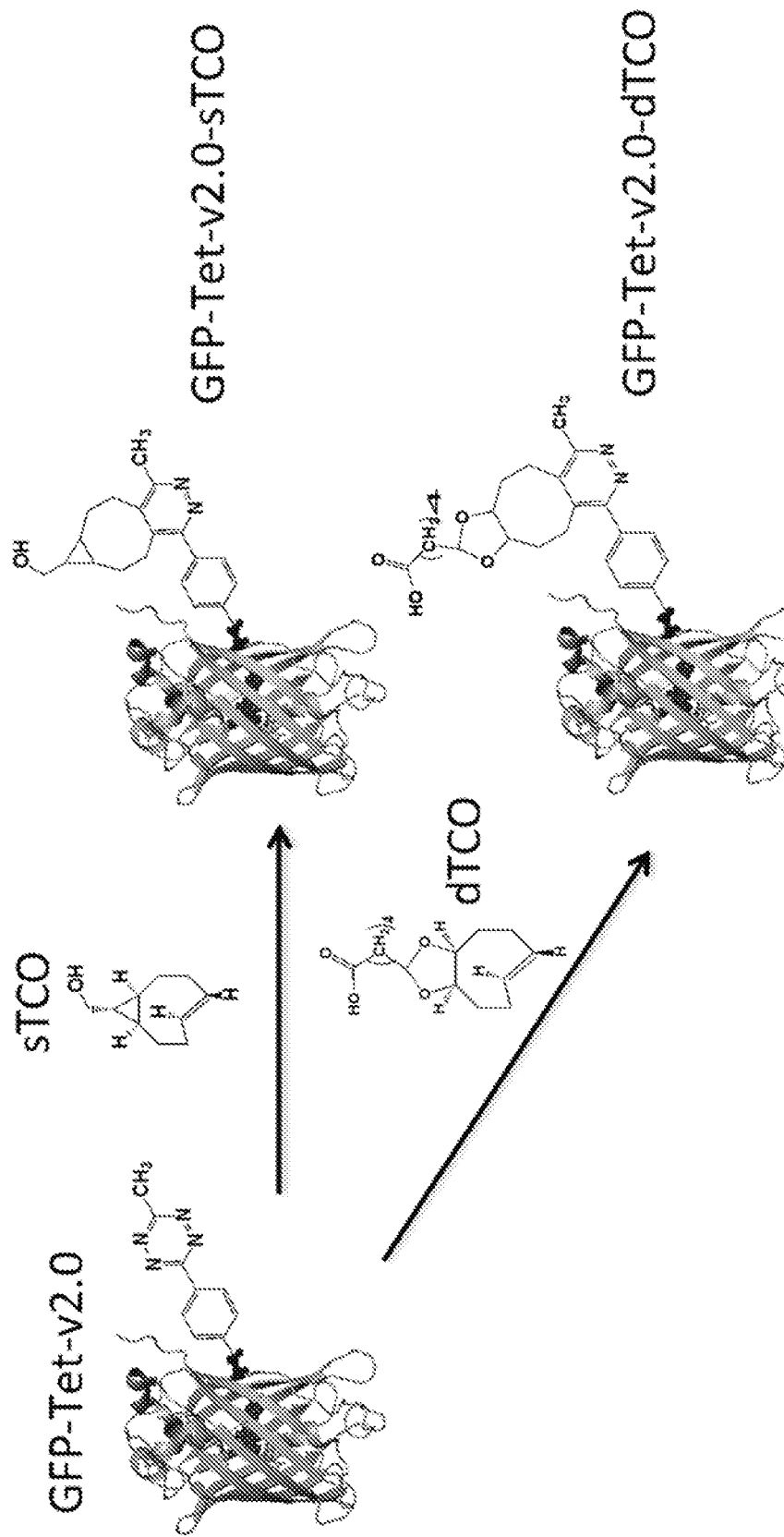
FIG. 6 is a schematic illustration of the reaction of GFP-Tet-v2.0 with sTCO and dTCO.

Non-inducing cultures (3 mL) with 25 µg/mL Kn and 25 µg/mL Tet were grown to saturation (37° C. with shaking at 250 rpm) from the top seven expressions in the 96 well plate analysis. Autoinduction cultures (5 mL) with 25 µg/mL Kn and 25 µg/mL Tet were inoculated with 30 µL of non-inducing cultures and grown with and without 1 mM Tet-v2.0 at 37° C. with shaking at 250 rpm. After approximately 40 hours, fluorescence was assessed. The results are compared in FIG. 5. In FIG. 5, gray represents colonies induced in media containing 1 mM Tet-v2.0 while black represents colonies induced in the absence of UAA. Expressions of 500 µL were grown for 36 hours before dilution of suspended cells directly from culture 2-fold with phosphate buffer saline (PBS). Fluorescence measurements were collected using a BIOTEK® Synergy 2 Microplate Reader.

Figure 12A:
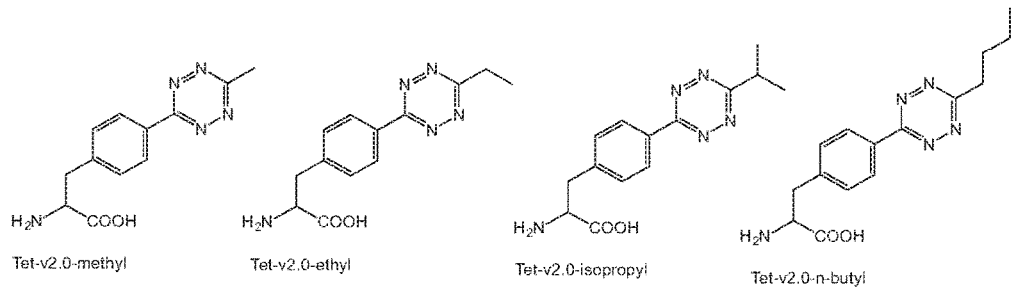
FIG. 12A illustrates representative tetrazine amino acids of the invention: 4-(6-methyl-s-tetrazin-3-yl)phenylalanine (Tet-v2.0-methyl), 4-(6-ethyl-s-tetrazin-3-yl)phenylalanine (Tet-v2.0-ethyl), 4-(6-isopropyl-s-tetrazin-3-yl)phenylalanine (Tet-v2.0-isopropyl), and 4-(6-butyl-s-tetrazin-3-yl) phenylalanine (Tet-v2.0-n-butyl).
Figure 12B:
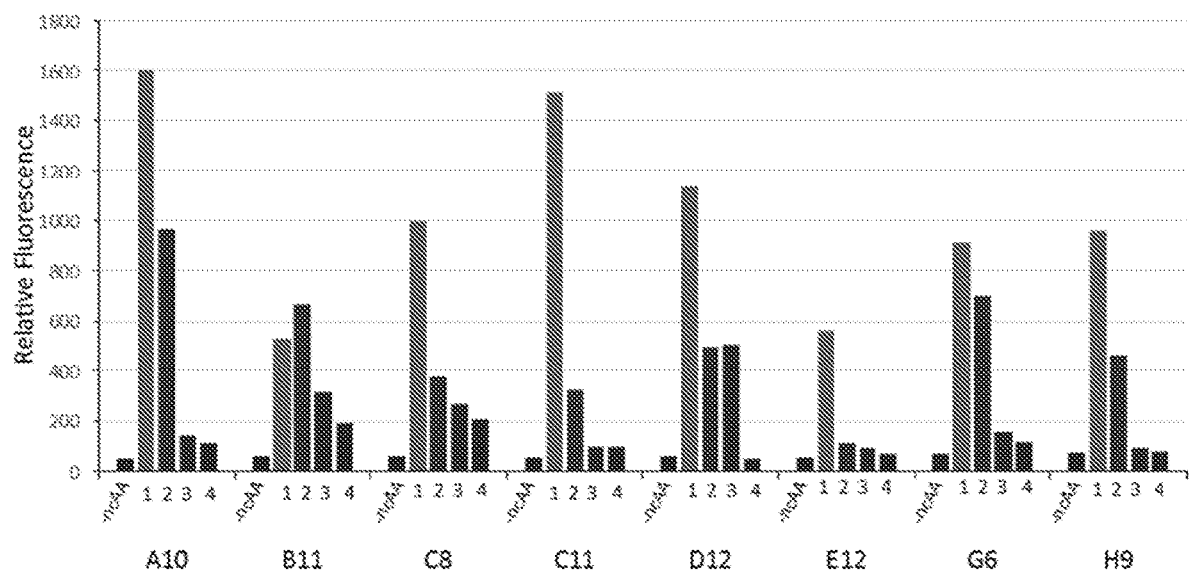
FIG. 12B compares the incorporation efficiency of four representative tetrazine amino acids of the invention (Tet-v2.0-methyl (1), Tet-v2.0-ethyl (2), Tet-v2.0-isopropyl (3), Tet-v2.0-n-butyl) into GFP using selected orthogonal pairs of tRNAs/synthetases (A10, B11, C8, C11, D12, E12, G6, H9). Expression of GFP without non-canonical amino acid (−ncAA) evaluates tRNAs/synthetases fidelity.

To show this method of incorporating tetrazine amino acids using orthogonal (RS)/tRNA$_{CUA}$ pairs can be made general, the following three tetrazine amino acids were incorporated into GFP; 4-(6-ethyl-s-tetrazin-3-yl)phenylalanine (Tet-v2.1), 4-(6-isoproyl-s-tetrazin-3-yl)phenylalanine (Tet-v2.2), 4-(6-butyl-s-tetrazin-3-yl)phenylalanine (Tet-v2.3) FIG. 12B.

The top seven performing clones for Tet-v2.0 were sequenced revealing seven unique clones as summarized in Table 2.

TABLE 2

Sequence of top performing Tet-v2.0-RSs. The D12 synthetase (bold) was moved into the pDule plasmid for protein expression.

| Mj Tyr parent | Tyr32 | Leu65 | Phe108 | Gln109 | Asp158 | Leu162 |
|---|---|---|---|---|---|---|
| A10 | Ala | Ala | Glu | His | Gly | Ser |
| B11 | Ala | Ser | Gln | Glu | Gly | Ala |
| C8 | Ala | Ala | His | Ser | Ser | Gly |
| C11 | Ala | Val | Asp | His | Gly | Ser |
| D12 | Gly | Gln | Ser | Asp | Ser | Asn |
| E12 | Ala | Ala | Leu | Pro | Gly | Gly |
| G6 | Ala | Ser | Ala | Glu | Asn | Ala |
| H9 | Ala | Ser | Gln | Asp | Ser | Ala |

Generation of pDule-Tet2.0

The top performing Tet-RS was moved from the pBK-D12 plasmid to the pDule plasmid (pDule-tet2.0). pDule plasmid was generated by amplifying the MjYRS gene from the pBK plasmid isolated from the library using primers RSmovef (5'-CGCGCGCCATGGACGAATTTGAAATG-3') (SEQ ID NO: 1) and RSmover (5'-GACTCAGTCTAGGTACCCGTTTGAAACTGCAGT-TATA-3') (SEQ ID NO: 2). The amplified DNA fragments were cloned in to the respective sites on the pDule plasmids using the incorporated NcoI and KpnI sites.

Expression and Purification of GFP-Tet2.0

DH10B *E. coli* cells co-transformed with pDule-tet2.0 and pALS GFP-TAG150 vector were used to inoculate 5 mL of non-inducing medium containing 100 μg/mL Amp and 25 μg/mL Tet. The non-inducing medium culture was grown to saturation with shaking at 37° C., and 1 mL was used to inoculate 0.1 L autoinduction medium with 100 μg/mL Amp and 25 μg/mL Tet, and 1 mM Tet2.0 (0.1 L of media grown in 500 mL plastic baffled flasks). After 40 hours of shaking at 37° C., cells were collected by centrifugation. The protein was purified using BD-TALON cobalt ion-exchange chromatography. The cell pellet was resuspended in wash buffer (50 mM sodium phosphate, 300 mM sodium chloride, pH 7) and lysed using a microfluidizer (final volume 35 mL). The lysate was clarified by centrifugation, applied to 0.5 mL bed-volume resin, and bound for 20 min. Bound resin was washed with >50 volumes wash buffer. Protein was eluted from the bound resin with 2.0 mL of elution buffer (50 mM sodium phosphate, 300 mM sodium chloride, 150 mM imidazole pH 7) until the resin turned pink and the color of the eluent the column was no longer green. The elution concentrations were checked with a Bradford protein assay. The protein was desalted into PBS using PD10 columns.

Rapid In Vitro Labeling of Tet-v2.0 Containing Protein with sTCO and dTCO

Pure GFP-Tet-v2.0 at 3 μM in 20 mM ammonium acetate pH 7 was incubated with dioxilane fused trans cyclooctene (dTCO) at a final concentration of 39 M. The reaction was run for 5 min. at room temperature before desalting with PD10 columns into 20 mM ammonium acetate pH 7. These samples were frozen and vacuum dried. GFP and GFP-Tet-v2.0 with no addition of dTCO were run in parallel as controls.

Rapid In Vivo Labeling of Tet2.0 Containing Protein with sTCO

DH10B cells in 50 mL autoinduction media expressing cytosolic GFP-Tet-v2.0 were pelleted at 2000 rcf for 5 min. The cells were washed 3 times with 5 mL PBS. Aliquots of 1 mL cells were centrifuged (2000 rcf, 5 min) and stored at −80° C. Cells were thawed on ice and resuspended in 5 mL PBS. The cells were incubated at 37° C. for 3 hrs with heavy aeration. A stock solution of sTCO was prepared in MeOH with a concentration of 1.0 mM. Cells were diluted in a cuvette (100 μL cells to 2.9 mL PBS). The fluorescence of the reaction was monitored (488 nm excitation, 509 nm emission, 5 mm slit width). Excess addition of sTCO was performed as a positive control (50 μL 1.0 mM). The first three sub-stoichiometric additions (3 μL 1.0 mM) were allowed 3 min to equilibrate before 250 μL of buffer was removed to assess the sTCO concentration. After 5 min the subsequent addition was performed. The fourth addition of sTCO consisted of an excess of sTCO (41 μL 1.0 mM). Control additions of sTCO and subsequent removal were performed for GFP TAG150 cells grown in the absence of Tet-v2.0 and for PBS buffer alone.

In Vitro Incubation of GFP-Tet-v2.0 with sTCO

ESI-MS of proteins; GFP-Tet-v2.0, GFP-Tet-sTCO, and GFP-Tet-dTCO, demonstrates specific and quantitative labeling of GFP-1 and no background labeling of GFP. ESI-MS TOF analysis of WT GFP showed a single major peak at 27826.8 Da±1 Da (expected 27827.3). ESI-MS-TOF analysis of GFP-Tet-v2.0 showed a single major peak at 27953.3 Da±1 Da which is in agreement with the expected mass (27954.5 Da). ESI-MS-TOF analysis of GFP-Tet-v2.0-sTCO showed a single major peak at 28077.1 Da±1 Da (expected 28078.7 Da). This showed the expected molecular weight difference of 124.2 Da from GFP-Tet-v2.0 demonstrating specific and quantitative conversion to GFP-Tet-v2.0-sTCO. ESI-MS-TOF analysis of GFP-Tet-v2.0 incubated with dTCO showed a single major peak at 28181.9 Da±1 Da (expected 28180.7 Da). This shows the expected molecular weight difference of 226.2 Da from GFP-Tet-v2.0 demonstrating specific and quantitative conversion to GFP-Tet-v2.0-dTCO. Each sample did show a small peak at −131±1 Da indicating minor amounts of peptidase-based removal of N-terminal methionines and +22 sodium adducts.

MS Analysis of GFP-Tet-v2.0, GFP-Tet-v2.0-sTCO, GFP-Tet-v2.0-dTCO

Purified GFP and GFP-Tet-v2.0 were diluted to a concentration of 1 mg/mL and reacted with about 5 equivalents of sTCO overnight. Protein was desalted on $C_4$ zip tips and analyzed using an FT LTQ mass spectrometer at the Oregon State University mass spectrometry facility.

Cells that expressed GFP Tet-v2.0 were reacted with about 5 equivalents of sTCO overnight. Protein was purified as described above. Protein in elution buffer was desalted on $C_4$ zip tips and analyzed using an FT LTQ mass spectrometer at the Oregon State University mass spectrometry facility.

In Vivo Kinetic Analysis of GFP-Tet-v2.0 with sTCO

Seven stock solutions of sTCO in methanol were prepared (0.585 mM, 0.293 mM, 0.146 mM, 0.0731 mM, 0.0366 mM, 0.0183 mM, and 0.00914 mM). Solid dTCO was dissolved in methanol to generate seven stock dilutions (1.73 mM, 0.864 mM, 0.432 mM, 0.216 mM, 0.108 mM, 0.054 mM, 0.027 mM). Kinetic trials containing 30 μL of GFP-Tet (1 μM in PBS) in 2.5 mL of 1×PBS buffer at 21° C. were initiated by adding 50 μL of sTCO or dTCO stock solution. Reactions were monitored by observing the fluorescence increase from product formation (excitation 488 nm with a 1.25 nm slit, emission 510 nm with a 4 nm slit). Fluorescence measurements for each trial were run until a constant emission intensity was reached indicating a completed reaction. A unimolecular rate constant was obtained for each concentration and all seven unimolecular rate constants were used to obtain a bimolecular rate constant.

Figure 7A:
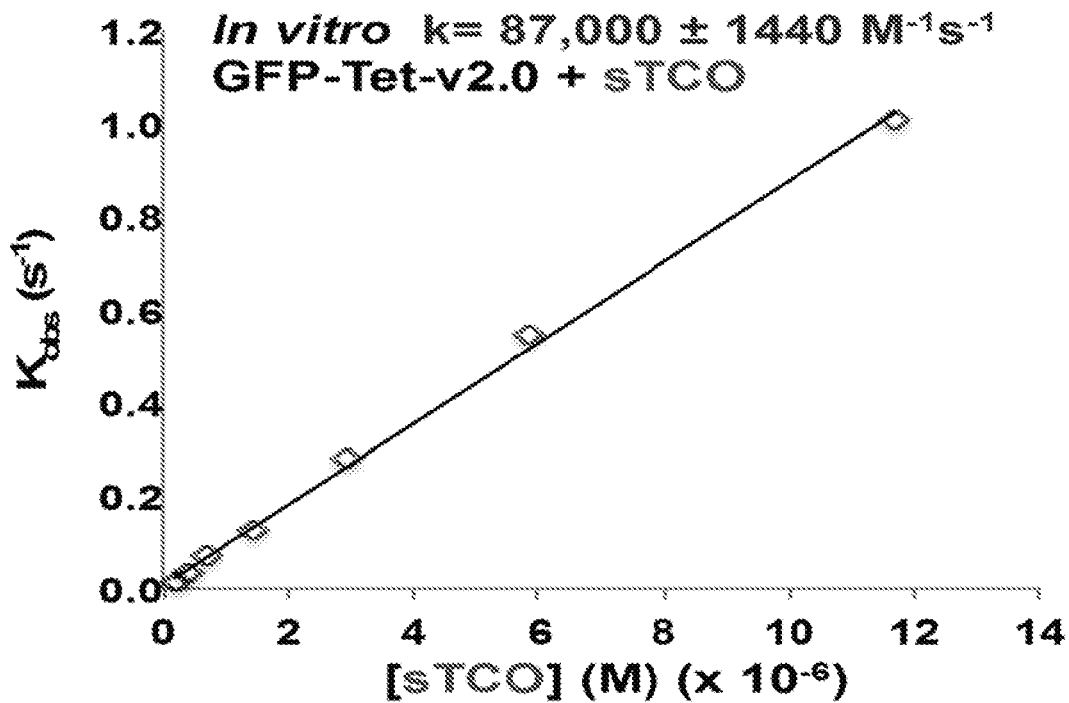
FIGS. 7A and 7B compare in vitro kinetic analysis of GFP-Tet-v2.0 with sTCO and dTCO. Determined first order rate constants were plotted against sTCO or dTCO concentrations. Standard curves were fit to the data and $2^{nd}$ order rate constants were calculated.
Figure 7B:
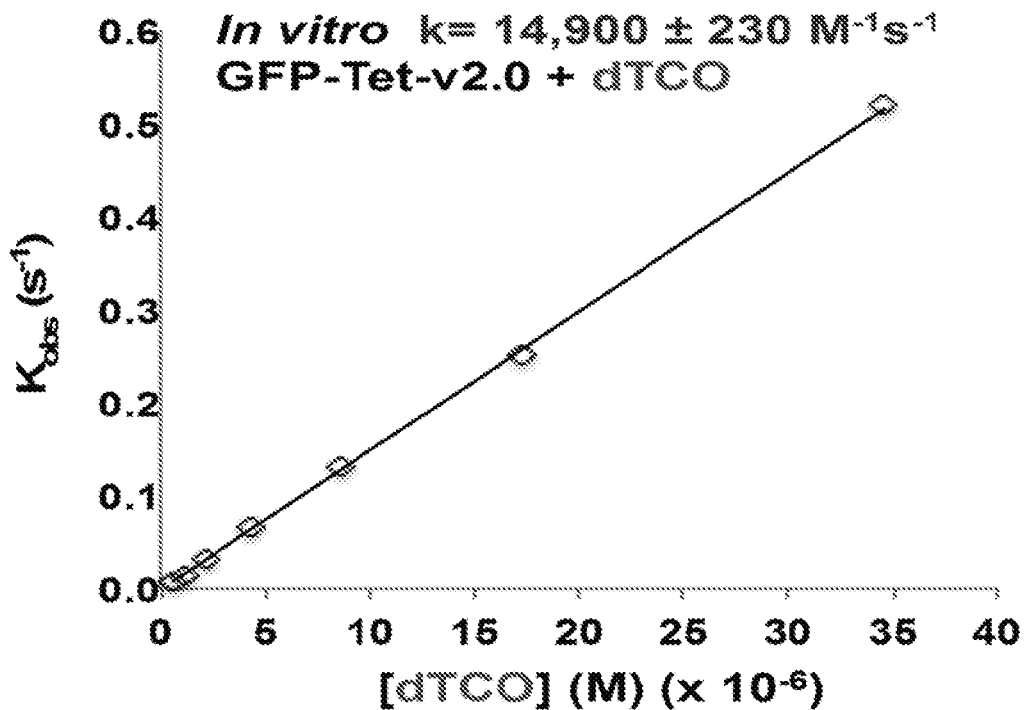

FIGS. 7A and 7B compare in vitro kinetic analysis of GFP-Tet-v2.0 with sTCO (7A) and dTCO (7B). Determined first order rate constants were plotted against sTCO or dTCO concentrations. Standard curves were fit to the data and $2^{nd}$ order rate constants were calculated.

A 50 mL GFP-150-Tet-v2.0 cell pellet was resuspended and washed in 50 mL PBS buffer three times. Six kinetic trials containing 100 µL of the cell solution added to 2.85 mL of 1×PBS buffer were initiated by adding 50 µL of one of six stock solutions of sTCO (613, 306, 153, 76.6, 38.3, 19.1 µM). Kinetics trials were stirred continuously and monitored by observing the fluorescence increase from product formation (excitation 488 nm with 2 nm slit, emission 506 nm with 5 nm slit, 0.1 s integration time, and 2 s increments). Fluorescence measurements for each trial were run until a constant emission intensity indicative of a complete reaction was obtained. A unimolecular rate constant was obtained for each concentration and all six unimolecular rate constants were used to obtain a bimolecular rate constant.

Figure 8:
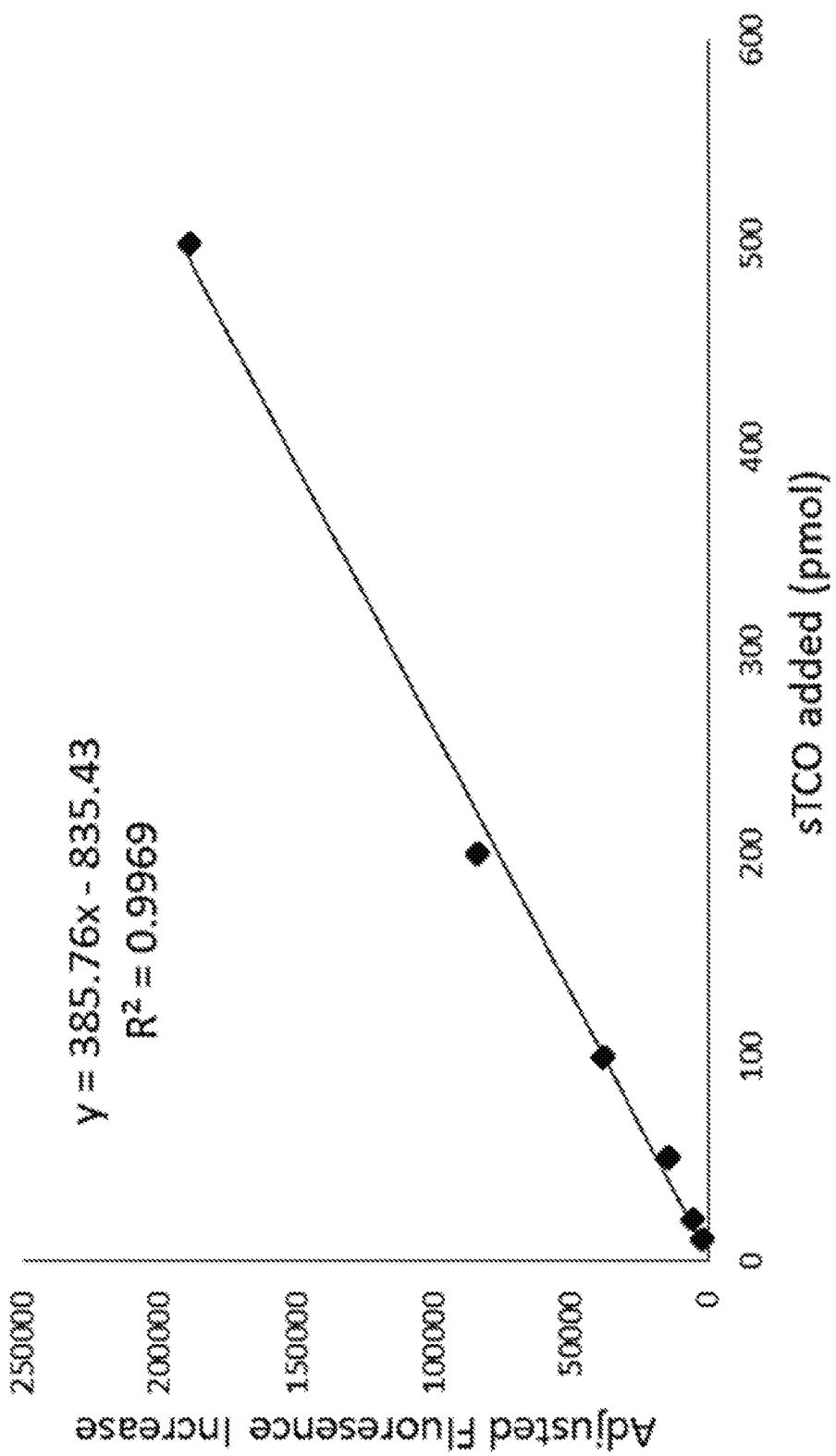
FIG. 8 is the calibration curve for determining sTCO concentration. The adjusted fluorescence increase of additions of sTCO to GFP were plotted against the amount of sTCO. Unknown concentrations of sTCO were then added and the resulting adjusted fluorescence increase was used to determine the concentration of the unknown values.

The calibration curve for determining sTCO concentration is shown in FIG. 8. The adjusted fluorescence increase of additions of sTCO to GFP were plotted against the amount of sTCO. Unknown concentrations of sTCO were then added and the resulting adjusted fluorescence increase was used to determine the concentration of the unknown values.

Assay of sTCO Concentration in Supernatant of Sub-Stoichiometric Additions

The buffer samples from the sub-stoichiometric reactions described above were centrifuged (2000 rcf, 5 min) and 200 µL of supernatant was removed for analysis. To assay the concentration the supernatant was reacted with excess purified GFP-Tet-v2.0 and the fluorescence increase of the GFP-Tet-v2.0 was compared to a standard curve. To generate the standard curve 10 µL GFP-Tet-v2.0 was added to 2990 µL PBS. Known amounts of pure sTCO (10-1000 pmol) were added in volumes of 10-50 µL. The increase in fluorescence of the GFP was measured and the dilution factor was accounted for to result in an adjusted fluorescence increase. The quantity of sTCO was plotted against the adjusted increase and the data were fit with a least squares regression line ($R^2=0.9969$). The adjusted fluorescence increases were measured for 20-50 µL additions of supernant from the PBS, GFP-Tet-v2.0 cells, and the minus amino acid cells. GFP-Tet-v2.0 cells had significant background due to trace amounts of GFP in the supernatant. The background was accounted for by subtracting the adjusted fluorescence increase from addition of the supernatant to 3000 µL PBS buffer alone. The standard curve was used to determine quantities and concentrations of sTCO present in the supernatants and error was determined as the error in the standard curve.

Synthesis of TAMRA Linked sTCO

A dry 25 mL pear shaped flask was charged with (19.7 mg, 31.3 µmol) tetramethylrhodamine 5-(and 6)-carboxamide cadaverine, TFA salt that was partially dissolved in anhydrous dichloromethane (1 mL, 15 mmol). Diisopropylethylamine (20.6 uL, 0.118 mmol) was added and resulted in the complete dissolution of tetramethylrhodamine 5-(and 6)-carboxamide cadaverine. A solution was prepared of (activated sTCO) (18.8 mg, 59.2 µmol) in dichloromethane (1 mL, 15 mmol) and was added to the mixture. The reaction was allowed to proceed at room temperature under argon for 16 hrs. The mixture was dried under reduced pressure and purified using silica gel flash column chromatography (9:1 dichloromethane:methanol) to yield (13.2 mg, 61%) a red solid. $^1$H NMR (400 MHz, $C_2D_6OS$) $^1$H NMR (400 MHz, DMSO $D_6$) δ–8.82 (t, 1H), 8.69 (t, 1H), 8.44 (s, 1H), 8.22 (d, 1H), 8.17 (d, 1H), 8.06 (d, 1H), 7.63 (s, 1H), 7.32 (d, 1H), 7.08 (m, 2H), 5.776 (m, 2H), 5.067 (m, 2H).

Figure 9:
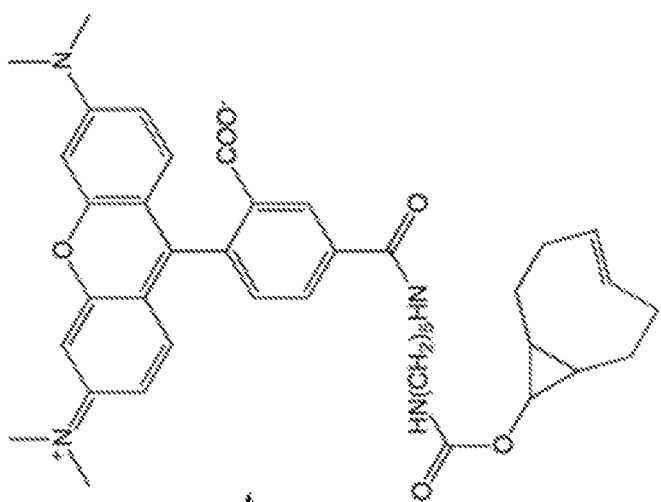
FIG. 9 illustrates the synthesis of TAMRA linked sTCO.
Figure 9:
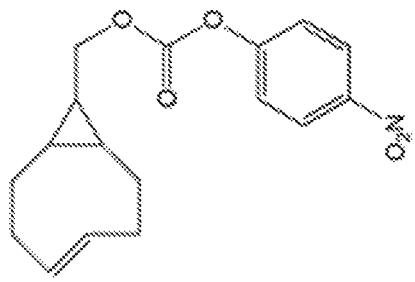
Figure 9:
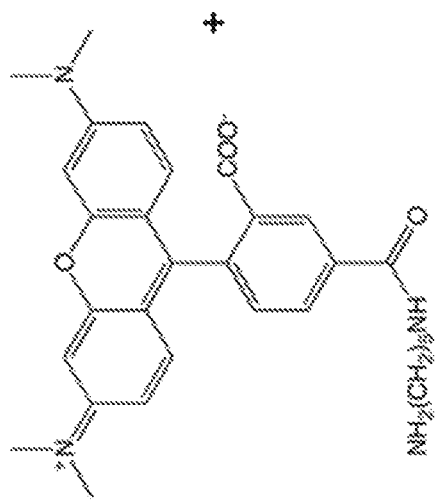

The synthesis of TAMRA linked sTCO is shown in FIG. 9.

SDS-PAGE Analysis of GFP-Tet-v2.0 Incorporation and Reactivity

DH10B cells expressing GFP-Tet-v2.0 from 50 mL auto-inducing media with 1 mM Tet-v2.0 were washed 3 times with 5 mL PBS and finally resuspended in 5 mL PBS. The cells were incubated at 37° C. for 3 hours. Cells were aliquoted in 1 mL and centrifuged (2000 rcf, 5 min) and stored at −80° C. Similarly, WT-GFP expressed cells and cells expressed in absence of Tet2.0 were also aliquoted. TAMRA-sTCO (173 µL, 1 mM) was added to a WT-GFP and GFP-Tet-v2.0 aliquot and allowed to react overnight. Additionally, sTCO was added to an aliquot of GFP-Tet-v2.0 and allowed to react overnight. The aliquots were subsequently lysed and purified using BD-TALON cobalt ion exchange chromatography eluting into 0.5 mL. Equal volumes of purified protein were mixed with 2× Laemmli Buffer and heated at 95° C. for 20 min. Samples were analyzed using SDS-PAGE electrophoresis (7 µL sample, 15% acrylamide gel, 180 V, 70 min). The gel was imaged and fluorescently imaged prior to staining with Coomasie. After staining and destaining the gel was imaged again and the fluorescent image was aligned with the Coomasie-stained image using the ladders visible in the unstained image. Fluorescent signal from the TAMRA label is only present when the dye was reacted with GFP-Tet-v2.0.

TAMRA Labeling of GFP-Tet-v2.0 in Cell Lysate

GFP-Tet-v2.0 expressing *E. coli* cells were resuspended in PBS and lysed. The lysate was clarified via centrifugation (21036 rcf, 45 min) and the supernatant was decanted and stored at 4° C. A mixture of protease inhibitors (400 µL) were added to 20 mL of supernatant. The clarified lysate was divided into 8×1 mL aliquots. TAMRA-sTCO (1 mg/mL in methanol, 0-100 µL) was added to each aliquot. Each sample was allowed to react for 1 hr at room temperature. The samples were mixed with 2× Laemmli Buffer and heated at 95° C. for 20 min. The samples were analyzed via SDS-PAGE electrophoresis (10 µL sample, 15% acrylamide gel, 200V, 50 min). The dye front was not allowed to run off the gel. Samples were fluorescently imaged prior to staining with Coomasie.

Figure 10:
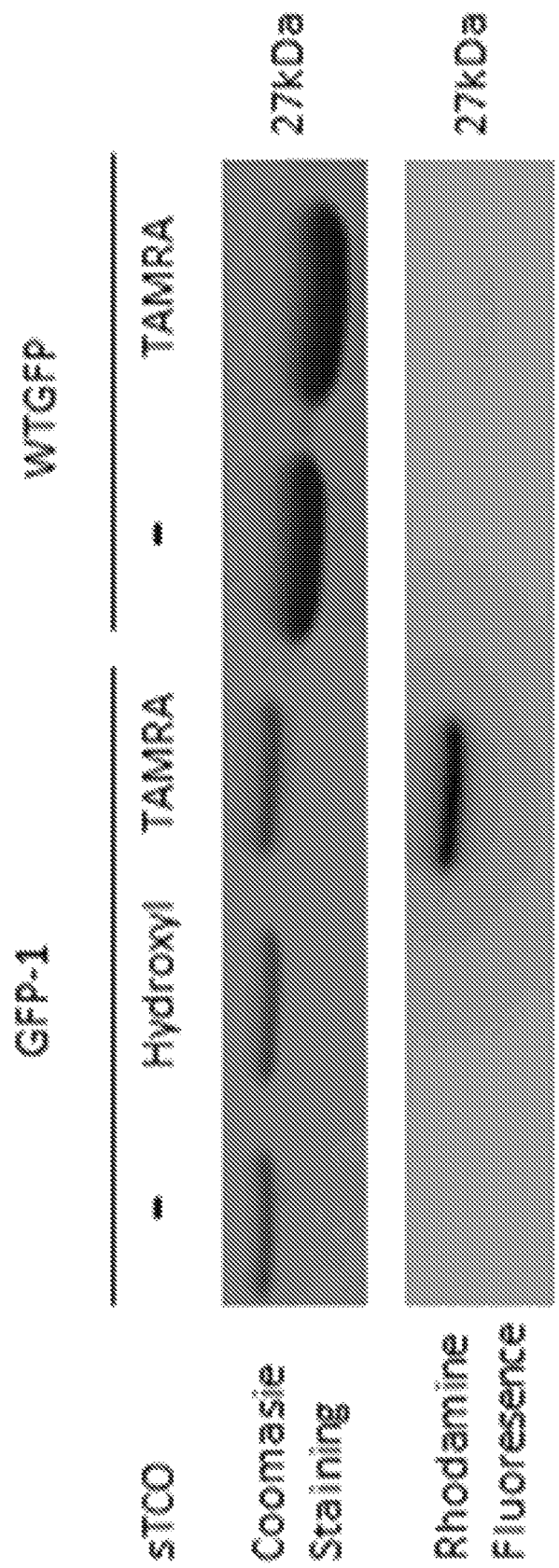
FIG. 10 is the SDS-PAGE analysis of GFP-Tet-v2.0 reactivity. Reaction of TAMRA-sTCO with GFP-Tet-v2.0 resulted in a slight upward gel shift in comparison to the unreacted and sTCO reacted forms. In addition a fluorescent band was visible for the TAMRA-sTCO reacted GFP-Tet-v2.0. No shift was present or fluorescence was observed for WT GFP incubated with TAMRA-sTCO.

FIG. 10 is an image showing the SDS-PAGE analysis of GFP-Tet-v2.0 reactivity. Reaction of TAMRA-sTCO with GFP-Tet-v2.0 resulted in a slight upward gel shift in comparison to the unreacted and sTCO reacted forms. In addition a fluorescent band was visible for the TAMRA-sTCO reacted GFP-Tet-v2.0. No shift was present or fluorescence was observed for WT GFP incubated with TAMRA-sTCO.

Example 4

Selection of *Methanosarcina Barkeri* (Mb) Pyrrolysyl tRNA Synthetase (RS)/tRNA$_{CUA}$ Pair Capable of Incorporating Tet-v3.0 a Representative Tetrazine Amino Acid and Bioorthogonal Labeling: Tet-v3.0-Methyl In this example the selection of aminoacyl-tRNA synthetases specific for a representative tetrazine amino acid, 3-(6-methyl-s-tetrazin-3-yl)phenylalanine (Tet-v3.0-methyl or Tet-3.0-methyl), and bioorthogonal labeling is described.

The library of Mb pyrrolysyl tRNA synthetases was encoded on a kanamycin (Kn) resistant plasmid (pBK) under control of the constitutive *Escherichia coli* GlnRS promoter and terminator. The Mb-aminoacyl synthetase library consists of five sites randomized to all 20 natural amino acids by mutating every codon to NNK where N is A, C, G, or T and K is G or T. The library plasmid, pBK-Mb, was moved between cells containing a positive selection plasmid (pRep pylT) and cells containing a negative selection plasmid (pYOBB2 pylT).

The positive selection plasmid, pRep pylT (10000 bp), encodes a mutant *Methanosarcina Barkeri* (Mb) pyrrolysyl-tRNA$_{CUA}$, an amber codon-disrupted chloramphenicol acetyltransferase, an amber codon-disrupted T7 RNA polymerase, a T7 promoter controlled green fluorescent protein gene, and the tetracycline (Tcn) resistance marker. The negative selection plasmid, pYOBB2 pylT (7000 bp), encodes the mutant pyrrolysyl-tRNA$_{CUA}$, an amber codon-disrupted barnase gene under control of an arabinose promoter and rrnC terminator, and the ampicillin (Amp) resistance marker. pRep pylT electrocompetent cells and pYOBB2 pylT electrocompetent cells were made from DH10B cells carrying the respective plasmids and stored in 100 μL aliquots at −80° C. for future rounds of selection.

pRep pylT/pBK-Mb lib cells were prepared by transforming 960 ng of the pBK Mb lib plasmid into freshly prepared pRep pylT competence cells. The transformation yielded greater than 1000 fold coverage of the pRep pylT library. Transformed cells (5 mL saturated solution) were used to inoculate 300 mL 2×YT containing 50 μg/mL Kn and 25 μg/mL Tcn. The OD of the 2×YT was monitored until it reached 2.8 at which point 250 μL aliquots of media were plated on eleven 15 cm LB-agar plates containing 50 μg/mL Kn, 25 μg/mL Tcn, and 40 μg/mL chloramphenicol (Cm). The positive selection agar medium also contained 1 mM Tet-v3.0. After spreading, the surface of the plates was allowed to dry completely before incubation (37° C., 18 h). To harvest the surviving library members from the plates, 5 mL of 2×YT was added to each plate. Colonies were scraped from the plate using a glass spreader. The resulting solution was incubated with shaking (30 min, 37° C.) to wash cells free of agar. The cells were then pelleted, and plasmid DNA was extracted using a Thermo Scientific miniprep kit. The smaller pBK-Mb plasmid was separated from the larger pRep pylT plasmid by agarose gel electrophoresis and extracted from the gel using a Thermo Scientific gel extraction kit.

The purified pBK-Mb lib plasmid was then transformed into pYOBB2 pylT-containing DH10B cells. A 100 μL sample of pYOBB2 pylT electrocompetent cells was transformed with 59 ng of purified pBK-Mb lib DNA. Cells were rescued in 1 mL of SOC for 1 h (37° C., 250 rpm) and the rescue solution was plated on three 15 cm LB plates containing 100 μg/mL Amp, 25 μg/mL Cm, and 0.2% L-arabinose (250 μL rescue solution per plate). Cells were scraped from plates as described above and pBK-Mb lib DNA was isolated in the same manner as described above for positive selections.

In order to evaluate the success of the positive and negative selection based on variation in synthetase efficacy (as opposed to traditional survival/death results) the synthetases resulting from the selection rounds were tested with the pALS plasmid. This plasmid contains the sfGFP reporter with a TAG codon at residue 150 as well as pyrrolysyl-tRNA$_{CUA}$. When a pBK plasmid with a functional synthetase is transformed with the pALS plasmid and the cells are grown in the presence of the appropriate amino acid on autoinduction agar, sfGFP is expressed and the colonies are visibly green.

The pBK Mb lib plasmid (70 ng) from the negative selection was used to transform 100 μL of pALS-containing DH10B cells. The cells were rescued for 1 hr in 1 mL of SOC (37° C., 250 rpm). A 250 μL and 50 μL of cells from each library were plated on autoinducing agar plates with 25 μg/mL Kn, 50 μg/mL Tcn, with and without 1 mM Tet-3.0. Plates were grown at 37° C. for 24 hours and then grown on the bench top, at room temperature, for an additional 24 hours. Autoinducing agar plates were prepared by combining the reagents in Table 1C with an autoclaved solution of 4.5 g of agar in 400 mL water. Sterile water was added to a final volume of 500 mL.

A total of 48 visually green colonies from the two 1 mM Tet3.0 plates and 48 visually white colonies from the two plates without Tet3.0 were used to inoculate a 96-well plate containing 0.5 mL per well non-inducing minimal media (Table 1B, with sterile water added to a final volume of 500 mL) with 50 μg/mL Kn, 25 μg/mL Tcn. After 24 hours of growth (37° C., 250 rpm), 50 μL of these non-inducing samples were used to inoculate two 96-well plates with 0.5 mL autoinduction media (Table 1C, with sterile water added to a final volume of 500 mL) containing 50 μg/mL Kn, 25 μg/mL Tcn with and without 1 mM Tet-3.0.

Fluorescence measurements of the cultures were collected 24, 48, and 72 hours after inoculation using a BIOTEK® Synergy 2 Microplate Reader. The emission from 528 nm (20 nm bandwidth) was summed with excitation at 485 nm (20 nm bandwidth). Samples were prepared by diluting suspended cells directly from culture 4-fold with sterile water. Seven expressions were selected for their high efficiency with Tet-3.0 and good fidelity without ncAAs present.

Fluorescence Analysis of Highest-Fluorescing Clones

Figure 13:
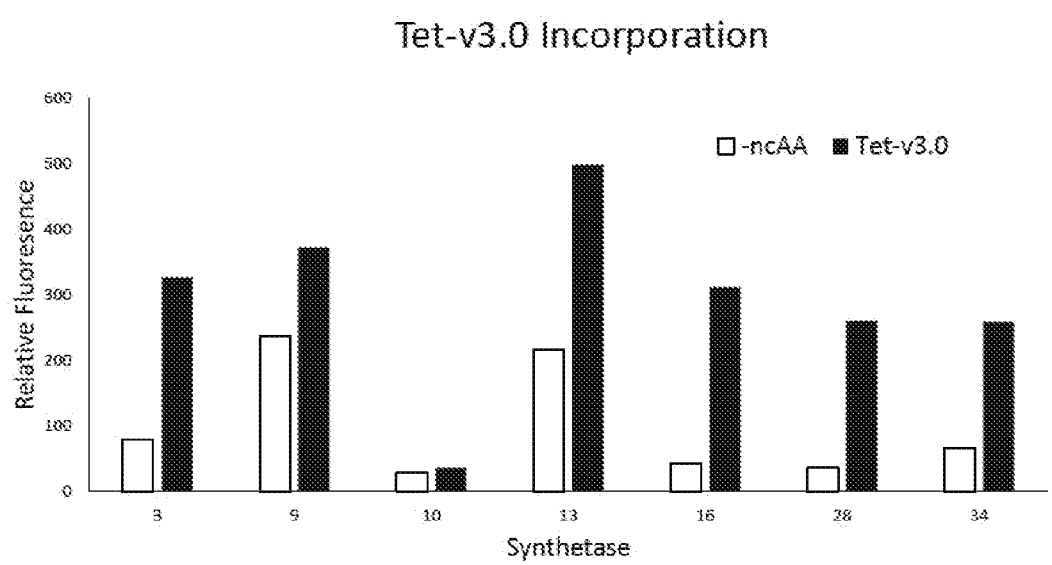
FIG. 13 compares fluorescence measurements of seven synthetases with GFP ncAA-reporter to determine relative efficiency and fidelity of selected synthetases for Tet-v3.0. Non-inducing cultures were grown to saturation from the top seven expressions in the 96 well plate analysis. Autoinduction cultures were inoculated with non-inducing cultures and grown with and without 1 mM Tet-3.0 at 37° C. Black bars represents specific tRNAs/synthetases evaluated in media containing 1 mM Tet-3.0 while white represents colonies induced in the absence of ncAAs.

Non-inducing cultures (5 mL) with 50 μg/mL Kn and 25 μg/mL Tcn were grown to saturation (37° C. with shaking at 250 rpm) from the top seven expressions in the 96 well plate analysis. Autoinduction cultures (5 mL) with 50 μg/mL Kn and 25 μg/mL Tcn were inoculated with 50 μL of non-inducing cultures and grown with and without 1 mM Tet-3.0 at 37° C. with shaking at 250 rpm. Fluorescence was assessed every 12 hours for 24 hours. The results are compared in (see FIG. 13). In FIG. 13, green represents colonies induced in media containing 1 mM Tet-3.0 while red represents colonies induced in the absence of ncAAs. Fluorescence measurements were collected using a Turner Biosystems Picofluor fluorimeter.

The top seven performing clones for Tet-v3.0 were sequenced revealing seven unique clones as summarized in Table 3.

TABLE 3

Sequence of top performing Tet-v3.0-RSs.

| Mb Pyl parent | Asn311 | Cys313 | Val366 | Trp382 | Gly386 |
|---|---|---|---|---|---|
| 3 | Val | Ser | Val | Trp | Gly |
| 9 | Val | Thr | Val | Trp | Gly |
| 10 | Ala | Val | Val | Trp | Gly |
| 13 | Ser | Cys | Val | Trp | Gly |
| 16 | Ala | Thr | Lys | Trp | Gly |
| 28 | Thr | Val | Lys | Trp | Gly |
| 34 | Sequencing | returned | multiple | plasmids | |

Expression and Purification of GFP-Tet3.0

DH10B *E. coli* cells co-transformed with pBK-Mb lib and pALS GFP-TAG150 vector were used to inoculate 5 mL of non-inducing medium containing 50 μg/mL Kn and 25

μg/mL tetracycline. The non-inducing medium culture was grown to saturation with shaking at 37° C., and 0.5 mL was used to inoculate 50 mL autoinduction medium with 50 μg/mL Kn and 25 μg/mL Tcn, and 1 mM Tet-3.0 (0.1 L of media grown in 250 mL plastic baffled flasks). After 40 hours of shaking at 37° C., cells were collected by centrifugation (5000 rcf, 5 min). The protein was purified using BD-TALON cobalt ion-exchange chromatography. The cell pellet was resuspended in wash buffer (50 mM sodium phosphate, 300 mM sodium chloride, pH 7) and lysed using a microfluidizer (final volume 35 mL). The lysate was clarified by centrifugation (21000 rcf, 45 min), applied to 0.5 mL bed-volume resin, and bound for 1 hour. Bound resin was washed with >50 volumes wash buffer. Protein was eluted from the bound resin with 1.0 mL of elution buffer (50 mM sodium phosphate, 300 mM sodium chloride, 150 mM imidazole pH 7) until the resin turned pink and the color of the eluent the column was no longer green. The elution concentrations were checked with a Bradford protein assay. The protein was desalted into 25 mM ammonium acetate buffer.

Purified GFP-Tet-v3.0 were diluted to a concentration of 1 mg/mL and reacted with about 5 equivalents of sTCO overnight. Protein was desalted on $C_4$ zip tips and analyzed using an FT LTQ mass spectrometer at the Oregon State University mass spectrometry facility.

Example 5

Selection of Aminoacyl-tRNA Synthetases Specific for a Representative Tetrazine Amino Acid and Bioorthogonal Labeling: Tet-v3.0-Methyl In this example the selection of aminoacyl-tRNA synthetases specific for a representative tetrazine amino acids (e.g., 3-(6-methyl-s-tetrazin-3-yl)phenylalanine, Tet-v3.0-methyl, and analogs) and bioorthogonal labeling is described.

The D3 library (Leu270, Tyr306, Leu309, Asn346, and Cys348) was chosen for its previously demonstrated ability to incorporate large aromatic amino acids into proteins. The D3 library was encoded on a kanamycin (kn) resistant plasmid (pBK, 3000 bp) under control of the constitutive *Escherichia coli* GlnRS promoter and terminator. The aminoacyl synthetase library consists of the codons at the aforementioned sites mutated to NNK codons corresponding to all 20 natural amino acids where N is A, C, G, or T and K is G or T. The library plasmid, pBK D3 lib, was moved between cells containing a positive selection plasmid (pRep pylT).

The positive selection plasmid, pRep pylT (10000 bp), encodes a mutant *Methanosarcina Barkeri* (Mb) pyrrolysyl-tRNA$_{CUA}$, an amber codon-disrupted chloramphenicol acetyltransferase, an amber codon-disrupted T7 RNA polymerase, a T7 promoter controlled GFP gene, and the tetracycline (Tcn) resistance marker. The negative selection plasmid, pYOBB2 pylT (7000 bp), encodes the mutant pyrrolysyl-tRNA$_{CUA}$, an amber codon-disrupted barnase gene under control of an arabinose promoter and rrnC terminator, and the ampicillin (Amp) resistance marker. pRep pylT electrocompetent cells and pYOBB2 pylT electrocompetent cells were made from DH10B cells carrying the respective plasmids and stored in 100 μL aliquots at −80° C. for future rounds of selection.

pRep pylT/pBK D3 lib cells were prepared by transforming 1.6 μg of the pBK D3 lib plasmid into freshly prepared pRep pylT competence cells. The transformation yielded greater than 1000 fold coverage of the pRep pylT library. Transformed cells (10 mL saturated solution) were used to inoculate 300 mL 2×YT containing 50 μg/mL Kn and 25 μg/mL Tcn. The OD of the 2×YT was monitored until it reached 2.8 at which point 250 μL aliquots of media were plated on eleven 15 cm LB-agar plates containing 50 μg/mL Kn, 25 μg/mL Tcn, and 40 μg/mL chloramphenicol (Cm). The positive selection agar medium also contained 1 mM Tet-v3.0. After spreading, the surface of the plates was allowed to dry completely before incubation (37° C., 18 h). To harvest the surviving library members from the plates, 5 mL of 2×YT was added to each plate. Colonies were scraped from the plate using a glass spreader. The resulting solution was incubated with shaking (30 min, 37° C.) to wash cells free of agar. The cells were then pelleted, and plasmid DNA was extracted using a Thermo Scientific miniprep kit. The smaller pBK D3 lib plasmid was separated from the larger pRep pylT plasmid by agarose gel electrophoresis and extracted from the gel using a Thermo Scientific gel extraction kit.

The purified pBK Susan2 lib plasmid was then transformed into pYOBB2 pylT-containing DH10B cells. A 100 μL sample of pYOBB2 pylT electrocompetent cells was transformed with 5.0 ng of purified pBK D3 lib DNA. Cells were rescued in 1 mL of SOC for 1 h (37° C., 250 rpm) and the rescue solution was plated on three 15 cm LB plates containing 100 μg/mL Amp, 25 μg/mL Cm, and 0.2% L-arabinose (250 μL rescue solution per plate). Cells were scraped from plates as described above and pBK D3 lib DNA was isolated in the same manner as described above for positive selections. At this point some of the library was retransformed into pREP pylT containing cells for a second round of positive and negative selections. After the second round of selections, DNA from both the end of the first and the end of the second negative rounds was further evaluated.

In order to evaluate the success of the positive and negative selections based on variation in synthetase efficiency (as opposed to traditional survival/death results) the synthetases resulting from the selection rounds were tested with the pALS plasmid. This plasmid contains the sfGFP reporter with a TAG codon at residue 150 as well as pyrrolysyl-tRNA$_{CUA}$. When a pBK plasmid with a functional synthetase is transformed with the pALS plasmid and the cells are grown in the presence of the appropriate amino acid on autoinduction agar, sfGFP is expressed and the colonies are visibly green.

The pBK D3 lib plasmid (70 ng) from the negative selection was used to transform 100 μL of pALS-containing DH10B cells. The cells were rescued for 1 hr in 1 mL of SOC (37° C., 250 rpm). Both 250 μL and 50 μL aliquots of cells from each library were plated on autoinducing agar plates with 25 μg/mL Kn, 50 μg/mL Tcn, with and without 1 mM Tet-v3.0. Plates were grown at 37° C. for 24 hours and then grown on the bench top, at room temperature, for an additional 24 hours. Autoinducing agar plates were prepared by combining the reagents in Table 2C with an autoclaved solution of 4.5 g of agar in 400 mL water. Sterile water was added to a final volume of 500 mL.

A total of 72 visually green colonies from the two 1 mM Tet-v3.0 plates and 24 visually white colonies from the two plates without Tet-v3.0 were used to inoculate a 96-well plate containing 0.5 mL per well non-inducing minimal media (Table 2, with sterile water added to a final volume of 500 mL) with 50 μg/mL Kn, 25 μg/mL Tcn. After 24 hours of growth (37° C., 250 rpm), 50 μL of these non-inducing samples were used to inoculate two 96-well plates with 0.5 mL autoinduction media (see Table 1, with sterile water added to a final volume of 500 mL) containing 50 µg/mL Kn, 25 µg/mL Tcn with and without 1 mM Tet-v3.0.

Fluorescence measurements of the cultures were collected 24, 48, and 72 hours after inoculation using a BIOTEK® Synergy 2 Microplate Reader. The emission from 528 nm (20 nm bandwidth) was summed with excitation at 485 nm (20 nm bandwidth). Samples were prepared by diluting suspended cells directly from culture 4-fold with sterile water. Fifteen colonies were selected for their high fluorescence with Tet-v3.0 present and low fluorescence in the absence of ncAAs. Selected hits were stored as cell stocks at –80° C. in 20% glycerol.

Selections were also performed using the Susan2 library: Asn311, Cys313, Val366, Trp382, and Gly 386. However, hits from the Susan2 library demonstrated poorer fidelity and were not characterized further.

Components for autoinducing and non-inducing mediums, for final volume of 500 mL, are summarized in Table 1 above.

Characterization of Efficiency and Fidelity.

After the completion of the selections, efficiency and fidelity were measured in larger, more aerated cultures. Cell stocks were used to inoculate 5 mL of noninduction media containing Kn (50 µg/mL) and Tcn (25 µg/mL) and allowed to grow overnight (37° C., 18 hrs). Saturated noninduction media (50 µL) was then used to inoculate autoinduction media containing Kn (50 µg/mL), Tcn (25 µg/mL), and Tet-v3.0 (1 mM). Fluorescence was measured every 12 hrs for 48 hrs. The results are compared in FIG. 15. Fluorescence measurements were collected using a Turner Biosystems Picofluor fluorimeter.

Figure 15:
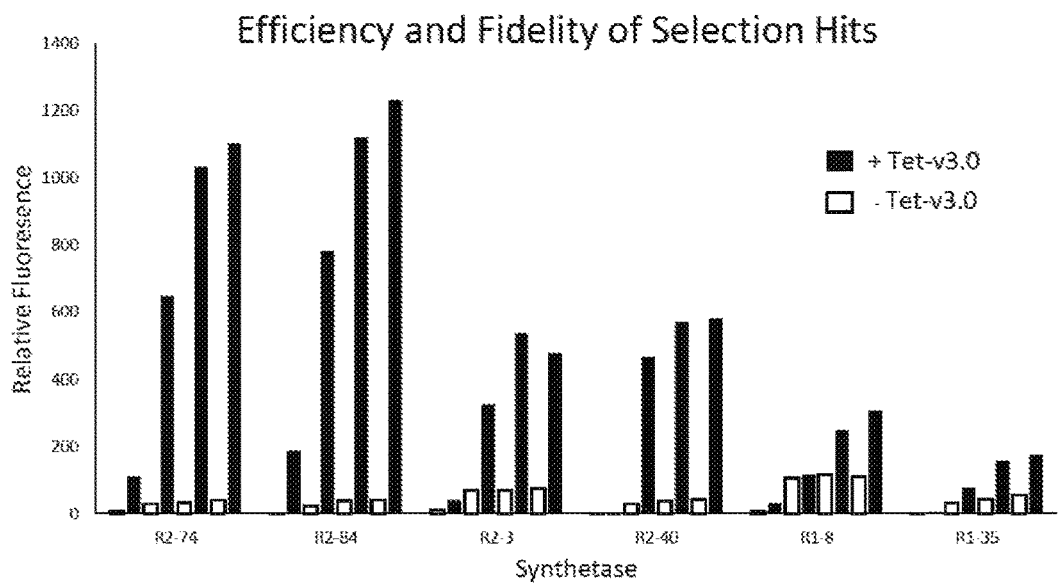
FIG. 15 compares efficiency and fidelity of selection hits for synthetases R2-74, R2-84, R2-3, R2-40, R1-8, and R1-35. Assessed hits demonstrated good efficiency (high fluorescence when grown in the presence of Tet-v3.0-methyl) and good fidelity (low fluorescence in the absence of Tet-3.0-methyl). Measurements were taken after 12, 24, 36, and 48 hrs.

FIG. 15 compares efficiency and fidelity of selection hits for synthetases R2-74, R2-84, R2-3, R2-40, R1-8, and R1-35. Assessed hits demonstrated good efficiency (high fluorescence when grown in the presence of Tet-v3.0-methyl) and good fidelity (low fluorescence in the absence of Tet-v3.0-methyl). Measurements were taken after 12, 24, 36, and 48 hrs.

Sequencing of Tet-v3.0-Methyl Hits.

The cell stocks were sequenced using the PylRS reverse primer (Table 4). Of the fifteen colonies sequenced, six unique sequences were identified and the sequences can be found in Table 4. It is of note that the hits termed R2-3 and R2-84 differ only by the mutation Arg263Cys which is not predicted to directly contact the amino acid or play an essential role in catalysis.

TABLE 4

Sequences of Tet-v3.0 synthetase hits.

| Mutation | R1-8 | R1-35 | R2-3 | R2-40 | R2-74 | R2-84 |
|---|---|---|---|---|---|---|
| L270 | — | — | G | — | G | G |
| Y271 | — | — | — | — | — | — |
| L274 | — | — | — | — | — | — |
| N311 | A | A | G | G | G | G |
| C313 | S | V | A | A | S | A |
| Other | — | — | — | K296R | — | R263C |

Sequences are compared to the WT *M. barkeri* PylRS. Dashes indicate no mutation. Off-library mutations are indicated as other. Note R2-3 and R2-84 differ by only the off-library R263C mutation.

Selection of Tet-v3.0-Methyl at Multiple Concentrations.

In addition to selections at concentrations of 1 mM Tet-v3.0-methyl, selections were performed at positive selection and colony assessment amino acid concentrations of 0.1 mM Tet-v3.0-methyl and 0.05 mM Tet-v3.0-methyl as well. After each round of selection, 48 visually green colonies were selected for further assessment in 96-well plates. Fifteen hits from concurrent 1 mM and 0.05 mM selections were sequenced. The 1 mM selection had greater diversity of hits in comparison to the 0.05 mM selection. When the efficiency and fidelity of these hits were measured at concentrations ranging from 0.1 mM Tet-v3.0-methyl to 1 mM Tet-v3.0-methyl in 5 mL culture it was found that the hits selected for at 0.05 mM had greater efficiency at lower concentrations than those selected for at 1 mM ncAA.

$UP_{50}$ Characterization of Select Synthetases.

The $UP_{50}$ value is a measure of amino acid concentration at which cells containing a given synthetase produces half of the maximum amount of unnatural protein containing the amino acid of interest. In this way the $UP_{50}$ is dependent both on the synthetase and amino acid of interest. This value is obtained by measuring the fluorescence of produced GFP at various concentrations of amino acids and fitting measured values to the curve:

$$UP = \frac{UPmax \times [AA]}{UP_{50} + [AA]}$$

UP is the measured fluorescence, [AA] is the amino acid concentration, and $UP_{max}$ is the maximum protein produced. The methodology for obtaining $UP_{50}$ and $UP_{max}$ values is described below.

Non-inducing media starter cultures containing Tcn (25 µg/mL) and Kn (50 µg/mL) were grown overnight (37° C., 18 hrs). Starter cultures consisted of *E. coli* DH10B transformed with a pBK plasmid containing the synthetases of interest (R2-40, R2-74, and R2-84) and tRNA, as well as a pALS plasmid containing an amber codon interrupted GFP gene under control of an araBAD promoter. Starters were used to inoculate (30 µL) autoinducing media (3 mL) containing Tcn (25 µg/mL), Kn (50 µg/mL), and Tet-v3.0 at various concentrations. Tet-v3.0 concentrations were varied from 0.005 mM to 1 mM with duplicates for each concentration. As a control, media was inoculated in duplicate containing no amino acid. To aid in dissolution, 30 µL of N,N-dimethyl formamide (DMF) was added to the Tet-v3.0 prior to addition to media. This resulted in the media consisting of 1% DMF in addition to the components listed in Table 5.

TABLE 5

$UP_{50}$ and $UP_{max}$ values for select synthetases.

| Synthetase | R2-40 | R2-74 | R2-84 |
|---|---|---|---|
| $UP_{50}$ (µM) | 0.038 | 0.13 | 0.017 |
| $UP_{max}$ | 540 | 400 | 517 |

Figure 16:
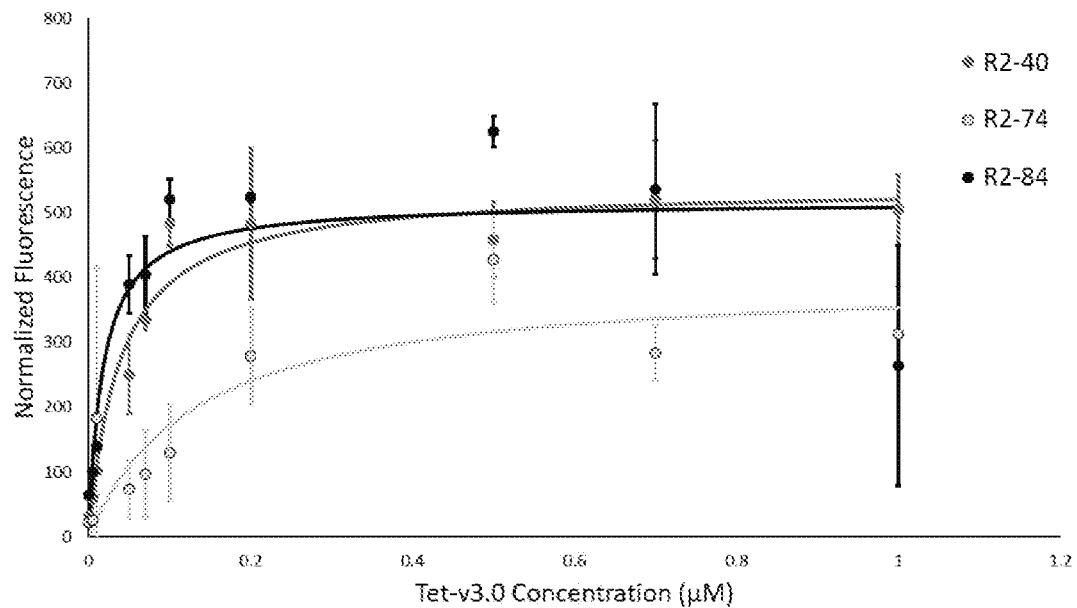
FIG. 16 compares $UP_{50}$ titration curves for three Tet-v3.0-methyl incorporating synthetases: R2-40, R2-74, and R2-84. $UP_{50}$ and $UP_{max}$ values are obtained from the fit of the curves. The R2-74 synthetase was moved into eukaryotic plasmids for protein expression.

The fluorescence and optical density of the media was measured after 24, 36, and 48 hrs. The fluorescence normalized to the optical density was plotted across Tet-v3.0 concentrations and used to calculate the $UP_{50}$ and $UP_{max}$ for individual synthetases (see FIG. 16. FIG. 16 compares $UP_{50}$ titration curves for three Tet-v3.0-methyl incorporating synthetases: R2-40, R2-74, and R2-84. $UP_{50}$ and $UP_{max}$ values are obtained from the fit of the curves. The R2-74 synthetase was moved into eukaryotic plasmids for protein expression.

Protein Production Using Tet-v3.0.

Noninducing media starter cultures containing Tcn (25 µg/mL) and Kn (50 µg/mL) were grown overnight (37° C., 18 hrs). Starter cultures consisted of E. coli DH10B transformed with a pBK plasmid containing the synthetases of interest (R2-40, R2-74, and R2-84) and tRNA, as well as a pALS plasmid containing an amber codon interrupted GFP gene under control of an araBAD promoter. Starters were used to inoculate (500 µL) autoinducing media (50 mL) containing Tcn (25 µg/mL), Kn (50 µg/mL), and Tet-v3.0 (1 mM). Cultures were grown for 39-48 hrs before centrifugation (10 min, 5525 rcf). Supernatant was discarded and pellets were stored a −80° C. prior to purification. For purification, cells were resuspended in wash buffer (50 mM $Na_2HPO_4$, 300 mM NaCl, pH 7.0) and lysed using a Microfluidics M-110P shear fluid processor. Lysate was clarified (21036 rcf, 1 hr) and incubated with TALON Metal Affinity Resin (10 µL resin per 1 mL culture, 4° C., 1 hr). The resin was added to a column and washed with wash buffer (3×10 mL) prior to elution (4×0.25 mL) with elution buffer (50 mM $Na_2PO_4$, 300 mM NaCl, 50 mM imidazole). Purified protein concentration was measured using a Bradford assay.

Gel Characterization of GFP-Tet-v3.0 Production and Activity.

Figure 17:
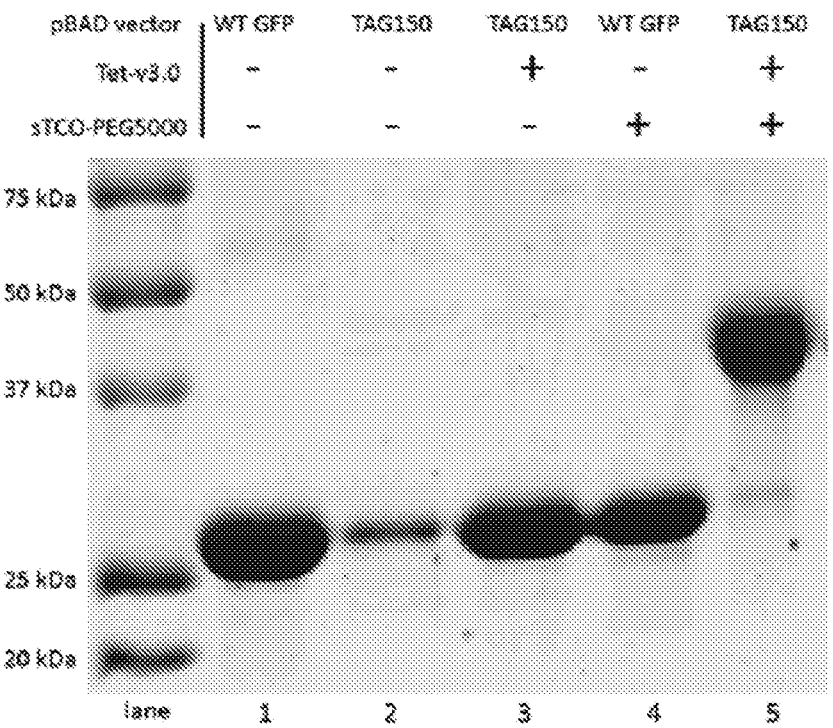
FIG. 17 is an image of an SDS-PAGE gel of Tet-v3.0-methyl containing GFP: Lane 1 shows background production of WT-GFP; Lanes 2 and 3 show production levels of GFP-TAG150 in the presence and absence of Tet-v3.0-methyl; and Lanes 4 and 5 show the Tet-v3.0-methyl dependent shift in mass upon addition of sTCO-PEG-5000.

GFP-Tet-v3.0 was expressed as described above both in the presence and absence of Tet-v3.0. Both expressions were purified as described above. The protein was analyzed in equal volume amounts using SDS-PAGE (FIG. 17). Additionally, samples of GFP-Tet-v3.0 and WT GFP were incubated with excess sTCO-PEG5000 for 30 min prior to SDS-PAGE analysis. This results in a complete gel shift towards a higher molecular weight for GFP-Tet-v3.0 and no gel shift for WT GFP incubated this way. This demonstrates that purified GFP-Tet-v3.0 is reactive with sTCO. The lack of unreacted GFP-Tet-v3.0 indicates that all GFP-Tet-v3.0 contains active Tet-v3.0.

FIG. 17 is an image of an SDS-PAGE gel of Tet-v3.0-methyl containing GFP: Lane 1 shows background production of WT-GFP; Lanes 2 and 3 show production levels of GFP-TAG150 in the presence and absence of Tet-v3.0; and Lanes 4 and 5 show the Tet-v3.0 dependent shift in mass upon addition of sTCO-PEG-5000.

Mass Spectrometry of GFP-Tet-v3.0.

Figure 18A:
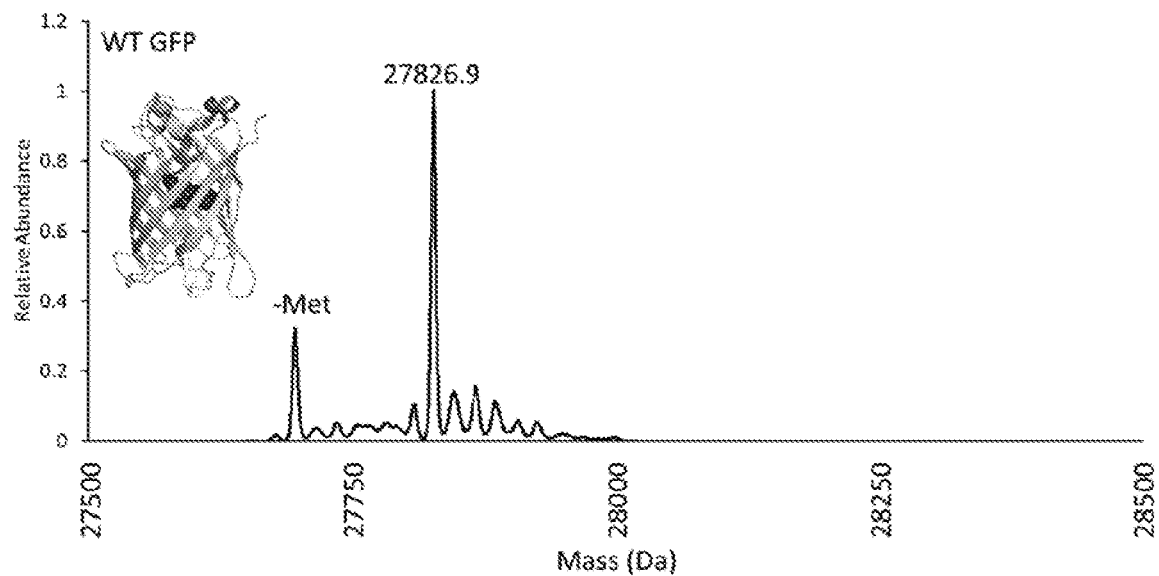
FIGS. 18A-18D compare mass spectra of WT GFP and GFP-Tet-v3.0-methyl reacted with sTCO and TCO. Expected masses are as follows: WT GFP: 27827.3 Da (FIG. 18A). GFP-TAG150 Tet-v3.0-methyl: 27954.5 Da (FIG. 18B). GFP-TAG150-Tet-v3.0-methyl-sTCO: 28078.7 Da (FIG. 18C). GFP-TAG150-Tet-v3.0-methyl-TCO: 28135.8 Da (FIG. 18D).
Figure 18B:
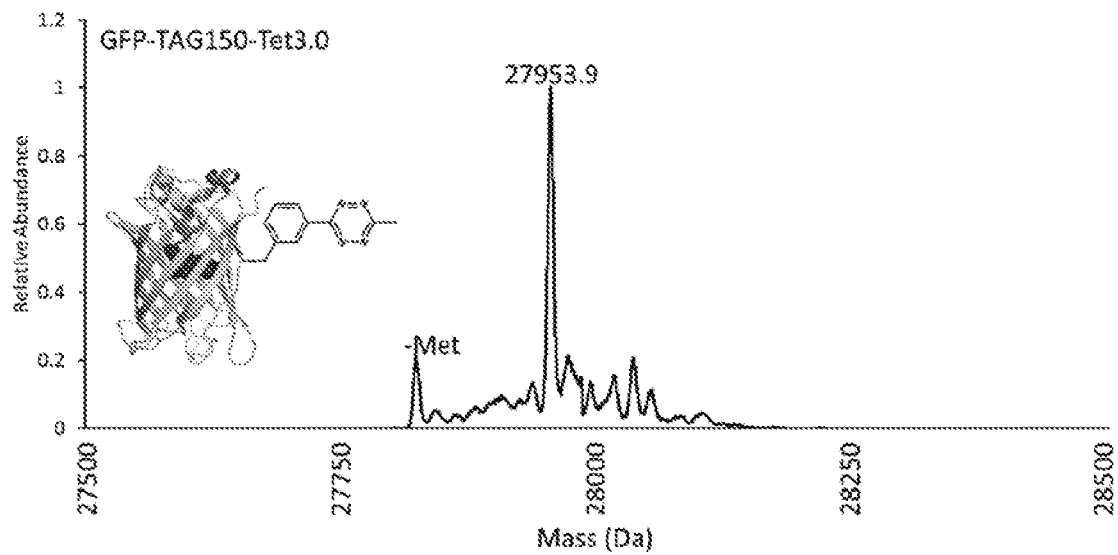
Figure 18C:
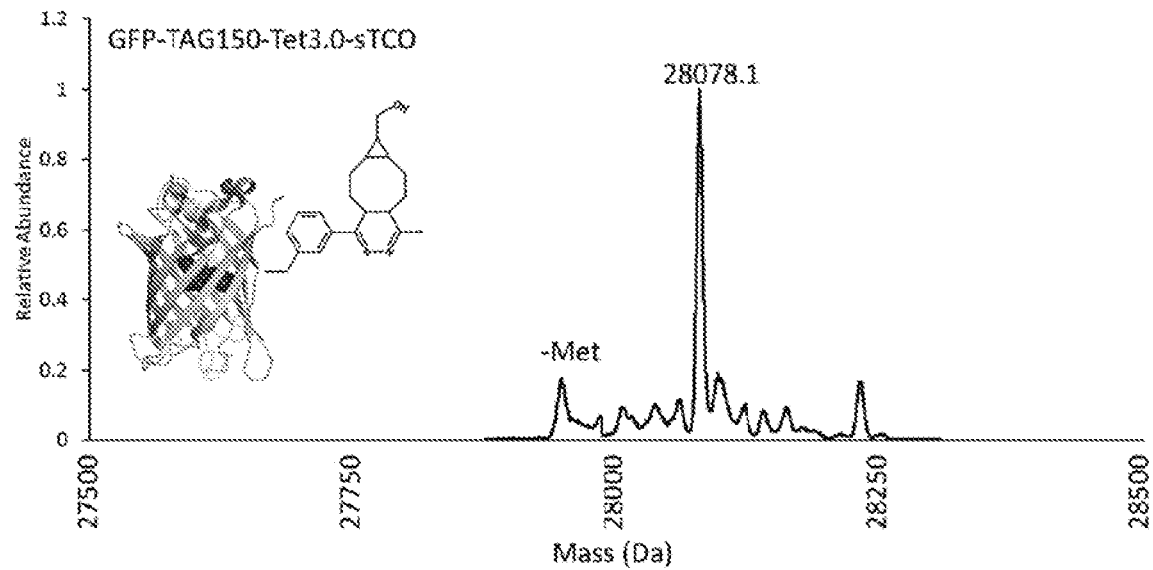
Figure 18D:
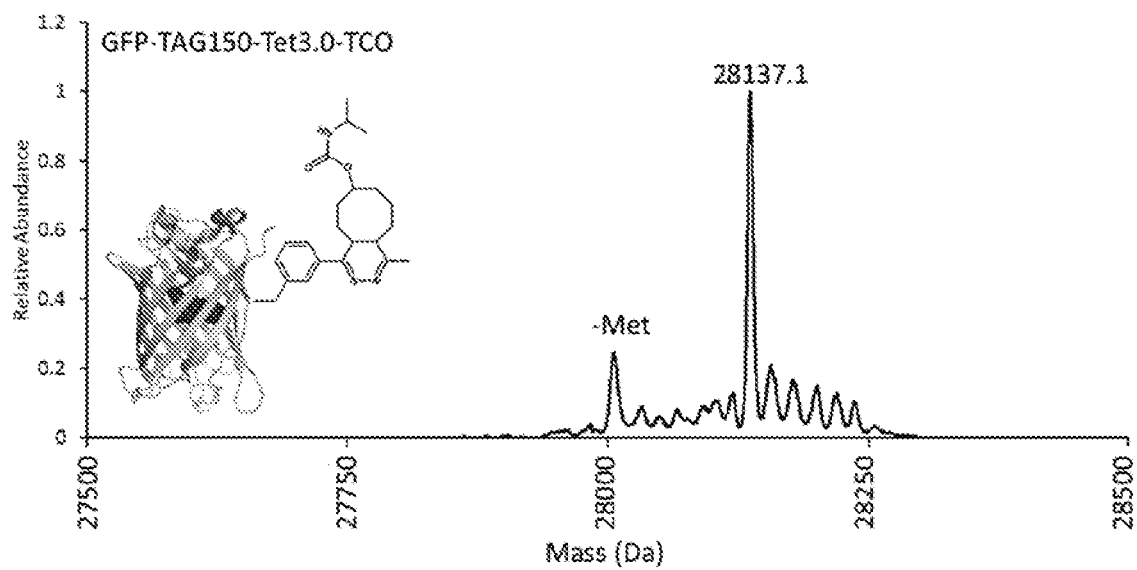

Purified GFP-Tet-v3.0 was diluted to a concentration of 10 µM and reacted with sTCO and TCO in excess overnight. Samples were desalted on $C_4$ zip tips and analyzed using an FT LTQ mass spectrometer at the Oregon State University Mass Spectrometry Facility. Samples include reacted and unreacted GFP-Tet-v3.0 as well as WT GFP (see FIGS. 18A-18D). FIGS. 18A-18D compare mass spectra of WT GFP and GFP-Tet-v3.0-methyl reacted with sTCO and TCO. Expected masses are as follows: WT GFP: 27827.3 Da (FIG. 18A). GFP-TAG150 Tet-v3.0-methyl: 27954.5 Da (FIG. 18B). GFP-TAG150-Tet-v3.0-methyl-sTCO: 28078.7 Da (FIG. 18C). GFP-TAG150-Tet-v3.0-methyl-TCO: 28135.8 Da (FIG. 18D).

Rate Constant Characterization of Tet-v3.0 and Derivatives.

Purified GFP-Tet-v3.0 and derivatives were used to monitor the reaction rate between Tet-v3.0 and sTCO. Fluorescence of the reactions between GFP-Tet-v3.0 and sTCO was monitored to determine reaction progress. GFP (10 µL) of unknown concentration was reacted in 3 mL PBS (pH 7.4) at 21° C. with sTCO (10 µL) at concentrations ranging from 50 µM to 10 mM for a final concentration range of 167 nM to 33.3 µM. The increase in fluorescence upon reaction was measured and fit to an exponential curve using IGOR Pro.

Figure 19A:
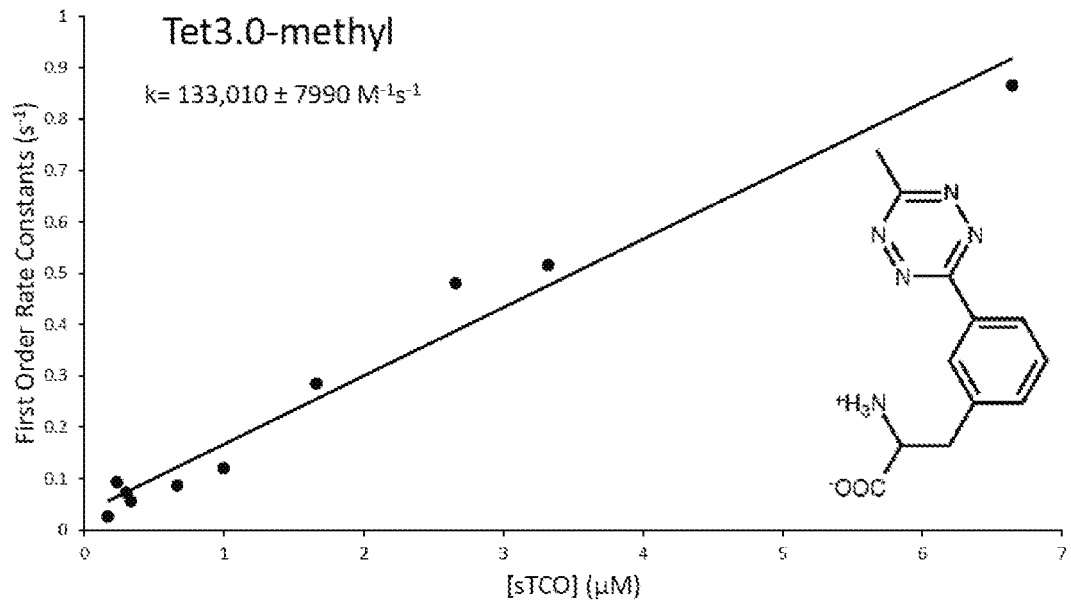
FIGS. 19A-19C compare rate constant characterization of Tet-v3.0-methyl (FIG. 19A), Tet-v3.0-butyl (FIG. 19B), and Tet-v3.0-isopropyl (FIG. 19C). First order kinetic constants were plotted against the sTCO concentration used to obtain them and fit to a linear curve. The second order constant is stated and found by the slope of the curve.
Figure 19B:
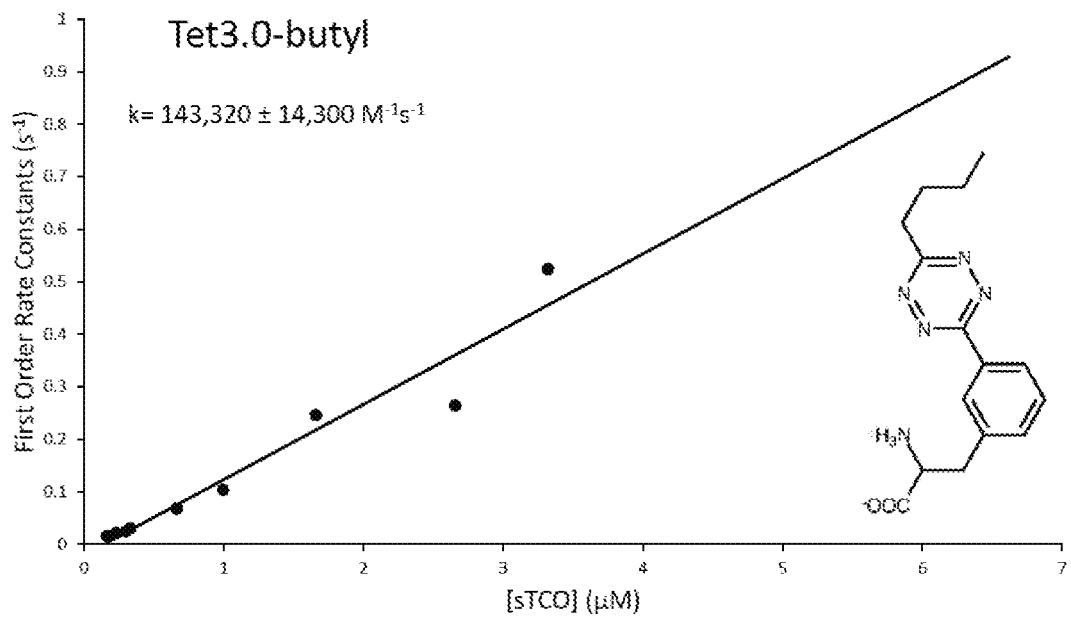
Figure 19C:
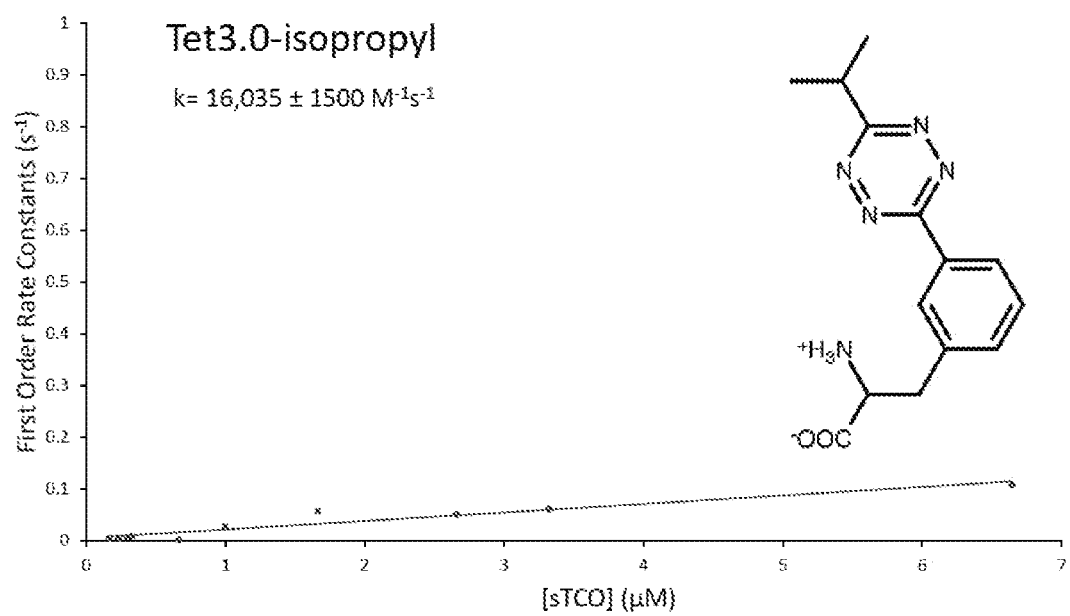

First order rate constants were obtained for each concentration of sTCO. Obtained first order rate constants were plotted against the sTCO concentration and fit to a linear curve. The resulting slope was determined and is equivalent to the second order rate constant. At higher concentrations observed first order rate constants did not fit a linear curve due to slow mixing and values were omitted in the calculation of the second order rate constant. Values were obtained for the reactions between Tet-v3.0, Tet-v3.0-isopropyl, and Tet-v3.0-butyl and are summarized in FIGS. 19A-19C. FIGS. 19A-19C compare rate constant characterization of Tet-v3.0-methyl (FIG. 19A), Tet-v3.0-butyl (FIG. 19B), and Tet-v3.0-isopropyl (FIG. 19C). First order kinetic constants were plotted against the sTCO concentration used to obtain them and fit to a linear curve. The second order constant is stated and found by the slope of the curve.

Cloning of Tet-v3.0 Synthetases into Eukaryotic Vectors.

The R2-74 synthetase was chosen for expression in HEK293T cells. In order to express the R2-74 synthetase it was cloned into a pAcBac plasmid. A G-block gene fragment was obtained encoding the mutations of interest in the PylRS gene. The G-block was amplified using the G-block forward and reverse primer (Table 6). The backbone of a pUC19 vector containing a mammalian optimized PylRS gene was amplified using the using the pUC19 forward and reverse primer (Table 6). The two amplifications were ligated using isothermal assembly to form a pUC19 plasmid containing the R2-74 PylRS gene. The gene was digested from the pUC19 plasmid using an Nhe1/EcoR1 double digest. The pAcBac plasmid was also double digested with Nhe1/EcoR1. The fragments were purified using gel electrophoresis and ligated using a $T_4$ ligase. The resulting pAcBac R2-74 plasmid was amplified and purified for transfection into HEK293T cells.

TABLE 6

Primers used for Tet3.0-RS molecular biology.

| | | |
|---|---|---|
| G-block Amplification | Forward | 5'-CTTCCTGGAAATCAAGAGCCCCATC-3' SEQ ID NO: 3 |
| | Reverse | 5'-GTTCCAGGTCGCCGTGCATG-3' SEQ ID NO: 4 |
| pUC19 Amplification | Forward | 5'-TGCACGGCGACCTGGAAC-3' SEQ ID NO: 5 |
| | Reverse | 5'-GGGGCTCTTGATTTCCAGGAAG-3' SEQ ID NO: 6 |
| PylRS Sequencing | Reverse | 5'-CATGTAGGCCTGATAAGCGTAG-3' SEQ ID NO: 7 |

Cell Culture and Transfection.

HEK293 and HEK293T cells were cultured in DMEM (Mediatech, Manassas, VA) supplemented with 10% fetal bovine serum (Tissue Culture Biologicals, Tulare, CA) and penicillin streptomycin (Mediatech). HEK293 cells were transfected using jetPRIME transfection reagent (Polyplus, New York, NY) according to the manufacturer's protocol. Briefly, HEK293 cells were plated in a 6-well plate (Greiner Bio-One, Monroe, NC) for 70%–80% of confluency at the time of transfection. A mixture of 2 µg DNA and 4 µl of jetPRIME reagent diluted in 200 µl of jetPRIME buffer was added and incubated for from 72 h to about 120 h before analysis. HEK293T cells were transfected using lipofectamine 2000 (Invitrogen, Carlsbad, CA) as instructed on the product manual.

Tet-v3.0 Efficiency.

HEK293T cells were transfected as described above. Briefly, HEK293T cells were seeded in a 24-well plate for from 70% to about 80% of confluency at the time of transfection. A DNA-lipid complex that consists of 0.25 μg R2-74 pAcBac, 0.25 μg WT PylRS pAG26, 0.25 μg PylT pAG38, and 1.5 μl of lipofectamine 2000 reagent diluted in 50 μl of DMEM was added. To express Tet-v3.0 incorporated protein, Tet-v3.0-methyl, Tet-v3.0-ethyl, Tet-v3.0-isopropyl, or Tet-v3.0-butyl was added at 0.1 mM or 0.3 mM concentration at the time of transfection. No Tet-v3.0 was added to confirm the specificity of the genetic code expansion system. Images were taken at 6 h, 24 h, 48 h, and 72 h using Metamorph software (Molecular Devices, Sunnyvale, CA) and cooled CCD camera (CoolSNAP HQ, Photometrics, Tucson, AZ) connected to Axiovert 100S inverted fluorescence microscope (Zeiss, Germany). Results are shown in FIGS. 20 (HEK293T) and 21 (HEK293 cells).

Figure 20:
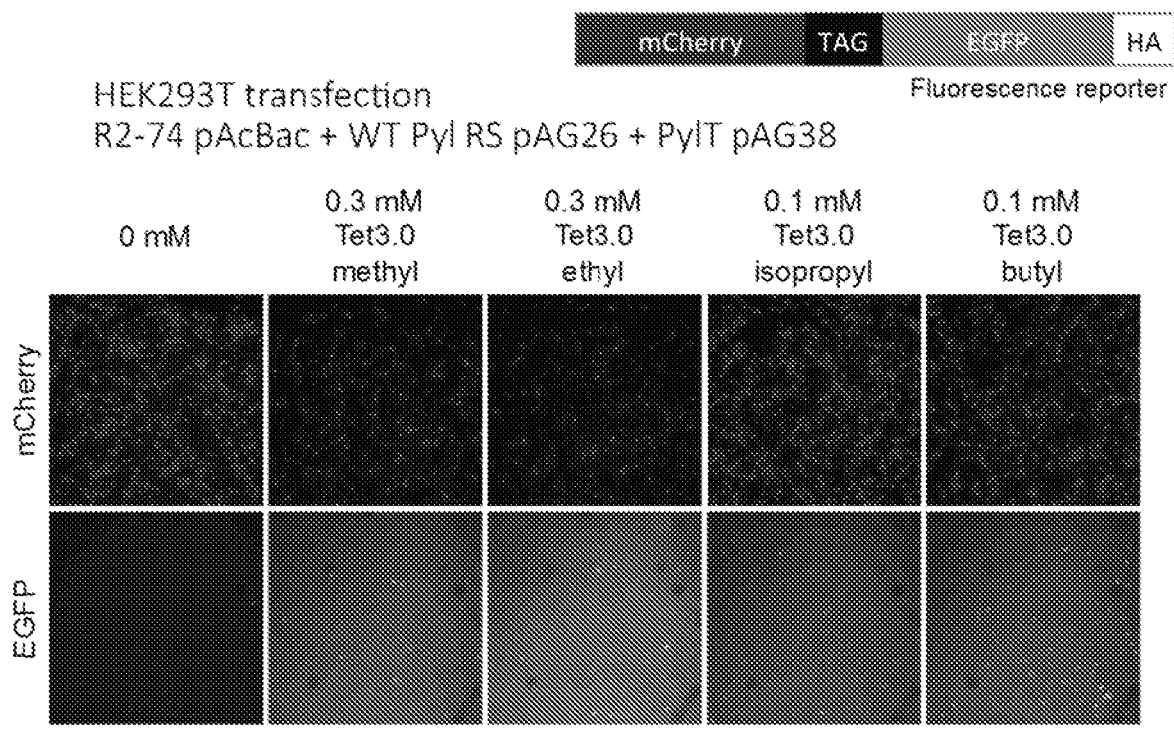
FIG. 20 compares the efficiency of incorporation of Tet-v3.0-methyl, Tet-v3.0-ethyl, Tet-v3.0-isopropyl, and Tet-v3.0-n-butyl into the fluorescence reporter in HEK293T cells. HEK293T cells were transfected with 0.25 μg R2-74 pAcBac, 0.25 μg pAG26 wt PylRS, and 0.25 μg pAG38 PylT for 72 h using lipofectamine 2000 in the presence of the Tet-v3.0 amino acids as indicated. Images were captured after 72 h to estimate the transfection efficiency and Tet-v3.0 amino acid incorporation efficiency. mCherry was detected at high frequency showing the efficiency of transfection. EGFP was detected with slightly different efficiency for each Tet-v3.0 amino acid confirming Tet-v3.0 incorporation in eukaryotic cells.

FIG. 20 compares the efficiency of incorporation of Tet-v3.0-methyl, Tet-v3.0-ethyl, Tet-v3.0-isopropyl, and Tet-v3.0-n-butyl into the fluorescence reporter in HEK293T cells. HEK293T cells were transfected with 0.25 μg R2-74 pAcBac, 0.25 μg pAG26 wt PylRS, and 0.25 μg pAG38 PylT for 72 h using lipofectamine 2000 in the presence of the Tet-v3.0 amino acids as indicated. Images were captured after 72 h to estimate the transfection efficiency and Tet-v3.0 amino acid incorporation efficiency. mCherry was detected at high frequency showing the efficiency of transfection. EGFP was detected with slightly different efficiency for each Tet-v3.0 amino acid.

Figure 21:
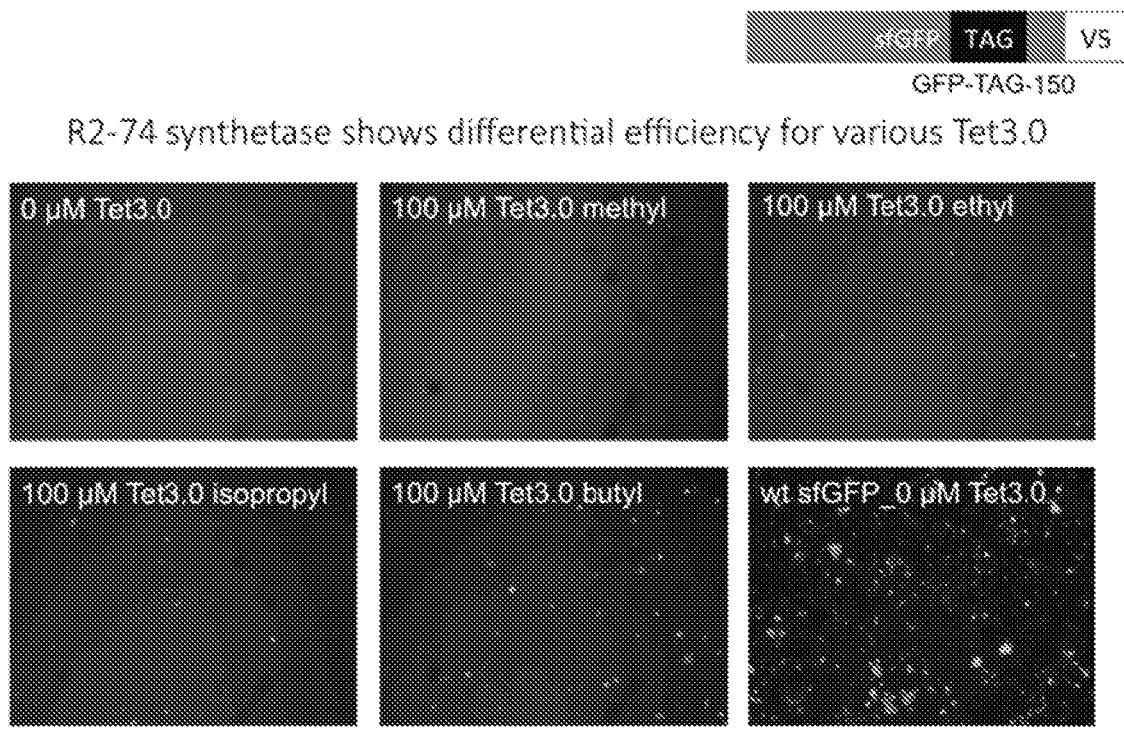
FIG. 21 compares the efficiency of incorporation of Tet-v3.0-methyl, Tet-v3.0-ethyl, Tet-v3.0-isopropyl, and Tet-v3.0-n-butyl into GFP-TAG-150 protein in HEK293 cells. HEK293 cells were transfected for 120 h with GFP-TAG-150 pAcBac and R2-74 pAcBac using lipofectamine 2000 in the presence of 0.1 mM of the Tet-v3.0 amino acid. The images were captured under the same condition for comparison and pseudo-colored. Wt sfGFP was used as a positive control for transfection.
Figure 22A:
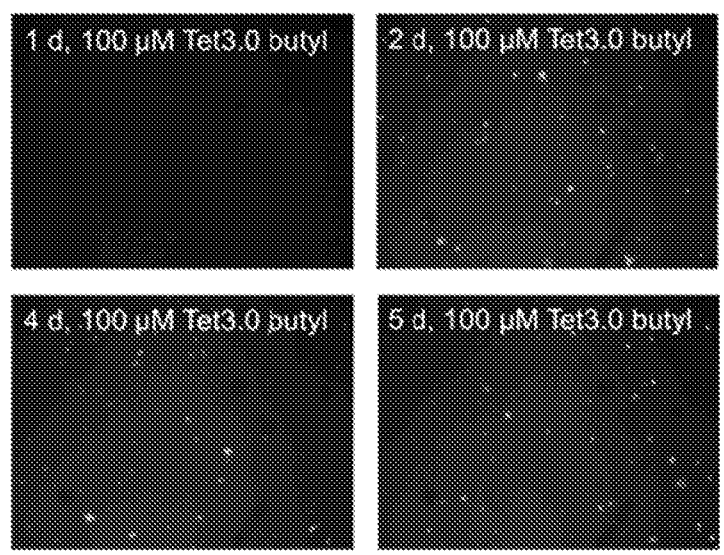
FIGS. 22A and 22B compare the time course expression of GFP-TAG-150-Tet-v3.0-n-butyl protein in HEK293 cells. HEK293 cells were transfected for 120 h with GFP-TAG-150 pAcBac and R2-74 pAcBac using lipofectamine 2000 in the presence of 0.1 mM Tet-v3.0-n-butyl (FIG. 22A). The images were captured at 1 d, 2 d, 4 d, and 5 d after transfection and pseudo-colored.
Figure 22B:
Figure 22B:
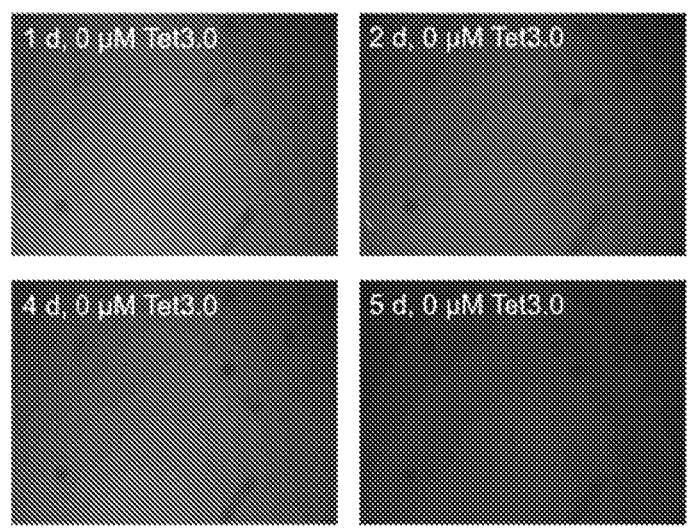
Figure 23A:
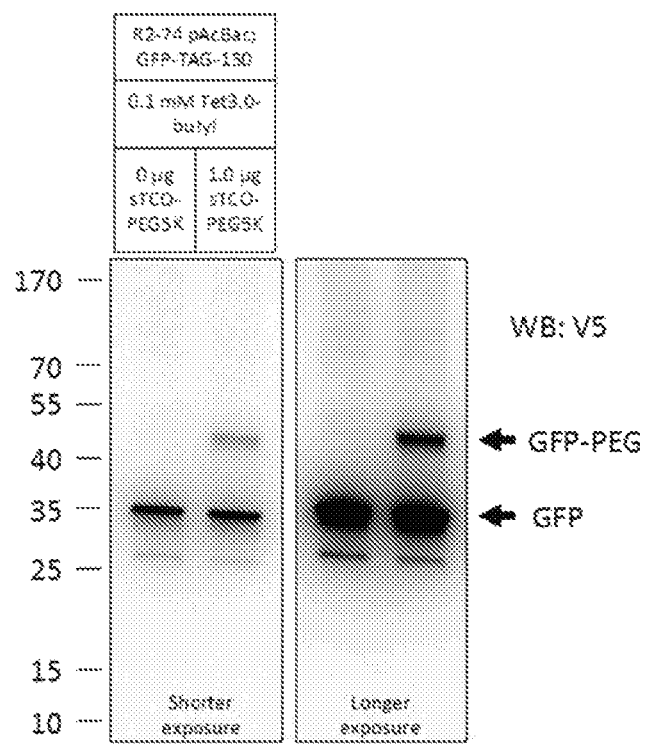
FIGS. 23A and 23B illustrate the results of the electrophoretic mobility shift assay for mammalian cells expressed tetrazine (Tet-v3.0-n-butyl) protein is reactive with sTCO. To confirm the integrity of tetrazine functional group in tet3.0 in animal cells HEK293 cells expressing GFP-Tet-3.0-butyl at site 150 were lysed in non-reducing Laemmli buffer after 72 h~120 h. One tenth of the lysates were incubated with 1 μg sTCO-PEG5000 for 10 min at RT, and analyzed by western blot using mouse anti-V5 antibody.
Figure 23B:
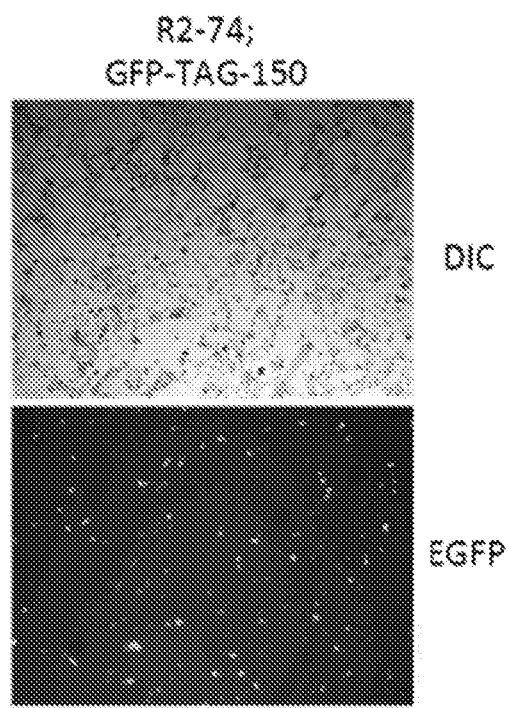

FIG. 21 compares the efficiency of incorporation of Tet-v3.0-methyl, Tet-v3.0-ethyl, Tet-v3.0-isopropyl, and Tet-v3.0-n-butyl into GFP-TAG-150 protein in HEK293 cells. HEK293 cells were transfected for 120 h with GFP-TAG-150 pAcBac and R2-74 pAcBac using lipofectamine 2000 in the presence of 0.1 mM of the Tet-v3.0 amino acid. A DNA-lipid complex that consists of 0.25 μg R2-74 pAcBac, 0.25 μg GFP-TAG-150 pAcBac, and 1 μl of lipofectamine 2000 reagent diluted in 50 μl of DMEM was added and incubated for 72 h. To express Tet-v3.0 incorporated protein, Tet-v3.0-methyl, Tet-v3.0-ethyl, Tet-v3.0-isopropyl, or Tet-v3.0-n-butyl was added at 0.1 mM or 0.3 mM concentration at the time of transfection. No Tet-v3.0 was added to confirm the specificity of the genetic code expansion system. The images were captured under the same condition for comparison and pseudo-colored. Wt sfGFP was used as a positive control for transfection.

Electrophoretic Mobility Shift Assay.

To confirm the integrity of tetrazine functional group in Tet-v3.0 in animal cells, HEK293 cells were transfected for with 1 μg R2-74 pAcBac and 1 μg GFP-TAG-150 pAcBac using jetPRIME reagent. 0.1 mM Tet-v3.0-n-butyl was added at the time of transfection and cell lysates were prepared in non-reducing Laemmli buffer after about 72 h to about 120 h. One tenth of the lysates were incubated with 1 μg sTCO-PEG5000 for 10 min at RT, and analyzed by western blot using mouse anti-V5 antibody (Invitrogen). Results are shown in FIGS. 22A, 22B, 23A, and 23B.

Example 6

General Synthesis of Tetrazine Amino Acids

Figure 14:
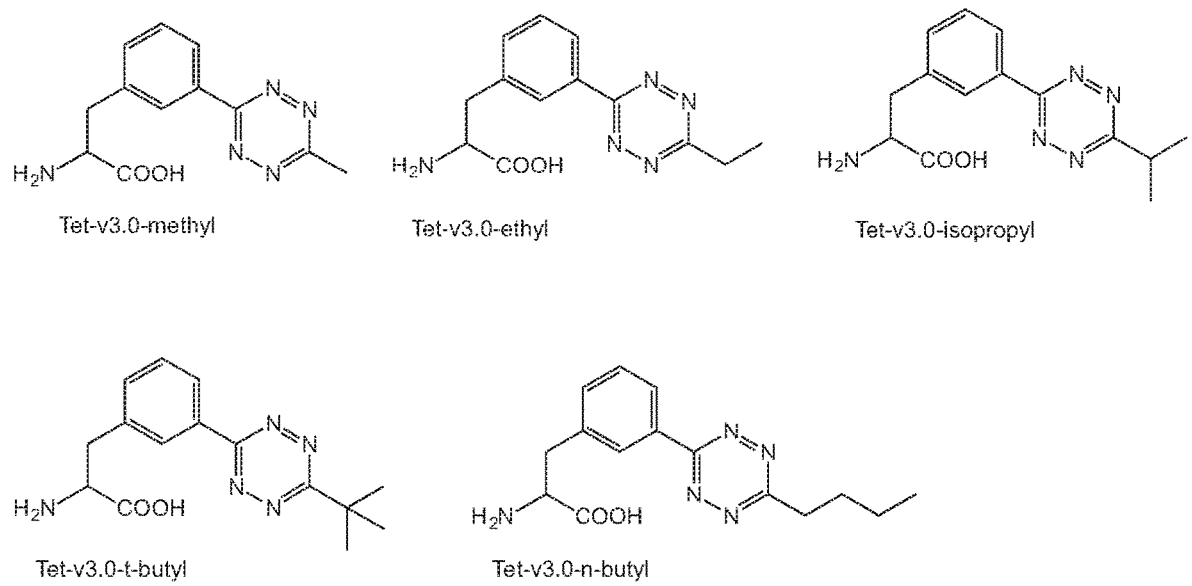
FIG. 14 illustrates representative tetrazine amino acids of the invention: 3-(6-methyl-s-tetrazin-3-yl)phenylalanine (Tet-v3.0-methyl), 3-(6-ethyl-s-tetrazin-3-yl)phenylalanine (Tet-v3.0-ethyl), 3-(6-isopropyl-s-tetrazin-3-yl)phenylalanine (Tet-v3.0-isopropyl), 3-(6-t-butyl-s-tetrazin-3-yl)phenylalanine (Tet-v3.0-t-butyl), and 3-(6-n-butyl-s-tetrazin-3-yl)phenylalanine (Tet-v3.0-n-butyl).

In this example, the general synthesis of tetrazine amino acids is described. The synthesis of 4-(6-methyl-s-tetrazin-3-yl)phenylalanine (Tet-v2.0-methyl) is described in Example 1 and illustrated in FIG. 4. The synthesis of 3-(6-methyl-s-tetrazin-3-yl)phenylalanine (Tet-v3.0-methyl) is described in Example 2 and illustrated in FIG. 11. Representative Tet-v2.0 derivatives are shown in FIG. 12A. Representative Tet-v3.0 derivatives are shown in FIG. 14.

General Synthetic Procedure.

A 25 mL microwave reaction flask was equipped with a stir bar and oven dried for 24 hours. The flask was then allowed to cool to 25° C. in a dessicator. To the flask was added N-(tert-butoxycarbonyl)-cyano-L-phenylalanine (150 mg, 0.52 mmol), Ni(OTf)$_2$ (92.2 mg, 0.26 mmol), and nitrile (5.2 mmol). The flask was purged with argon gas, and anhydrous hydrazine (0.811 mL, 25.83 mmol) was added. The flask was sealed and let stir in an oil bath at 60° C. for 24 hours. The mixture was removed from heat and allowed to cool to 25° C., after which the seal was removed. Sodium nitrite (2 M, 5.2 mL) was then added while continuing to stir the mixture. The product was then extracted with water (3×), and the combined aqueous layers were washed with ethyl acetate (3×). 4 M HCl was added dropwise to the aqueous solution until pH 3 was achieved. The product was then extracted with ethyl acetate (3×) and the combined organic layers were washed with water (2×) and brine (1×). The organic solution was subsequently dried with MgSO$_4$. The product was then concentrated and purified via flash chromatography separation (7:3 hexanes:ethyl acetate 1% acetic acid). Various fractions were selected for TLC to confirm their compositions. Fractions whose TLC produced one spot (Rf 0.33) were combined and concentrated to afford boc-protected tetrazine phenylalanine as a dark pink oil (5-75% yield). To a vessel containing the boc-protected tetrazine phenylalanine 4 M HCl/1,4-dioxane (2.1 mL) was added. The vessel was flushed with argon, sealed, and allowed to stir at 25° C. for 8 hours with stirring. The mixture was then concentrated, rinsed with minimal ethyl acetate, and again concentrated. The product was rinsed with minimal pentane (3×) and concentrated to afford tetrazine phenylalanine hydrochloride salt as (85-95% yield) as a bright pink powder that was used without further purification.

TABLE 7

Yields of representative tetrazine amino acids.

| Tetrazine amino acid | Yield |
| --- | --- |
| Tet-v2.0-methyl | 60% |
| Tet-v2.0-ethyl | 71% |
| Tet-v2.0-isopropyl | 55% |
| Tet-v2.0-n-butyl | 50% |
| Tet-v3.0-methyl | 57% |
| Tet-v3.0-ethyl | 63% |
| Tet-v3.0-isopropyl | 42.5% |
| Tet-v3.0-n-butyl | 45% |
| Tet-v3.0-t-butyl | 6% |

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for making a protein or a polypeptide, comprising:
   culturing a cell in a medium including a tetrazine amino acid, the tetrazine amino acid comprising an amino acid bound directly to a tetrazine via a carbon link, wherein the cell includes:
   a nucleic acid that encodes a protein or a polypeptide and comprises a selector codon;
   an orthogonal tRNA that is specific for the tetrazine amino acid and that recognizes an orthogonal *Methanococcus jannaschii* (Mj) aminoacyl-tRNA synthetase that is specific for the tetrazine amino acid and recognizes the selector codon, and
   the orthogonal Mj aminoacyl-tRNA synthetase aminoacylates the orthogonal tRNA with the tetrazine amino acid; and
   in the cultured cell and using the orthogonal Mj aminoacyl-tRNA synthetase and the orthogonal tRNA, incorporating the tetrazine amino acid into the protein or the polypeptide to provide a protein or polypeptide having a tetrazine amino acid residue bound to the protein or the polypeptide, wherein the tetrazine amino acid is selected from the group consisting of 4-(6-methyl-s-tetrazin-3-yl)phenylalanine (Tet-v2.0-methyl), 4-(6-ethyl-s-tetrazin-3-yl)phenylalanine (Tet-v2.0-ethyl), 4-(6-isopropyl-s-tetrazin-3-yl)phenylalanine (Tet-v2.0-isopropyl), and 4-(6-butyl-s-tetrazin-3-yl)phenylalanine (Tet-v2.0-n-butyl), wherein the orthogonal Mj aminoacyl-tRNA synthetase comprises modified amino acids at positions 32, 65, 108, 109, 158, and 162, and wherein the modified amino acids are:
   Ala or Gly at position 32;
   Ala, Ser, Val, or Gln at position 65;
   Glu, Gln, His, Asp, Ser, Leu, or Ala at position 108;
   His, Glu, Ser, Asp, or Pro at position 109;
   Gly, Ser, or Asn at position 158; and
   Ser, Ala, Gly, or Asn at position 162.

2. The method of claim 1, wherein the tetrazine amino acid is incorporated into the protein or the polypeptide to provide the protein or polypeptide having the tetrazine amino acid residue at a yield of at least 50 milligrams per liter of the medium.

3. The method of claim 1, wherein the tetrazine amino acid reacts with a trans cyclooctene (TCO) to attach a molecule to the tetrazine amino acid via a cycloaddition, wherein the tetrazine amino acid residue is bound to the protein or the polypeptide via a carbon link from the tetrazine moiety.

4. The method of claim 3, wherein the tetrazine amino acid binds with cyclopropane-fused trans cyclooctene (sTCO) at a bimolecular rate constant of at least $16,035 \pm 1500$ $M^{-1}s^{-1}$.

5. The method of claim 3, wherein the tetrazine amino acid binds with cyclopropane-fused trans cyclooctene (sTCO) at a bimolecular rate constant of at least $72,500 \pm 1660$ $M^{-1}s^{-1}$.

6. The method of claim 1, further comprising culturing an orthogonal Mj tyrosyl tRNA synthetase (RS)/tRNA$_{CUA}$ pair capable of incorporating the tetrazine amino acid in *E. coli*.

7. The method of claim 1, further comprising cloning the orthogonal Mj aminoacyl-tRNA synthetase into a vector that contains a copy of an orthogonal Mj/tRNA$_{CUA}$.

\* \* \* \* \*

SEQUENCE LISTING

<160> NUMBER OF SEQ ID NOS: 7

<210> SEQ ID NO 1
<211> LENGTH: 26
<212> TYPE: DNA
<213> ORGANISM: Artificial Sequence
<220> FEATURE:
<223> OTHER INFORMATION: Synthetic

<400> SEQUENCE: 1
cgcgcgccat ggacgaattt gaaatg                                    26

<210> SEQ ID NO 2
<211> LENGTH: 37
<212> TYPE: DNA
<213> ORGANISM: Artificial Sequence
<220> FEATURE:
<223> OTHER INFORMATION: Synthetic

<400> SEQUENCE: 2
gactcagtct aggtacccgt tgaaactgc agttata                         37

<210> SEQ ID NO 3
<211> LENGTH: 25
<212> TYPE: DNA
<213> ORGANISM: Artificial Sequence
<220> FEATURE:
<223> OTHER INFORMATION: Synthetic

<400> SEQUENCE: 3
cttcctggaa atcaagagcc ccatc                                     25

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
gttccaggtc gccgtgcatg                                           20

<210> SEQ ID NO 5
<211> LENGTH: 18
<212> TYPE: DNA
<213> ORGANISM: Artificial Sequence
<220> FEATURE:
<223> OTHER INFORMATION: Synthetic

<400> SEQUENCE: 5
tgcacggcga cctggaac                                             18

<210> SEQ ID NO 6
<211> LENGTH: 22
<212> TYPE: DNA
<213> ORGANISM: Artificial Sequence
<220> FEATURE:
<223> OTHER INFORMATION: Synthetic

<400> SEQUENCE: 6
ggggctcttg atttccagga ag                                        22

<210> SEQ ID NO 7
<211> LENGTH: 22
<212> TYPE: DNA
<213> ORGANISM: Artificial Sequence

```
<220> FEATURE:
<223> OTHER INFORMATION: Synthetic

<400> SEQUENCE: 7
catgtaggcc tgataagcgt ag                                              22
```